(12) United States Patent
Abdel-Magid et al.

(10) Patent No.: US 9,024,009 B2
(45) Date of Patent: May 5, 2015

(54) PROCESS FOR THE PREPARATION OF COMPOUNDS USEFUL AS INHIBITORS OF SGLT

(75) Inventors: Ahmed F. Abdel-Magid, Ambler, PA (US); Maureen Chislom, Schwenksville, PA (US); Steven Mehrman, Quakertown, PA (US); Lorraine Scott, North Wales, PA (US); Kenneth M. Wells, Hillsborough, NJ (US); Fan Zhang-Plasket, Willow Grove, PA (US); Sumihiro Nomura, Osaka (JP); Mitsuya Hongu, Osaka (JP); Yuichi Koga, Osaka (JP)

(73) Assignees: Janssen Pharmaceutica N.V., Beerse (BE); Mitsubishi Tanabe Pharma Corporation, Osaka (JP)

( * ) Notice: Subject to any disclaimer, the term of this patent is extended or adjusted under 35 U.S.C. 154(b) by 1197 days.

(21) Appl. No.: 12/207,252

(22) Filed: Sep. 9, 2008

(65) Prior Publication Data

US 2009/0233874 A1 Sep. 17, 2009

Related U.S. Application Data

(60) Provisional application No. 60/971,067, filed on Sep. 10, 2007, provisional application No. 61/018,822, filed on Jan. 3, 2008.

(51) Int. Cl.
| | | |
|---|---|---|
| *C07H 7/04* | (2006.01) | |
| *C07H 7/06* | (2006.01) | |
| *C07D 409/10* | (2006.01) | |
| *C07D 409/14* | (2006.01) | |
| *C07D 417/14* | (2006.01) | |
| *A61K 31/7042* | (2006.01) | |
| *A61K 31/7056* | (2006.01) | |
| *A61K 31/706* | (2006.01) | |
| *A61P 3/10* | (2006.01) | |
| *C07D 309/12* | (2006.01) | |
| *C07D 309/10* | (2006.01) | |

(52) U.S. Cl.
CPC ............ *C07D 409/10* (2013.01); *C07D 309/12* (2013.01); *C07D 309/10* (2013.01); *C07D 409/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 2,799,241 A | 7/1949 | Wurster | |
| 4,160,861 A | 7/1979 | Cole et al. | |
| 4,584,369 A | 4/1986 | Klein et al. | |
| 5,149,838 A | 9/1992 | Humphrey et al. | |
| 5,292,461 A | 3/1994 | Juch et al. | |
| 5,401,435 A | 3/1995 | Burzio et al. | |
| 5,424,406 A | 6/1995 | Tslhara et al. | |
| 5,610,294 A | 3/1997 | Lam et al. | |
| 5,731,292 A | 3/1998 | Tsujihara et al. | |
| 5,767,094 A | 6/1998 | Tsujihara et al. | |
| 5,780,483 A | 7/1998 | Widdowson et al. | |
| 5,830,873 A | 11/1998 | Tsujihara et al. | |
| 5,861,385 A | 1/1999 | Angerbauer et al. | |
| 5,945,533 A | 8/1999 | Kometani et al. | |
| 6,048,842 A | 4/2000 | Tsujihara et al. | |
| 6,069,238 A | 5/2000 | Hitchcock et al. | |
| 6,153,632 A | 11/2000 | Rieveley | |
| 6,277,833 B1 | 8/2001 | Angerbauer et al. | |
| 6,297,363 B1 | 10/2001 | Kubo et al. | |
| 6,414,126 B1 | 7/2002 | Ellsworth et al. | |
| 6,420,513 B2 | 7/2002 | Minami | |
| 6,448,415 B1 | 9/2002 | Lee et al. | |
| 6,475,521 B1 | 11/2002 | Timmins et al. | |
| 6,515,117 B2 | 2/2003 | Ellsworth et al. | |
| 6,562,791 B1 | 5/2003 | Maurya et al. | |
| 6,617,313 B1 | 9/2003 | Maurya et al. | |
| 6,627,611 B2 | 9/2003 | Tomiyama et al. | |
| 6,800,761 B1 | 10/2004 | Franc et al. | |
| 7,008,959 B2 | 3/2006 | Franc et al. | |
| 7,045,665 B2 | 5/2006 | Fujikura et al. | |
| 7,074,826 B2 | 7/2006 | Wechter et al. | |
| 7,084,123 B2 | 8/2006 | Fujikura et al. | |
| 7,202,350 B2 | 4/2007 | Imamura et al. | |
| 7,271,153 B2 | 9/2007 | Nishimura et al. | |
| 7,288,528 B2 | 10/2007 | Frick et al. | |
| 7,294,618 B2 | 11/2007 | Fushimi et al. | |
| 7,375,213 B2 | 5/2008 | Deshpande et al. | |
| 7,417,032 B2 | 8/2008 | Eckhardt et al. | |
| 7,511,022 B2 | 3/2009 | Beavers et al. | |
| 7,566,699 B2 | 7/2009 | Fushimi et al. | |
| 7,576,064 B2 | 8/2009 | Kikuchi et al. | |
| 7,666,845 B2 | 2/2010 | Cook et al. | |
| 7,932,379 B2 * | 4/2011 | Deshpande et al. | .......... 536/124 |
| 7,943,582 B2 | 5/2011 | Nomura et al. | |

(Continued)

FOREIGN PATENT DOCUMENTS

| | | |
|---|---|---|
| CA | 2 494 177 A1 | 2/2004 |
| EP | 0355750 A1 | 2/1990 |

(Continued)

OTHER PUBLICATIONS

Lee, D. et al "Recent advances in Aryl C-Glycoside Synthesis" Curr. Top. Med. Chem. (2005) vo 5, pp. 1333-1350.*

(Continued)

*Primary Examiner* — Leigh Maier

(57) ABSTRACT

The present invention is directed to a novel process for the preparation of compounds having inhibitory activity against sodium-dependent glucose transporter (SGLT) being present in the intestine or kidney.

31 Claims, 5 Drawing Sheets

(56) References Cited

U.S. PATENT DOCUMENTS

| | | |
|---|---|---|
| 7,943,788 B2 | 5/2011 | Nomura et al. |
| 2001/0041674 A1 | 11/2001 | Tomiyama et al. |
| 2002/0032164 A1 | 3/2002 | Dale et al. |
| 2002/0052326 A1 | 5/2002 | Washburn |
| 2002/0111315 A1 | 8/2002 | Washburn et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0191121 A1 | 10/2003 | Miller et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2008/0027122 A1 | 1/2008 | Nomura et al. |
| 2008/0119422 A1 | 5/2008 | Nomura et al. |
| 2008/0132563 A1* | 6/2008 | Kakinuma et al. ............ 514/432 |
| 2008/0146515 A1 | 6/2008 | Nomura et al. |
| 2008/0234366 A1 | 9/2008 | Bindra et al. |
| 2009/0124702 A1 | 5/2009 | Siva Satya Krishna Babu et al. |
| 2010/0099883 A1 | 4/2010 | Fillers et al. |
| 2011/0009347 A1 | 1/2011 | Liang et al. |
| 2011/0087017 A1 | 4/2011 | Farina et al. |
| 2011/0212905 A1 | 9/2011 | Nomura et al. |
| 2012/0058941 A1 | 3/2012 | Nomura et al. |
| 2012/0115799 A1 | 5/2012 | Wang et al. |

FOREIGN PATENT DOCUMENTS

| | | |
|---|---|---|
| EP | 0348184 B1 | 3/1993 |
| EP | 0579204 A2 | 1/1994 |
| EP | 0579204 A3 | 1/1994 |
| EP | 0625513 B1 | 9/1999 |
| EP | 1172362 A1 | 1/2002 |
| EP | 1338603 A1 | 8/2003 |
| EP | 1 528 066 A1 | 5/2005 |
| EP | 1845095 | 10/2007 |
| EP | 1956023 A1 | 3/2008 |
| GB | 2359554 A | 8/2001 |
| JP | 59039889 A | 3/1984 |
| JP | 63-233975 A | 9/1988 |
| JP | 4-253974 A | 9/1992 |
| JP | 06246354 A | 9/1994 |
| JP | 07242526 A | 9/1995 |
| JP | 9-263549 A | 10/1997 |
| JP | 2000-34230 A | 2/2000 |
| JP | 2000-34239 A | 2/2000 |
| JP | 2001-288178 A | 10/2001 |
| JP | 2002167430 A | 6/2002 |
| JP | 2003-12686 A1 | 1/2003 |
| JP | 2003238417 A | 8/2003 |
| JP | 2003313168 A | 11/2003 |
| WO | 93/09100 A1 | 5/1993 |
| WO | 93/21178 A1 | 10/1993 |
| WO | 94/14807 A1 | 7/1994 |
| WO | WO 1996/13258 | 5/1996 |
| WO | 97/17949 A1 | 5/1997 |
| WO | 97/25033 A1 | 7/1997 |
| WO | 98/42347 A1 | 10/1998 |
| WO | 99/67236 A | 12/1999 |
| WO | 00/27823 A1 | 5/2000 |
| WO | 00/28989 A1 | 5/2000 |
| WO | 00/74681 A1 | 12/2000 |
| WO | WO 01/27128 | 4/2001 |
| WO | 01/32157 A2 | 5/2001 |
| WO | 01/64669 A1 | 9/2001 |
| WO | WO 01/68660 A1 | 9/2001 |
| WO | WO 01/74834 A1 | 10/2001 |
| WO | WO 01/74835 A1 | 10/2001 |
| WO | 01/85167 A1 | 11/2001 |
| WO | 02/26706 A2 | 4/2002 |
| WO | WO 02/053573 A1 | 7/2002 |
| WO | 02/070020 A2 | 9/2002 |
| WO | 02/070020 A3 | 9/2002 |
| WO | WO 02/068439 A1 | 9/2002 |
| WO | WO 02/068440 A1 | 9/2002 |
| WO | WO 02/083066 A2 | 10/2002 |
| WO | 02/094262 A1 | 11/2002 |
| WO | WO 02/088157 A1 | 11/2002 |
| WO | 02/096357 A2 | 12/2002 |
| WO | 03/000712 A1 | 1/2003 |
| WO | WO 03/011880 A1 | 2/2003 |
| WO | WO 03/020737 A1 | 3/2003 |
| WO | 03/043621 A1 | 5/2003 |
| WO | 03/087104 A1 | 10/2003 |
| WO | WO 03/099836 A1 | 12/2003 |
| WO | WO 2004/007517 A1 | 1/2004 |
| WO | WO 2004/013118 A1 | 2/2004 |
| WO | WO 2004/014931 A1 | 2/2004 |
| WO | WO 2004/019958 A1 | 3/2004 |
| WO | WO 2004/052902 A1 | 6/2004 |
| WO | WO 2004/052903 A1 | 6/2004 |
| WO | 2004/063209 A2 | 7/2004 |
| WO | 2004/063209 A3 | 7/2004 |
| WO | 2004/064806 A | 8/2004 |
| WO | 2004/076470 A2 | 9/2004 |
| WO | WO 2004/080990 A1 | 9/2004 |
| WO | 2004/087727 A1 | 10/2004 |
| WO | 2004/099230 A1 | 11/2004 |
| WO | 2004/113359 A1 | 12/2004 |
| WO | 2005/009539 A2 | 2/2005 |
| WO | 2005/009954 A2 | 2/2005 |
| WO | WO 2005/012326 | 2/2005 |
| WO | 2005/058845 A2 | 6/2005 |
| WO | WO 2006/010557 | 2/2006 |
| WO | WO 2006/080577 A1 | 8/2006 |
| WO | 2006/108842 A1 | 10/2006 |
| WO | 2007/025943 A2 | 3/2007 |
| WO | 2007/031548 A2 | 3/2007 |
| WO | 2007/087441 A2 | 8/2007 |
| WO | WO 2008/013322 A1 | 1/2008 |
| WO | 2008/020011 A1 | 2/2008 |
| WO | 2008/034859 A1 | 3/2008 |
| WO | 2008/055870 A1 | 5/2008 |
| WO | 2008/055940 A2 | 5/2008 |
| WO | 2008/069327 A1 | 6/2008 |
| WO | 2008/070609 | 6/2008 |
| WO | 2009/022010 A1 | 2/2009 |
| WO | 2009/023537 | 2/2009 |
| WO | 2009/026537 A1 | 2/2009 |
| WO | 2009/091082 A1 | 7/2009 |
| WO | WO 2009/121945 | 10/2009 |

OTHER PUBLICATIONS

Apsel, B. et al "General entries to C-aryl glycosides . . ." Tet. Lett. (2003) vol. 44, pp. 1075-1077.*

(56) References Cited

OTHER PUBLICATIONS

Kaelin, D. et al "General strategies for the synthesis . . ." Jacs (2001) vol. 123, pp. 6937-6938.*

Martin, S. "Unified strategy for the synthesis of C-aryl glucosides" Pure Appl. Chem. (2003) vol. 75, No. 1, pp. 63-70.*

Unger et al. "Hyperglycemia as an inducer as well as a consequence of impaired islet cell function and insulin resistance: implications for the management of diabetes" Diabetologia, vol. 28, p. 119-121 (1985).

Rossetti et al. "Glucose Toxicity"; Diabetes Care, vol. 13, p. 610-630 (1990).

Rossetti et al. Correction of Hyperglycemia with Phlorizin Normalizes Tissue Sensitivity to Insulin in diabetic rats Journal of Clinical Investigation, vol. 79, p. 1510-1515 (1987).

Rossetti et al. Effect of Chronic Hyperglycemia on in Vivo Insulin Secretion in Partially Pancreatectomized Rats Journal of Clinical Investigation, vol. 80, p. 1037-1044 (1987).

Kahn et al. "Normalization of Blood Glucose in Diabetic Rats with Phlorizin Treatment Reverses Insulin-resistant Glucose Transport in Adipose Cells without Restoring Glucose Transporter Gene Expression" Journal of Clinical Investigation, vol. 87, p. 561-570 (1991).

Tsujihara et al. "Na+ Glucose Cotransporter (SGLT) Inhibitors as Antidiabetic Agents. 4. Synthesis and Pharmacological Properties of 4'-Dehydroxyphlorizin Derivatives Substituted on the B Ring" Journal of Medicinal Chemistry, vol. 42, p. 5311-5324 (1999).

Arakawa et al, Improved diabetic syndrome in C57BL/KsJ-db/db Mice by Oral Administration of the Na+-Glucose Cotransporter Inhibitor T-1095: British Journal of Pharmacology, vol. 132, p. 578-586 (2001).

Ueta et al. "Long-term treatment with the Na+-glucose contransporter inhibitor T1095 causes sustained improvement in hyperglycemia and prevents diabetic neuropathy in Goto-Kakizaki Rats" Life Sci., 76(23): 2655-68 (2005), etc.].

Roshan Ahmad et al., Nucleosides, Nucleotides & Nucleic Acids, vol. 20, No, 9, (2001), pp. 1671-1682.

Khosrow Zamani et al., Journal of the Chinese Chemical Society, vol. 49, (2002), pp. 1041-1044.

Galal T. Maatooq et al., Phytochemistry, vol. 44, No. 1, (Jan. 1997), pp. 187-190.

Hongu et al., Chem. Pharm. Bull, vol. 46, No. 1, pp. 22-33, (1998).

PCT International Search Report dated Feb. 8, 2008 for PCT/US2008/75700.

Extended European Search Report relating to co-pending EP patent application No. 08831144.4. Date of Mailing of extended EP search report: Mar. 16, 2012.

Greene et al., "Protective Groups in Organic Synthesis.", 3rd Edition, 1999, pp. 119-121, XP002670712.

Greene et al., "Protective Groups in Organic Synthesis.", 3rd Edition, 1999, pp. 170.

Adachi et al., "T-1095, a Renal Na+-Glucose Transporter Inhibitor, Improves Hyperglycemia in Streptozotocin-Induced Diabetic Rats." Metabolism, Aug. 2000, pp. 990-995, vol. 49(8).

Albertoni Borghese et al., "Inhibitors of sodium/glucose cotransport.", Drugs of the Future, Apr. 2009, pp. 297-305, vol. 34(4), Prous Science, XP007915342.

Amishiro et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, pp. 1393-1403, vol. 47(10).

Appleton et al., "A Mild and Selective C-3 Reductive Alkylation of Indoles", Tetrahedron Letters, 1993, pp. 1529-1532, vol. 34(9).

Banker, Modern Pharmaceutics, Third Edition, Marcel Dekker, Inc., published 1996, p. 596.

Beck-Nielsen et al., "In Vivo Glucose Metabolism, Insulin Secretion and, Insulin Action in Europids with non-insulin-dependent Diabetes mellitus (NiDDM) and Their First-degree Relatives.", Diabetic Medicine, Sep. 1996, pp. S78-S84, vol. 13(9 Supp. 6).

Benhaddou et al.,"Tetra-n-propylammonium tetraoxoruthenate(VII): a reagent of choice for the oxidation of diversely protected glycopyranoses and glycofuranoses to lactones", Carbohydrate Research, 1994, pp. 243-250, vol. 260.

Bertolini et al., "A New Simple One-Pot Regioselective Preparation of Mixed Diesters of Carbonic Acid.", Journal of Organic Chemistry, 1998, pp. 6031-6034, vol. 63(17).

Blair et al., "Effect of Ring Fluorination on the Pharmacology of Hallucinogenic Tryptamines", J. Med. Chem., 2000, pp. 4701-4710, vol. 43.

Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., 2000, pp. 2664-2674, vol. 43(14).

Bookser, B.C., "2-Benzyloxymethyl-5-(tributylstannyptetrazole. A reagent for the preparation of 5-aryl-and 5-heteroaryl-1 H-tetrazoles via the Stille reaction," Tetrahedron Letters, 2000, pp. 2805-2809, vol. 41.

Bouillon et al., "Synthesis of novel halopyridinylboronic acids and esters. Part 2: 2,4, or 5-Halopyridin-3-yl-boronic acids and esters," Tetrahedron, 2002, pp. 3323-3328, vol. 58.

Bouillon et al., "Synthesis of novel halopyridinylboronic acids and esters. Part 3: 2, or 3-Halopyridin-4-yl-boronic acids and esters," Tetrahedron, 2002, pp. 4369-4373, vol. 58.

Bouillon et al., "Synthesis of novel halopyridinylboronic acids and esters. Part 4: Halopyridin2-yl-boronic acids and esters are stable, crystalline partners for classical Suzuki cross-coupling," Tetrahedron, 2003, pp. 10043-10049, vol. 59.

Braga et al., "Making crystals from crystals: a green route to crystal engineering and polymorphism.", Chem. Commun., 2005, pp. 3635-3645.

Brooks et al., "Boron Trichloride/Tetra-n-Butylammonium Iodide: A Mild, Selective Combination Reagent for the Cleavage of Primary Alkyl Aryl Ethers", J. Org. Chem., 1999, pp. 9719-9721, vol. 64.

CAS Reg. No. 487001-40-1, IPOrganisers, Entered STN Feb. 7, 2003, pp. 1-2.

Caumo et al., "Insulin Sensitivity from Meal Tolerance Tests in Normal Subjects: A Minimal Model Index.", J. Of Clinical Endocrinology & Metabolism, 2000, pp. 4396-4402, vol. 85(11).

Cicchillo et al., "A convenient synthesis of glycosyl chlorides from sugar hemiacetals using triphosgene as the chlorine source," Carbohyfrate Research, 2000, pp. 431-434, vol. 328.

Clayden et al., "Dearomatizing Cyclization of Arylsulfonylalkoxymethyl Lithiums: A Route to the Podophyllotoxin Skeleton," Organic Letters, 2003, pp. 831-834, vol. 5(6).

Comins et al., "Synthesis of 3-Substituted Indoles Via N-Acylindolium Ions", Tetrahedron Letters, 1986, pp. 1869-1872, vol. 27(17).

Cottet et al., "Recommendable Routes to Trifluoromethyl-Substituted Pyridine—and Quinolinecarboxylic Acids," Eur. J. Org. Chem., 2003, pp. 1559-1568.

Czernecki et al., "C-Glycosides. 7. Stereospecific C-Glycosylation of Aromatic and Heterocyclic Rings", J. Org. Chem., 1989, pp. 610-612, vol. 54.

De Las Heras et al., "Alkylating Nucleosides 1. Synthesis and Cytostatic Activity of NGlycosyl(halomethyl)-1,2,3-triazoles. A New Type of Alkylating Agent," Journal of Medicinal Chemistry, 1979,pp. 496-501, vol. 22(5).

Deeg et al., "Pioglitazone and Rosiglitazone Have Different Effects on Serum Lipoprotein Particle Concentrations and Sizes in Patients With Type 2 Diabetes and Dyslipidemia.", Diabetes Care, Oct. 2007, pp. 2458-2464, vol. 30(10).

Deetjen et al., "Renal Handling of D-Glucose and Other Sugars", Textbook of Nephrology, 3rd Edition, 1995, pp. 90-94. vol. 1.

Devivar et al., "Benzimidazole Ribonucleosides: Design, Synthesis, and Antiviral Activity of Certain 2-(Alkylthio)- and 2-(Benzylthio)-5,6-dichloro-1-(.beta.-Dribofuranosyl)benzimidazolesl.", J.Med. Chem., 1994, pp. 2942-2949, vol. 37.

Dewynter et al., "Synthesis of Pseudomucleosides containing Chiral Sulfahydantoins as Aglycone (II)", Tetrahedron, 1996, pp. 993-1004, vol. 52(3).

Dillard et al., "Indole Inhibitors of Human Nonpancreatic Secretory Phospholipase A2. 1. Indole-3-acetamides", J. Med. Chem., 1996, pp. 5119-5136, vol. 39.

(56) References Cited

OTHER PUBLICATIONS

Dinneen, S.F., "The Postprandial State: Mechanisms of Glucose Intolerance.", Diabetic Medicine, Aug. 1997, pp. S19-S24, vol. 14, Issue S3.
Dondoni et al., "Stereoselective synthesis of C-glycosylphosphonates from their ketols. Reconsideration of an abandoned route", Tetrahedron: Asymmetry, 2000, pp. 305-317, vol. 11.
Dondoni et al., "Thiazole-Based Synthesis of Formyl C-Glycosides", J. Org. Chem., 1994, pp. 6404-6412, vol. 59.
Dudash et al., "Glycosylated dihydrochalcones as potent and selective sodium glucose co-transporter 2 (SGLT2) inhibitors," Bioorganic & Medicinal Chemistry Letters, 2004, pp. 5121-2125, vol. 14.
Dunn et al., "Analgetic and antiinflammatory 7-Aroylbenzofuran-5-ylacetic acids and 7- Aroylbenzothiophene-5-ylacetic Acids.", Journal of Med. Chem., 1986, pp. 2326-2329, vol. 29(1).
Eid et al., "Reaction of Some 1,2,4-Triazines with Acetobromoglucose", Arch. Pharm (Weinheim), 1990, pp. 243-245, vol. 323.
Ellsworth et al., "Aglycone exploration of C-arylglucoside inhibitors of renal sodium-dependent glucose transporter SGLT2," Bioorganic & Medicinal Chemistry Letters, 2008, pp. 4770-4773, vol. 18.
Ellsworth et al., "C-Arylglucoside synthesis: triisopropylsilane as a selective reagent for the reduction of an anomeric C-phenyl ketal," Tetrahedron: Asymmetry, 2003, pp. 3243-3247, vol. 14.
Emancipator, K., "Laboratory diagnosis and monitoring of diabetes mellitus.", Am J Clin Pathol., Nov. 1999, pp. 65-674, vol. 112(5).
Frahn et al., "Functionalized AB-Type Monomers for Suzuki Polycondensation," Synthesis, Nov. 1997, pp. 1301-1304.
Fresneda et al., "Synthesis of the indole alkaloids meridianins from the tunicate Aplidium meridianum" Tetrahedron, 2001, pp. 2355-2363, vol. 57.
Fuller et al., "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.
Ganesh et al., "Synthesis and biological evaluation of fluorescently labeled epothilone analogs for tubulin binding studies," Tetrahedron, 2003, pp. 9979-9984, vol. 59.
Gershell, L., "Type 2 diabetes marker", Nature Reviews Drug Discovery, May 2005, pp. 367-368, vol. 4.
Gohier et al., "ortho-Metalation of Unprotected 3-Bromo and 3-Chlorobenzoic Acids with Hindered Lithium Dialkylamides," J. Org. Chem., 2003, pp. 2030-2033, vol. 68.
Goldberg R.B., "Prevention of Type 2 Diabetes.", Medical Clinics of North America, Jul. 1998, pp. 805-821, vol. 82(4).
Gong, H., et al., "Diastereoselective Ni-Catalyzed negishi Cross Coupling Approach to Saturated, Fully Oxygenated C-Alkyl and C-Aryl Glycosides.", Journal of the American Chemical Society, Sep. 10, 2008, pp. 12177-12183, vol. 130(36), XP002612364.
Goodman & Gilman's the Pharmacological Basis of Therapeutics, 10th Edition, McGraw-Hill Medical Publishing Division, 2001, pp. 54-57.
Gronowitz et al., "Some Substitution Reactions of 1-(2-Thienyl)pyrazole and 1-(3'-Thienyl)pyrazole," Chemica Scripta., 1979, pp. 157-161, vol. 13.
Groop et al., "Characterization of the Prediabetic State.", American Journal of Hypertension, Sep. 1997, pp. 172S-180S, vol. 10(9Part2).
Gros et al., "Efficient and Regioselective Access to Bis-heterocycles via Palladium-Catalysed Coupling of Organostannanes and Organozincates Derived from C-6 Lithiated 2-Methoxypyridine," Synthesis, 1999, pp. 754-756, No. 5.
Haffner S.M., "Impaired Glucose Tolerance, Insulin Resistance and Cardiovascular Disease.", Diabetic Medicine, Aug. 1997, pp. S12-S18, vol. 14.
Haffner S.M., "The Prediabetic Problem: Development of Non-Insulin-Dependent Diabetes Mellitus and Related Abnormalities.", Journal of Diabetes and Its Complications, Mar-Apr. 1997, pp. 69-76, vol. 11(2).

Han et al., "Dapagliflozin, a Selective SGLT2 Inhibitor, Improves Glucose Homeostasis in Normal and Diabetic Rats", Diabetes, Jun. 2008, pp. 1723-1729, vol. 57, New York.
Handlon, A. L., "Sodium glucose co-transporter 2 (SGLT2) inhibitors as potential antidiabetic agents," Expert Opin. Ther. Patents, 2005, pp. 1531-1540, vol. 15(11).
Hixon et al., "Sizing Materials by Crushing and Grinding.", Chemical Engineer, Nov. 1990, pp. 94-103.
Hofslokken et al., "Convenient Method for the ortho-Formylation of Phenols.", Acta Chemica Scandinavica, 1999, pp. 258-262, vol. 53.
Horton et al., "Synthetic Routes to Higher-Carbon Sugars. Reaction of Lactones with 2-Lithio1,3-Dithiane", Carbohydrate Research, 1981, pp. 27-41, vol. 94.
Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, 1999, pp. 43-48, vol. 53(1).
Huang-Minlon, "Reduction of Steroid Ketones and other Carbonyl Compounds by Modified Wolff-Kishner Method", J. Am. Chem. Soc., Oct. 1949, pp. 3301-3303, vol. 71.
Ibrahim et al., "Facile Approach for the Selective Glycodisation of Cyclic Asymmetric Amides and Thioamides", Carbohydrate Letters, 1996, pp. 425-432, vol. 1.
Ibrahim et al., "Selective Synthesis and Structure of 2-N- and 3-S-Glucosyl-1,2,4-Triazoles of Potential Biological Interest", Carbohydrate Letters, 1999, pp. 331-338, vol. 3(5).
Idris et al., "Sodium-glucose co-transporter-2 inhibitors: an emerging new class of oral antidiabetic drug.", Diabetes, Obesity and Metabolism, 2009, pp. 79-88, vol. 11(2), GB, XP007915350.
!Isaji, M., "Sodium-glucose cotransporter inhibitor for diabetes," Current Opinion in Investigational Drugs, 2007, pp. 285-292, vol. 8(4).
Jain et al., "Polymorphism in Pharmacy.", Indian Drugs, 1986, pp. 315-329, vol. 23(6).
Kanai et al., "The Human Kidney Low Affinity Na+/Glucose Cotransporter SGLT2: Delineation of the Major Renal Reabsorptive Mechanism for D-Glucose", J. Clin. Invest., Jan. 1994, pp. 397-404, vol. 93.
Kasahara et al., "A missense mutation in the Na+/glucose cotransporter gene SGLT1 in a patient with congenital glucose-galactose malabsorption: normal trafficking but inactivation of the mutant protein," Biochimica et Biophysics Acta, 2001, pp. 141-147, vol. 1536.
Katz et al., "Quantitative Insulin Sensitivity Check Index: A Simple, Accurate Method for Assessing Insulin Sensitivity in Humans.", J. Of Clin. Endocrinology & Metabolism, 2000, pp. 2040-2410, vol. 85(7).
Ketcha et al., "Synthesis of Alyl-Substituted N-Protected Indoles via Acylation and Reductive Deoxygenation1" J. Org. Chem., 1989, pp. 4350-4356, vol. 54.
Khan et al, "Reactions of Phenyl-Substituted Heterocyclic Compounds—II. Nitrations and Brominations of 1-Phenylpyrazole Derivatives," Canadian Journal of Chemistry, 1963, pp. 1540-1547, vol. 41.
Kitagawa, K., et al., "Halogen—Magnesium Exchange via Trialkylmagnesates for the Preparation of Aryl- and Alkenylmagnesium Reagents", Angew. Chem. Int. Ed., 2000, pp. 2481-2493, vol. 39(14).
Knochel, P., et al., Organic Reactions, vol. 58, Chapter 2: Preparation and Application of Functionalized Organozinc Compounds by., pp. 417-490, Edited by L. E. Overman, et al., John Wiley &Sons, Inc., Publishers. (2001).
Lee et al., "Synthesis and in Vitro Activity of Novel Isoxazolyl Tetrahydropyridinyl Oxazolidinone Antibacterial Agents," Bioorganic & Medicinal Chemistry Letters, 2003, pp. 4117-4120, vol. 13.
Lieberman et al., "Pharmaceutical Dosage Forms.", Second Edition, 1990, Marcel Dekker Inc., pp. 462-472, vol. 2.
Lin et al., "Syntheses of Guanidinoglycosides with the Inventive use of Mitsunobu Conditions and 1, 8-Diazabicyclo[5.4.0]undec-7-ene.", Synthesis, 2003, pp. 255-261, No. 2.
Link et al., "A method for preparing C-glycosides related to phlorizin" Tetrahedron Letters, 2000, pp. 9213-9217, vol. 41.

(56) References Cited

OTHER PUBLICATIONS

Lipscombe et al., "Trends in diabetes prevalence, incidence, and mortality in Ontario, Canada 1995-2005: a population-based study", Lancet, 2007, vol. 369, pp. 750-756.

Mackenzie et al., "Biophysical Characteristics of the Pig Kidney Na+/Glucose Cotransporter SGLT2 Reveal a Common Mechanism for SGLT1 and SGLT2", J. Biol. Chem., 1996, vol. 271, pp. 32678-32683, No. 5.

Manis et al., "Metabolism of 4,4'-Methylenebis(2-chloroaniline) by Canine Liver and Kidney Slices.", Drug Metabolism and Disposition, 1986, pp. 166-174, vol. 14(2).

Marsenic, O. MD, "Glucose Control by the Kidney: An Emerging Target in Diabetes.", Am. J. Of Kidney Diseases, May 2009, pp. 875-883, vol. 53(5).

Matsuda et al., "Insulin Sensitivity Indices Obtained From Oral Glucose Tolerance Testing: Comparison with the euglycemic insulin clamp," Diabetes Care, Sep. 1999, pp. 1462-1470, vol. 22(9).

Matthews et al., "Homeostasis model assessment: insulin resistance and —cell function from fasting plasma glucose and insulin concentrations in man," Diabetolgia, 1985, pp. 412-419, vol. 28.

Meanwell et al., "Regiospecific Functionalization of 1,3-Dihydro-2H-benzimidazol-2-one and Structurally Related Cyclic Urea Derivates.", J. Org. Chemistry, 1995, pp. 1565-1582, vol. 60(6).

Meng et al., "Discovery of Dapagliflozin: a Potent, Selective Renal Sodium-Dependent Glucose Cotransporter 2 (SGLT2) Inhibitor for the Treatment of Type 2 Diabetes", J. Med. Chem., 2008, pp. 1145-149, vol. 51(5).

Messaoudi et al, "Synthesis and biological evaluation of oxindoles and benzimidazolinones derivatives," European Journal of Medicinal Chemistry, 2004,pp. 453-458, vol. 39.

Mewshaw et al., "New Generation Dopaminergic Agents. 7. Heterocyclic Bioisosteres that Exploit the 3-Oh-Phenoxyethylamine D2 Template", Bioorganic & Medicinal Chemistry Letters, 1999, pp. 2593-2598, vol. 9.

Miyaura et al., "Palladium-Catalyzed Cross-Coupling Reactions of Organoboron Compounds.", Chem. Rev., 1995, pp. 2457-2583, vol. 95(7).

Mongin, F., et al., "Deprotonation of furans using lithium magnesates", Tetrahedron Lett., 2005, pp. 7989-7992, vol. 46.

Nishimura et al, "Tissue-specific mRNA Expression Profiles of Human ATP-binding Cassette and Solute Carrier Transporter Superfamilies," Drug Metab. Pharmacokinet., 2005, pp. 452-477, vol. 20(6).

Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2012, pp. 6355-6360, vol. 53(17), American Chemical Society, US, XP007915324.

Nomura, S., "Renal Sodium-Dependent Glucose Cotransporter 2 (SGLT2) Inhibitors for New Anti-Diabetic Agent," Current Topics in Medicinal Chemistry, 2010, pp. 411-418, vol. 10(4).

Ohsumi et al. "Pyrazole-O-Glucosides as Novel Na+-Glucose Cotransporter (SGLT) Inhibitors" Bioorganic & Medicinal Chemistry Letters, 2003, pp. 2269-2272, vol. 13.

Oku et al., "T-1095, an Inhibitor of Renal Na+-Glucose Cotransporters, May Provide a Novel Approach to Treating Diabetes", Diabetes, Sep. 1999, pp. 1794-1800, vol. 48.

Orjales et al. "New 2-Piperazinylbenzimidazole Derivatives as 5-Ht-3 Antagonists. Synthesis and Pharmacological Evaluation," J. Med. Chem., 1997, pp. 586-593, vol. 40.

Parker et al., "Reductive Aromatization of Quinols: Synthesis of the C-Arylglycoside Nucleus of the Paulacandins and Chaetiacandin," Organic Letters, 2000, pp. 497-499, vol. 2(4).

Parrott, E.L., "Milling of pharmaceutical solids.", Journal of Pharmaceutical Sciences, Jun. 1974, pp. 813-829, vol. 63(6).

Patani et al., "Bioisosterism: A Rational Approach in Drug Design", Chem. Rev., American Chemical Society, 1996, pp. 3147-3176, vol. 96.

Peng et al., "Post-transcriptional Regulaton of Na+/Glucose Cotransporter (SGTL1) Gene Expression in LLC-PK1 Cells.", Journal of Biological Chemistry, 1995, pp. 20536-20542, vol. 270(35).

Perry's Chemical Engineers Handbook, Sixth Edition, 1984, pp. 21-13 to 21-19.

Pharmaceutical Sciences, Remington, 17th Ed., pp. 1585-1594 (1985).

Polshettiwar et al., "Pd-N-heterocycle carbene (NHR) organic silica: synthesis and application in carbon-carbon coupling reactions.", Tetrahedron, May 12, 2008, pp. 4637-4643, vol. 64(20), Elsevier Science Publishers, Amsterdam, NL, XP022607642.

Ramlo-Halsted B.A. & Edelman S.V., "The Natural History of Type 2 Diabetes Mellitus: Implications for Clinical Practice.", Primary Care, Dec. 1999, pp. 771-789, vol. 26(4).

Raynaud et al., "Revised Concept for the Estimation of Insulin Sensitivity From a Single Sample.", Diabetes Care, Jun. 1999, pp. 1003-1004, vol. 22(6).

Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.

Schmidt et al., "Synthese von Pyrazol-, Pyrazolo[3,4-d]pyrimidin- und 1H-1,2,4- Triazolgluconucleosiden aus Glucosehydrazonen," Liebigs Ann. Chem., 1981, pp. 2309- 2317. (English abstract only).

Schultheiss et al., "Pharmaceutical Cocrystals and Their Physicochemical Properties.", Crystal Growth and Design, Jun. 3, 2009, pp. 2950-2967, vol. 9(6), XP55011939.

Shan et al., "The role of cocrystals in pharmaceutical science.", Drug Discovery Today, May 1, 2008, pp. 440-446, vol. 13(9-10), Elsevier, Rahway, NJ, US, XP022649919.

Silverman, R. B., "The Organic Chemistry of Drug Design and Drug Action," Academic Press, 1992, pp. 19-23.

Somei et al., "The First and Simple Total Synthesis of Cappariloside AI," Heterocycles, 2000, pp. 1573-1578, vol. 53(7).

Srogl et al., "Sulfonium salts. Participants par excellence in metal-catalyzed carbon-carbon bond-forming reactions.", Journal of the American Chemical Society, Jan. 1, 1997, pp. 12376-12377, vol. 119, American Chemical Society, US, XP002955770.

Stoner et al., "Benzylation via Tandem Grignard Reaction—Lodotrimethylsilane (TMSI) Mediated.Reduction," Tetrahedron, 1995, pp. 11043-11062, vol. 51(41).

Stumvoll et al., "Use of the Oral Glucose Tolerance Test to Assess Insulin Release and Insulin Sensitivity.", Diabetes Care, Mar. 2000, pp. 295-301, vol. 23(3).

Tanaka et al. "Solid-Phase Synthesis of—Mono-Substituted Ketones and an Application to the Synthesis of a Library of Phlorizin Derivatives", Synlett, 2002, pp. 1427-1430, No. 9.

Thornber, C.T., "Isosterism and Molecular Modification in Drug Design.", Chem. Society Review, 1979, pp. 563-580, vol. 8.

Tilak et al, "Carcinogenesis by Thiophene Isosters of Polycyclic Hydrocarbons," Tetrahedron, 1960, pp. 76-95, vol. 9.

Tsujihara et al., Bio Clinica, 1998, pp. 324-328, vol. 13(4), English language Abstract.

Turk et al., "Glucose/galactose malabsorption caused by a defect in the Na+/glucose cotransporter," Nature, Mar. 1991, pp. 354-356, vol. 350.

Vippagunta et al., "Crystalline Solids". Advanced Drug Delivery Reviews, 2001, pp. 3-26, vol. 48.

Vishweshwar et al., "Pharmaceutical co-crystals.", Journal of Pharmaceutical Sciences, Mar. 1, 2006, pp. 499-516, vol. 95(3), American Pharmaceutical Association, Washington, US.

Wallace et al., "Use and Abuse of Homa Modeling.", Diabetes Care, Jun. 2004, pp. 1487-1495, vol. 27(6).

Wang et al, "Selective monolithiation of 2,5-dibromopyridine with butyllithium," Tetrahedron Letters, 2000, pp. 4335-4338, vol. 41.

Wareham et al., "Is There Really an epidemic of diabetes?", Diabetologia, 2005, pp. 1454-1455, vol. 48.

Washburn, W. N., "Evolution of sodium glucose co-transporter 2 inhibitors as anti-diabetic agents," Expert Opin. Ther. Patents, 2009, pp. 1485-1499, vol. 19(11).

(56) References Cited

OTHER PUBLICATIONS

Watanabe et al., "Cyclopentyl Methyl Ether as a New and Alternative Process Solvent.", Organic Process Research and Development, 2007, pp. 251-258, vol. 11.
Wild et al., "Global Prevalence of Diabetes: Estimates for the year 2000 and projections for 2030," Diabetes Care, May 2004, pp. 1047-1053, vol. 27(5).
Wolff, M. E., vol. 1: Principles and Practice, Burger's Medicinal Chemistry and Drug Discovery, 5th Edition, 1995, pp. 975-977.
Wright, E.M., "Renal Na+-glucose cotransporters," Am J Physiol Renal Physiol, 2001, pp. F10-F18, vol. 280.
Wurster D.E., "Air-suspension Technique of Coating Drug Particles* A Preliminary Report.", Journal of the American Pharmaceutical Association, Aug 1959, pp. 451-454, vol. 48(8).
Wurster, D.E., "Preparation of compressed tablet granulations by the air-suspension technique II.", Journal of the American Pharmaceutical Association, 1960, pp. 82-84, vol. 49(2).
Yang et al., "Convergent C-Glycolipid Synthesis via the Ramberg-Backlund Reaction: Active Antiproliferative Glycolipids", Org. Lett. 1999, pp. 2149-2151, vol. 1913).
Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives," J. Med. Chem., 2000, pp. 2929-2937, vol. 43.
Zhdanov, Y. et al., "Application of organozinc compounds in the synthesis of carbon-carbon derivatives of sugars.", Database Ca (online), Chemical Abstracts Service, Columbus, Ohio, USA, XP002612365. (1958).
Translation—Zhdanov, Y. et al., "Application of organozinc compounds in the synthesis of carbon-carbon derivatives of sugars.", Database CA (online), Chemical Abstracts Service, Columbus, Ohio, USA, XP002612365. (1958).
Zhou, F. Y., "The Synthesis and Characterization of 1-Benzyl-3-N-(Beta-D-glucosie-1-yl)-4-fluorouracil", Hecheng Huaxue, 2001, pp. 272-274, vol. 9(3).
Greene et al., "Protective Groups in Organic Synthesis.", 3rd Edition, 1999, pp. 116-121.
Klapars et al., "Copper-Catalyzed Halogen Exchange in Aryl Halides: An Aromatic Finkelstein Reaction", J. Am. Chem. Soc. 2002, pp. 14844-14845, vol. 124(50).
Schmidt et al., "Synthese von Pyrazol-, Pyrazolo[3,4-d]pyrimidin- und 1H-1,2,4- Triazolgluconucleosiden aus Glucosehydrazonen," Liebigs Ann. Chem., 1981, pp. 2309-2317.
Jianqun, et al., "Recent advances in palladium catalysts for aryl chlorides coupling reaction", Industrial Catalysis, Jul. 31, 2005, pp. 29-44, vol. 13(7).
Zhiyin, et al., "Cross-coupling reaction of Grignard reagent with thiophenyl halides by using nickel phosphine as catalyst and the synthesis of a-terthienyl", *Huaxue Shiji*, Dec. 31, 1995, pp. 289-290, vol. 17(5).
First Office Action relating to China Patent Application No. 201310358939.0, Issued on May 29, 2014.
Asahara et al., *Handbook of Solvents*, K.K. Kodansha., Sep. 1, 1985, Sixth Printing, pp. 47-51, Tokyo, JP.
Byrn et al., "Pharmaceutical Solids: A Strategic Approach to Regulatory Considerations.", Pharml. Res., 1995, pp. 945-954, vol. 12(7).
Bavin, M., "Process Development: Polymorphism in Process Development.", Chemistry & Industry, 1989, pp. 527-529, vol. 16.
Kozikowski et al., "Organometallics in Organic Synthesis. Applications of a New Diorganozinc Reaction to the Synthesis of C-Glycosyl Compounds With Evidence for an Oxonium-Ion Mechanism*.", Carbohydrate Research, 1987, pp. 109-124, vol. 171.

* cited by examiner

Representative XRD pattern for the crystalline form of the compound of formula (I-S)

Representative XRD pattern for the crystalline form of the compound of formula (I-K)

Representative XRD pattern for the crystalline form of the compound of formula (I-K)

Representative infra-red spectra in mineral oil, for the crystalline form of the compound of formula (I-K)

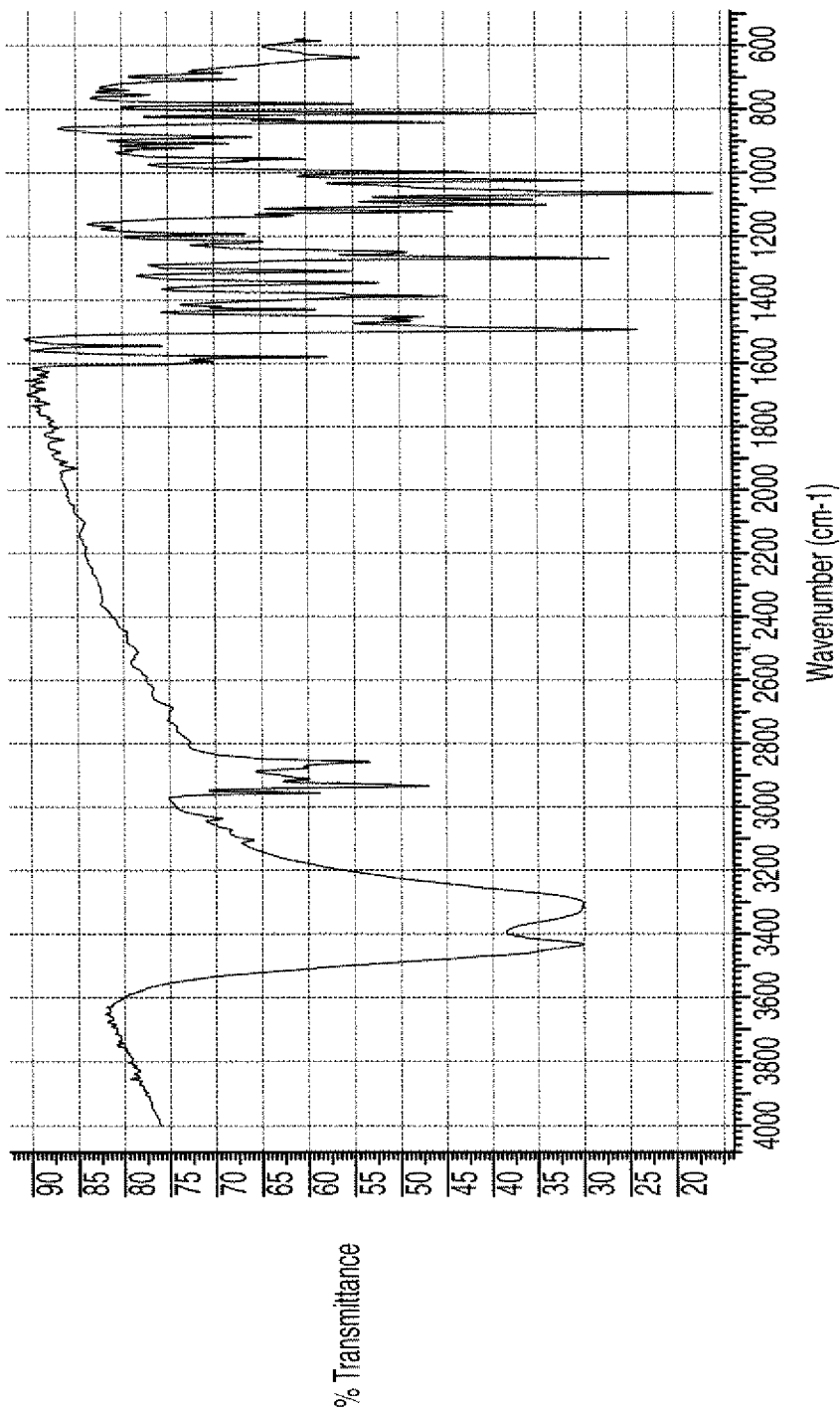

PROCESS FOR THE PREPARATION OF COMPOUNDS USEFUL AS INHIBITORS OF SGLT

CROSS REFERENCE TO RELATED APPLICATIONS

This application claims the benefit of U.S. Provisional Application 60/971,067, filed on Sep. 10, 2007; and U.S. Provisional Application 61/018,822 filed on Jan. 3, 2008, which are incorporated by reference herein in their entirety.

FIELD OF THE INVENTION

The present invention is directed to a novel process for the preparation of compounds having inhibitory activity against sodium-dependent glucose transporter (SGLT) being present in the intestine or kidney.

BACKGROUND OF THE INVENTION

Diet therapy and exercise therapy are essential in the treatment of diabetes mellitus. When these therapies do not sufficiently control the conditions of patients, insulin or an oral antidiabetic agent is additionally used for the treatment of diabetes. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. Namely, chronic hyperglycemia leads to decrease of insulin secretion and further to decrease of insulin sensitivity, and as a result, the blood glucose concentration is increased so that diabetes mellitus is self-exacerbated [cf., Diabetologia, vol. 28, p. 119 (1985); Diabetes Care, vol. 13, p. 610 (1990), etc.]. Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved [cf., Journal of Clinical Investigation, vol. 79, p. 1510 (1987); ibid., vol. 80, p. 1037 (1987); ibid., vol. 87, p. 561 (1991), etc.].

In addition, by treating diabetic animal models with SGLT inhibitory agents for a long time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001), Ueta, Ishihara, Matsumoto, Oku, Nawano, Fujita, Saito, Arakawa, Life Sci., in press (2005), etc.].

From the above, SGLT inhibitors may be expected to improve insulin secretion and insulin resistance by decreasing the blood glucose level in diabetic patients and further prevent the onset and progress of diabetes mellitus and diabetic complications.

SUMMARY OF THE INVENTION

The present invention is directed to a process for the preparation of compounds of formula (I)

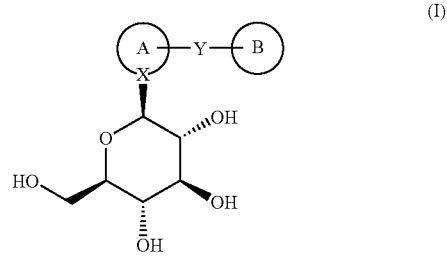

wherein Ring A and Ring B are one of the followings:

(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or (3) Ring A is an optionally substituted unsaturated fused heterobicyclic ring, wherein the sugar moiety X-(sugar) and the moiety -Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;

Y is —$(CH_2)_n$—; wherein n is 1 or 2;

provided that in Ring A, X is part of an unsaturated bond;

or a pharmaceutically acceptable salt thereof, or a prodrug thereof;

comprising

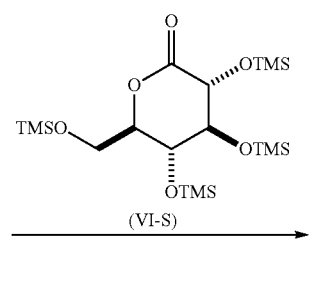

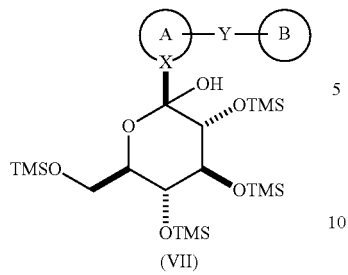

(VII)

reacting a compound of formula (V) with a compound of formula (VI-S), in the presence of an alkyl lithium, in an organic solvent, at a temperature in the range of from about 0° C. to about −78° C.; to yield the corresponding compound of formula (VII);

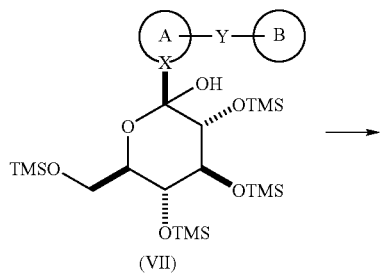

(VII)

reacting the compound of formula (VII) with BF$_3$OEt$_2$, in the presence of a trialkylsilane, in an organic solvent, to yield the corresponding compound of formula (VIII);

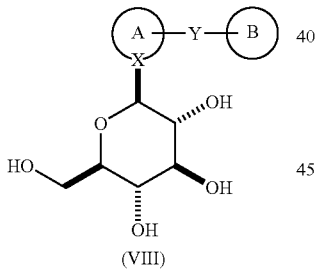

(VIII)

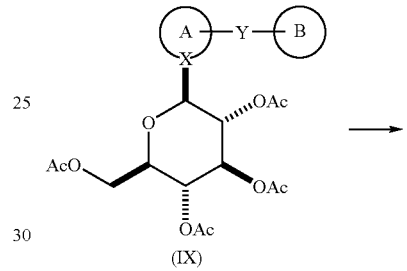

(IX)

reacting the compound of formula (VIII) with acetic anhydride or acetyl chloride, in the presence of an organic base, neat or in an organic solvent, to yield the corresponding compound of formula (IX); and

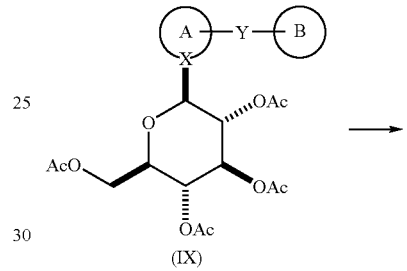

(IX)

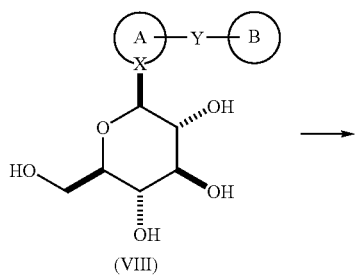

(I)

de-protecting the compound of formula (IX), to yield the corresponding compound of formula (I).

In an embodiment, the present invention is directed to a process for the preparation of a compound of formula (I-S)

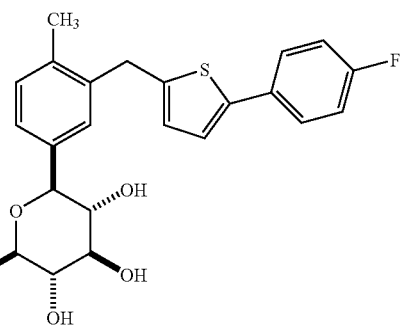

(I-S)

or a pharmaceutically acceptable salt thereof; (also known as 1-(β-D-glucopyranosyl)-4-methyl-3-[5-(4-fluorophenyl)-2-thienylmethyl]benzene); comprising

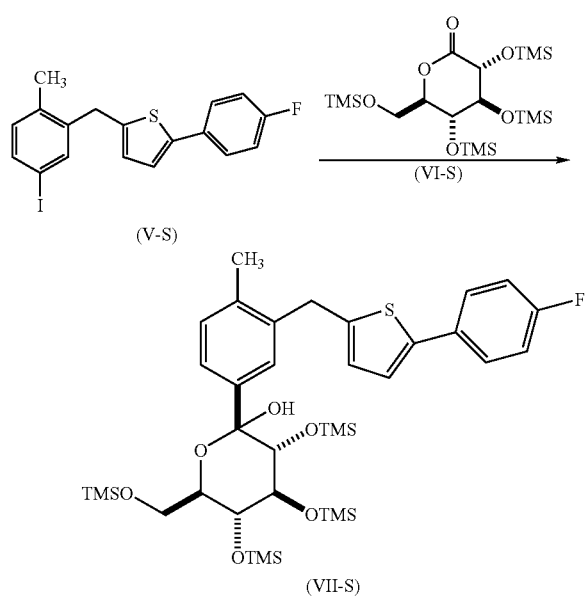
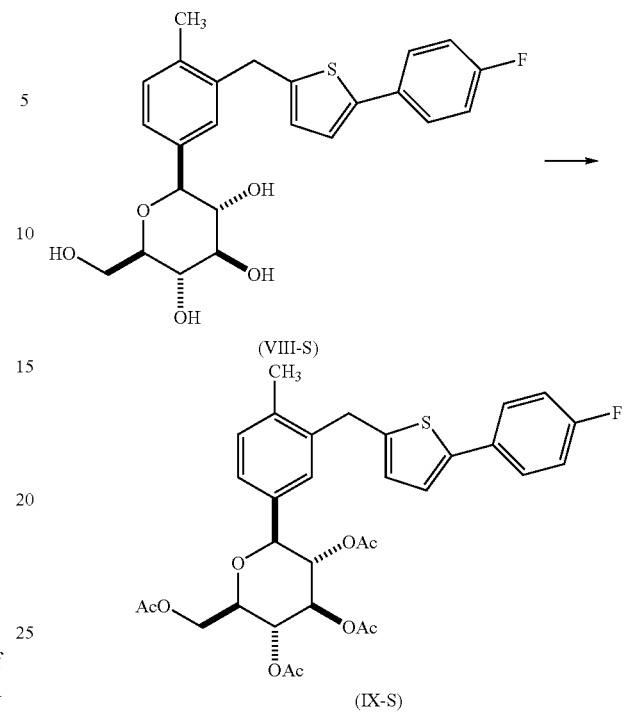

reacting a compound of formula (V-S), with a compound of formula (VI-S), in the presence of an alkyl lithium, in an organic solvent, at a temperature in the range of from about 0° C. to about −78° C., to yield the corresponding compound of formula (VII-S);

reacting the compound of formula (VIII-S) with acetic anhydride or acetyl chloride, in the presence of an organic base, neat or in an organic solvent, to yield the corresponding compound of formula (IX-S); and

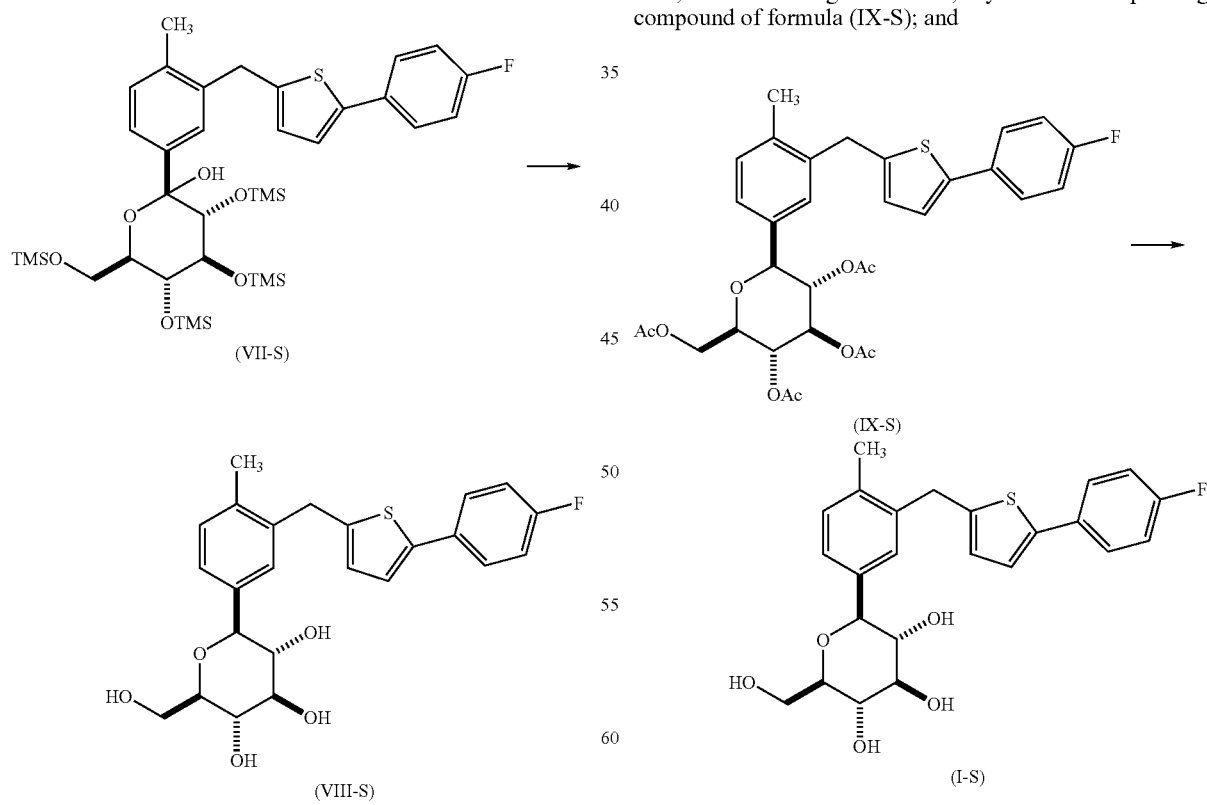

reacting the compound of formula (VII-S) with BF$_3$OEt$_2$, in the presence of a trialkylsilane, in an organic solvent, to yield the corresponding compound of formula (VIII-S);

de-protecting the compound of formula (IX-S) to yield the corresponding compound of formula (I-S).

The present invention is further directed to a process for the recrystallization of a compound of formula (I-S). In an embodiment of the present invention, the compound of formula (I-S) is recrystallized from a mixture of ethyl acetate and water, using heptane as an anti-solvent.

The present invention is further directed to a crystalline form of the compound of formula (I-S)

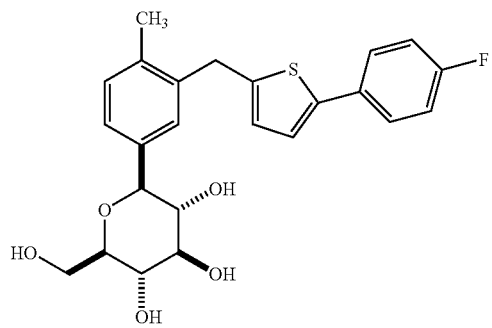

(I-S)

characterized by the powder X-ray diffraction pattern peaks as herein described. In an embodiment, the present invention is directed to a crystalline form of the compound of formula (I-S) prepared by recrystallizing a compound of formula (I-S) from a mixture of ethyl acetate and water, and using heptane as an anti-solvent.

In another embodiment, the present invention is directed to a process for the preparation of a compound of formula (I-K)

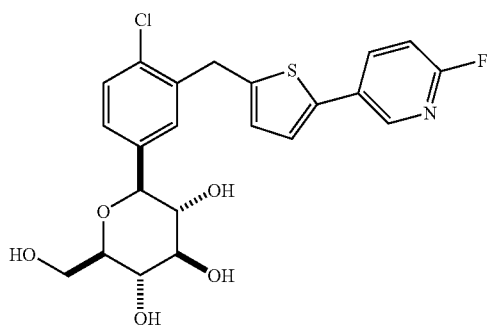

(I-K)

or a pharmaceutically acceptable salt thereof; (also known as 1-(β-D-glucopyranosyl)-4-chloro-3-[5-(6-fluoro-3-pyridyl)-2-thienylmethyl]benzene)

comprising

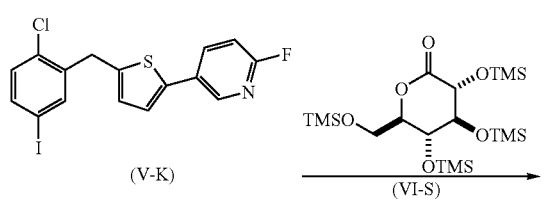

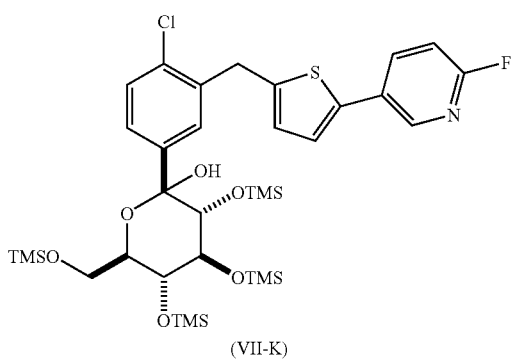

(VII-K)

reacting a compound of formula (V-K), with a compound of formula (VI-S), in the presence of an alkyl lithium, in an organic solvent, at a temperature in the range of from about 0° C. to about −78° C., to yield the corresponding compound of formula (VII-K);

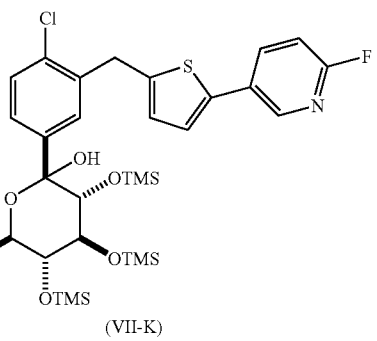

(VII-K)

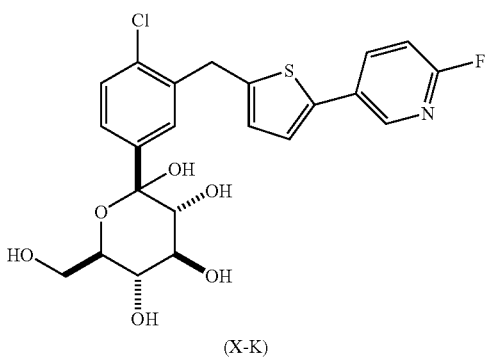

(X-K)

de-protecting the compound of formula (VII-K), to yield the corresponding compound of formula (X-K);

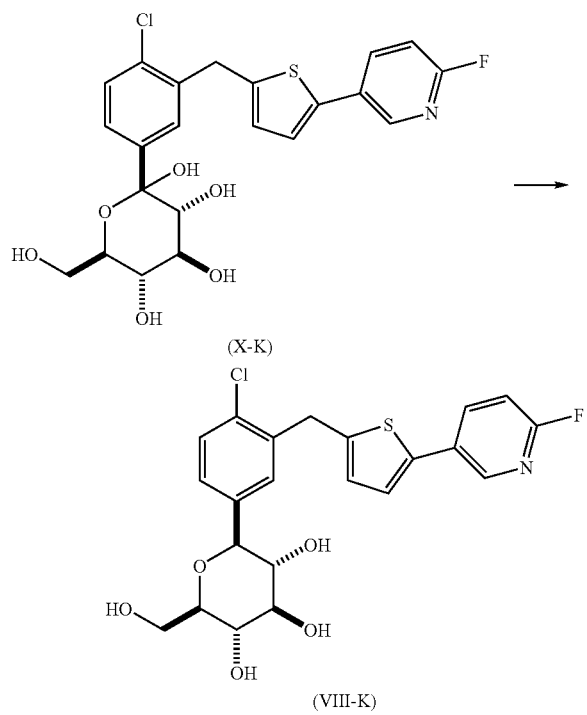

(X-K)

(VIII-K)

reacting the compound of formula (X-K) with $BF_3OEt_2$, in the presence of a trialkylsilane, in an organic solvent, to yield the corresponding compound of formula (VIII-K);

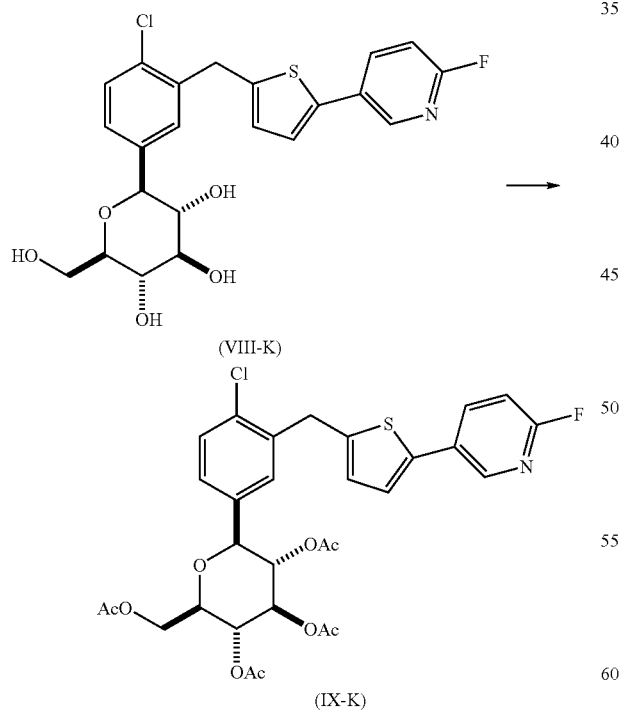

(VIII-K)

(IX-K)

reacting the compound of formula (VIII-K) with acetic anhydride or acetyl chloride, in the presence of an organic base, neat or in an organic solvent, to yield the corresponding compound of formula (IX-K); and

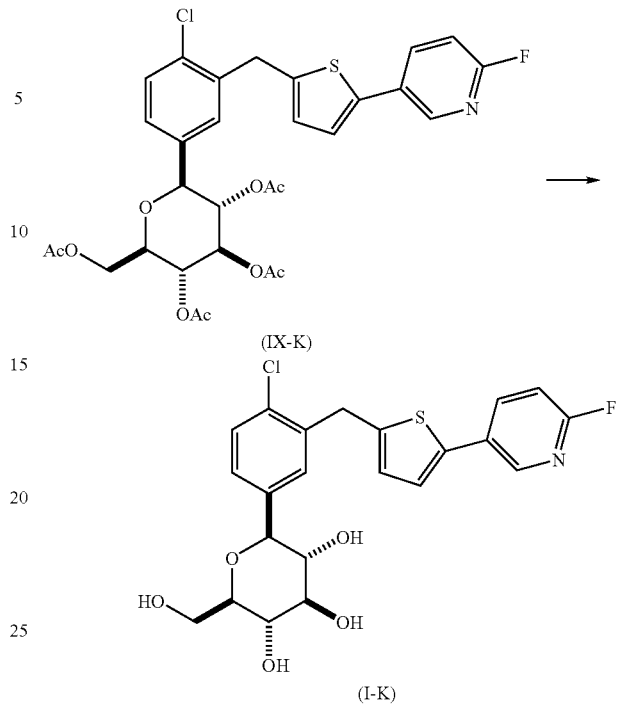

(IX-K)

(I-K)

de-protecting the compound of formula (IX-K) to yield the corresponding compound of formula (I-K).

The present invention is further directed to a crystalline form of the compound of formula (I-K)

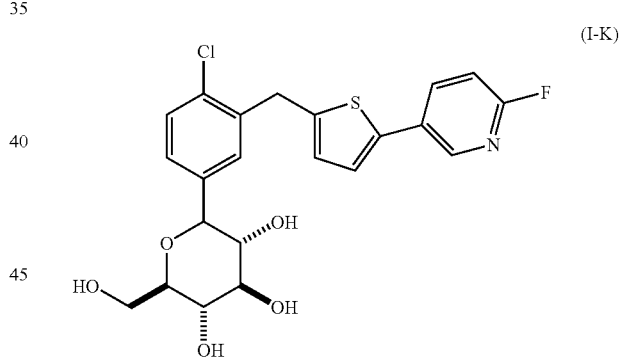

(I-K)

or a pharmaceutically acceptable salt thereof; (also known as 1-(β-D-glucopyranosyl)-4-chloro-3-[5-(6-fluoro-3-pyridyl)-2-thienylmethyl]benzene), which crystalline form may be characterized by its powder X-ray diffraction pattern peaks, as herein described. In an embodiment, the present invention is directed to process for the preparation and/or isolation of the crystalline form of the compound of formula (I-K).

The present invention is further directed to a product prepared according to any of the processes described herein.

Illustrative of the invention is a pharmaceutical composition comprising a pharmaceutically acceptable carrier and the product prepared according to any of the processes described herein. An illustration of the invention is a pharmaceutical composition made by mixing the product prepared according to any of the processes described herein and a pharmaceutically acceptable carrier. Illustrating the invention is a process for making a pharmaceutical composition comprising mixing the product prepared according to any of the processes described herein and a pharmaceutically acceptable carrier.

Illustrative of the invention is a pharmaceutical composition comprising a pharmaceutically acceptable carrier and a crystalline form of the compound of formula (I-S) or a crystalline form of the compound of formula (I-K), as described herein. An illustration of the invention is a pharmaceutical composition made by mixing a crystalline form of the compound of formula (I-S) or a crystalline form of the compound of formula (I-K), as described herein and a pharmaceutically acceptable carrier. Illustrating the invention is a process for making a pharmaceutical composition comprising mixing a crystalline form of the compound of formula (I-S) or a crystalline form of the compound of formula (I-K), as described herein and a pharmaceutically acceptable carrier.

Exemplifying the invention are methods of treating a disorder mediated by SGLT (including treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension,) comprising administering to the subject in need thereof a therapeutically effective amount of any of the compounds, crystalline forms or pharmaceutical compositions described above.

Further exemplifying the invention are methods of treating type 1 and type 2 diabetes mellitus, comprising administering to a subject in need of treatment a therapeutically effective amount of any of the compounds, crystalline forms or pharmaceutical compositions described above, alone or in combination with at least one antidiabetic agent, agent for treating diabetic complications, anti-obesity agent, antihypertensive agent, antiplatelet agent, anti-atherosclerotic agent and/or hypolipidemic agent.

BRIEF DESCRIPTION OF THE FIGURE(S)

FIG. 5 illustrates a representative infra-red spectrum of the crystalline of the compound of formula (I-K) from a KBr pellet.

DETAILED DESCRIPTION OF THE INVENTION

Figure 1:
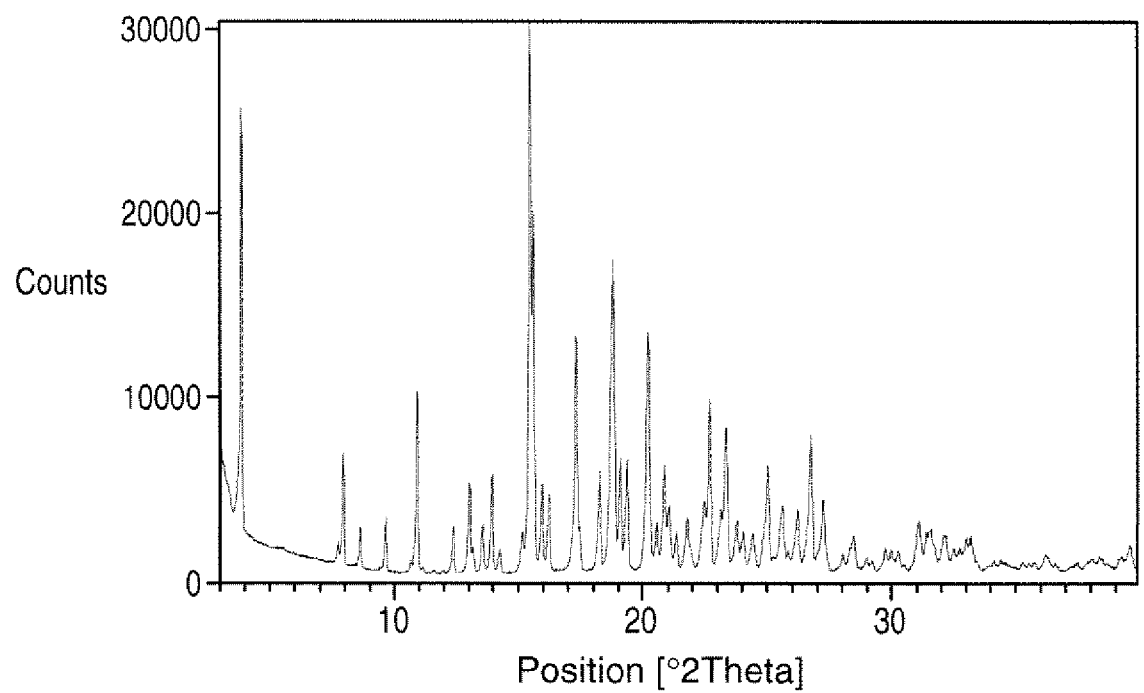
FIG. 1 illustrates a representative XRD pattern for the crystalline form of the compound of formula (I-S).

The present invention is directed to a process for the preparation of compound of formula (I)

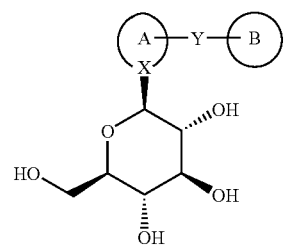

wherein X, Y, Ring A and Ring B are as herein defined. The compounds of the formula (I) exhibits an inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, obesity, and delayed wound healing. One skilled in the art will further recognize that any of the compounds or crystalline forms described herein may be used, if necessary, in combination with one or more of other anti-diabetic agents, antihyperglycemic agents and/or agents for treatment of other diseases; and may be administered in the same dosage form, or in a separate oral dosage form or by injection.

PCT Publication WO 2005/012326 discloses a class of compounds that are inhibitors of sodium-dependent glucose transporter (SGLT), including the compound of formula (I-K), also known as 1-(β-D-glucopyranosyl)-4-chloro-3-[5-(6-fluoro-3-pyridyl)-2-thienylmethyl]benzene, and the compound of formula (I-S), also known as 1-(β-D-glucopyranosyl)-4-methyl-3-[5-(4-fluorophenyl)-2-thienylmethyl]benzene. PCT Publication WO 2005/012326 further discloses the use of said compounds, including the compound of formula (I-K) and the compound of formula (I-S), for the treatment of diabetes, obesity, diabetic complications, and the like.

The present invention is further directed to processes for the preparation of a compound of formula (I-S) or a pharmaceutically acceptable salt thereof; and a compound of formula (I-K) or a pharmaceutically acceptable salt thereof.

The present invention is further directed to a novel crystalline form of the compound of formula (I-S) and a novel crystalline form of the compound of formula (I-K), as herein described in more detail. The present invention is further directed to processes for the preparation of the crystalline forms of the compound of formula (I-S) and the compound of formula (I-K) as herein described in more detail.

The term "halogen atom" or "halo" means chlorine, bromine and fluorine, and chlorine and fluorine are preferable.

The term "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by 1 to 4 substituents as listed below, if necessary.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group". Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary. Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc.

Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl group" means a formyl group and ones formed by binding an "alkyl group" to a carbonyl group.

The term "alkoxy group" means ones formed by binding an "alkyl group" to an oxygen atom.

The substituent for the above each group includes, for example, a halogen atom (fluorine, chlorine, bromine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a hetero-cyclylcarbonyl group, an alkoxy-carbonyl group, an alkenyloxy-carbonyl group, an alkynyloxy-carbonyl group, a cycloalkyloxy-carbonyl group, a cycloalkenyloxy-carbonyl group, a cyclo-alkynyl-oxycarbonyl group, an aryloxycarbonyl group, a hetero-cyclyloxycarbonyl group, an alkanoyloxy group, an alkenyl-carbonyloxy group, an alkynyl-carbonyloxy group, a cycloalkyl-carbonyloxy group, a cycloalkenyl-carbonyloxy group, a cycloalkynyl-carbonyloxy group, an arylcarbonyloxy group, a hetero-cyclylcarbonyloxy group, an alkylthio group, an alkenyl-thio group, an alkynylthio group, a cycloalkylthio group, a cycloalkenyl-thio group, a cycloalkynylthio group, an arylthio group, a heterocyclylthio group, an amino group, a mono- or di-alkylamino group, a mono- or di-alkanoylamino group, a mono- or di-alkoxy-carbonyl-amino group, a mono- or di-arylcarbonyl-amino group, an alkylsulfinylamino group, an alkyl-sulfonyl-amino group, an arylsulfinylamino group, an arylsulfonylamino group, a carbamoyl group, a mono- or di-alkylcarbamoyl group, a mono- or di-arylcarbamoyl group, an alkylsulfinyl group, an alkenyl-sulfinyl group, an alkynyl-sulfinyl group, a cycloalkyl-sulfinyl group, a cycloalkenyl-sulfinyl group, a cycloalkynyl-sulfinyl group, an arylsulfinyl group, a heterocyclyl-sulfinyl group, an alkyl-sulfonyl group, an alkenylsulfonyl group, an alkynylsulfonyl group, a cycloalkylsulfonyl group, a cycloalkenyl-sulfonyl group, a cycloalkynylsulfonyl group, an aryl-sulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylakyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a β-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric centers at a carbon atom containing any one of substituents. Therefore, the compound of the formula I may exist in the form of enantiomer or diastereomer, or a mixture thereof. When the present compound (I) contains a double bond, the present compound may exist in the form of geometric isomerism (cis-compound, trans-compound), and when the present compound (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound (I) includes an intramolecular salt, hydrate, solvate or polymorphism thereof.

Examples of the optionally substituted unsaturated monocyclic heterocyclic ring of the present invention include an unsaturated monocyclic heterocyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

Examples of the optionally substituted unsaturated fused heterobicyclic ring of the present invention include an unsaturated fused heterobicyclic ring which may optionally be substituted by 1-5 substituents selected from the group consisting of a halogen atom, a nitro group, a cyano group, an oxo group, a hydroxy group, a mercapto group, a carboxyl group, a sulfo group, an alkyl group, an alkenyl group, an alkynyl group, a cycloalkyl group, a cycloalkylidene-methyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenyl-carbonyl group, a cycloalkynyl-carbonyl group, an arylcarbonyl group, a heterocyclylcarbonyl group, an alkoxycarbonyl group, an alkenyloxycarbonyl group, an alkynyloxy-carbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cyclo-alkylcarbonyloxy group, a cycloalkenylcarbonyloxy group, a cyclo-alkynylcarbonyloxy group, an arylcarbonyloxy group, a heterocyclyl-carbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoyl-amino group, a mono- or di-alkoxycarbonylamino group, a mono- or di-arylcarbonylamino group, an alkylsulfinylamino group, an alkyl-sulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cyclo-alkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cyclo-alkenylsulfonyl group, a cycloalkynylsulfonyl group, an arylsulfonyl group, and a heterocyclylsulfonyl group, wherein each substituent may optionally be further substituted by these substituents.

Examples of the optionally substituted benzene ring of the present invention include a benzene ring which may optionally be substituted by 1-5 substituents selected from the group consisting of a halogen atom, a nitro group, a cyano group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyl-oxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group wherein each substituent may optionally be further substituted by these substituents.

Moreover, examples of the optionally substituted benzene ring include a benzene ring substituted with an alkylene group to form an annelated carbocycle together with the carbon atoms to which they are attached, and also includes a benzene ring substituted with an alkenylene group to form an annelated carbocycle such as a fused benzene ring together with the carbon atoms to which they are attached.

Preferable examples of the optionally substituted unsaturated monocyclic heterocyclic ring include an unsaturated monocyclic heterocyclic ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted unsaturated fused heterobicyclic ring include an unsaturated fused heterobicyclic ring which may optionally be substituted by 1-3 substituents independently selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cyclo-alkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted benzene ring include a benzene ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, an alkylene group, an alkyleneoxy group, an alkylenedioxy group, and an alkenylene group.

In another preferable embodiment of the present invention, the optionally substituted unsaturated monocyclic heterocyclic ring is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group;

the optionally substituted unsaturated fused heterobicyclic ring is an unsaturated fused heterobicyclic ring which may optionally be substituted by 1-3 substituents selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkanoyl group, an alkylsulfonylamino group, a phenyl group, a phenoxy group, a phenylsulfonylamino group, phenylsulfonyl group, a heterocyclyl group, and an oxo group; and the optionally substituted benzene ring is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxy group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, an oxo group, a carbamoyl group, and a mono- or di-alkylcarbamoyl group.

In a preferable embodiment, the optionally substituted unsaturated monocyclic heterocyclic ring is an unsaturated monocyclic heterocyclic ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is an unsaturated fused heterobicyclic ring which may optionally be substituted by 1-3 substituents independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxy group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In another preferable embodiment, (1) Ring A is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

(2) Ring A is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group, and Ring B is an unsaturated monocyclic heterocyclic ring or an unsaturated fused heterobicyclic ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group; or (3) Ring A is an unsaturated fused heterobicyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In a more preferable embodiment of the present invention, Ring A and Ring B are (1) Ring A is an unsaturated monocyclic heterocyclic ring which may optionally be substituted by a halogen atom, a lower alkyl group, a halo-lower alkyl group, a lower alkoxy group, or an oxo group, and Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mono- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group;

(2) Ring A is a benzene ring which may optionally be substituted by a halogen atom, a lower alkyl group, a halo-lower alkyl group, a lower alkoxy group, a phenyl group, or a lower alkenylene group, and Ring B is (a) an unsaturated monocyclic heterocyclic ring which may optionally be substituted by a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, a mono- or di-lower alkylamino group, or a carbamoyl group; or a heterocyclyl group optionally substituted by a halogen atom, a cyano group, a lower alkyl group, a halo-lower alkyl group, a lower alkoxy group, a mono- or di-lower alkylamino group or a carbamoyl group; (b) an unsaturated fused heterobicyclic ring which may optionally be substituted by a group selected from a halogen atom, cyano group, a lower alkyl group, a halo-lower alkyl group, a phenyl-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (3) Ring A is an unsaturated fused heterobicyclic ring which may optionally be substituted by a halogen atom, a lower alkyl group, a halo-lower alkyl group, a lower alkoxy group, or an oxo group, and Ring B is (a) a benzene ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; (b) an unsaturated monocyclic heterocyclic ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group.

In another more preferable embodiment, Y is —CH$_2$— and is linked at the 3-position of Ring A, with respect to X being the 1-position, Ring A is a benzene ring which is substituted by 1-3 substituents selected from the group consisting of a lower alkyl group, a halo-lower alkyl group, a halogen atom, a lower alkoxy group, a phenyl group, and a lower alkenylene group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxy phenyl group, a lower alkylenedioxyphenyl group, a lower alkyleneoxy phenyl group, a mono- or di-lower alkylaminophenyl group, a carbamoyl phenyl group, a mono- or di-lower alkylcarbamoylphenyl group, a heterocyclyl group, a haloheterocyclyl group, a cyanoheterocyclyl group, a lower alkylheterocyclyl group, a lower alkoxyheterocyclyl group, a mono- or di-lower alkylaminoheterocycyclyl group, a carbamoylheterocyclyl group, and a mono- or di-lower alkylcarbamoyl group.

In another more preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is a benzene ring which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, a cyanoheterocyclyl group, a lower alkylheterocyclyl group, and a lower alkoxyheterocyclyl group.

Further, in another preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxyphenyl group, a heterocyclyl group, a haloheterocyclyl group, a cyanoheterocyclyl group, a lower alkylheterocyclyl group, and a lower alkoxyheterocyclyl group.

In a more preferable embodiment of the present invention, X is a carbon atom and Y is —CH$_2$—.

Further, in another preferable embodiment, Ring A and Ring B are:

(1) Ring A is a benzene ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, a phenyl group, and a lower alkenylene group, and Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group, a halo-lower alkoxy group, or a carbamoyl group; a heterocyclyl group optionally substituted by a halogen atom, a cyano group, a lower alkyl group, a halo-lower alkyl group, a lower alkoxy group, a halo-lower alkoxy group or a carbamoyl group; and an oxo group, (2) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, and Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; a lower alkylene group, (3) Ring A is an unsaturated monocyclic heterocyclic ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group;

(4) Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group, or (5) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group.

In another preferable embodiment of the present invention, Y is linked at the 3-position of Ring A, with respect to X being the 1-position, Ring A is a benzene ring which may optionally be substituted by a halogen atom, a lower alkyl group optionally substituted by a halogen atom, a lower alkoxy group, or a phenyl group, and Ring B is an unsaturated monocyclic heterocyclic ring or an unsaturated fused heterobicyclic ring which may optionally be substituted by 1-3 substituents, independently selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and an oxo group.

In another more preferable embodiment of the present invention, Y is linked at the 3-position of Ring A, with respect to X being the 1-position, Ring A is an unsaturated monocyclic heterocyclic ring which may optionally be substituted by a substituent selected from a halogen atom, a lower alkyl group, and an oxo group, and Ring B is a benzene ring which may optionally be substituted by a substituent selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and a lower alkylene group.

Preferable examples of unsaturated monocyclic heterocyclic ring include a 5- or 6-membered unsaturated heterocyclic ring containing 1 or 2 hetero atoms independently selected from a nitrogen atom, an oxygen atom, and a sulfur atom. More specifically, preferred are furan, thiophene, oxazole, isoxazole, triazole, tetrazole, pyrazole, pyridine, pyrimidine, pyrazine, dihydroisoxazole, dihydropyridine, and thiazole. Preferable unsaturated fused heterobicyclic ring includes a 9- or 10-membered unsaturated fused heterocyclic ring containing 1 to 4 hetero atoms independently selected from a nitrogen atom, an oxygen atom, and a sulfur atom. More specifically, preferred are indoline, isoindoline, benzothiazole, benzoxazole, indole, indazole, quinoline, isoquinoline, benzothiophene, benzofuran, thienothiophene, and dihydroisoquinoline.

In a more preferred embodiment of the present invention, Ring A is a benzene ring which may optionally be substituted by a substituent selected from the group consisting of a halogen atom, a lower alkyl group, a halo-lower alkyl group, a lower alkoxy group, and a phenyl group, and Ring B is a heterocyclic ring selected from the group consisting of thiophene, furan, benzofuran, benzothiophene, and benzothiazole, wherein the heterocyclic ring may optionally be substituted by a substituent selected from the following group: a halogen atom, a cyano group, a lower alkyl group, a halo-lower alkyl group, a phenyl-lower alkyl group, a lower alkoxy group, a halo-lower alkoxy group, a phenyl group, a halophenyl group, a lower alkylphenyl group, a lower alkoxyphenyl group, a thienyl group, a halothienyl group, a pyridyl group, a halopyridyl group, and a thiazolyl group.

In yet another preferred embodiment, Y is —$CH_2$—, Ring A is an unsaturated monocyclic heterocyclic ring or an unsaturated fused heterobicyclic ring selected from the group consisting of thiophene, dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic ring may optionally substituted by a substituent selected from the following group: a halogen atom, a lower alkyl group, and an oxo group, and Ring B is a benzene ring which may optionally be substituted by a substituent selected from the following group: a halogen atom, a lower alkyl group, a halo-lower alkyl group, a lower alkoxy group, and a halo-lower alkoxy group.

In a further preferred embodiment of the present invention, Ring A is a benzene ring which is substituted by a halogen atom or a lower alkyl group, and Ring B is thienyl group which is substituted by phenyl group or a heterocyclyl group in which said phenyl group and heterocyclyl group is substituted by 1-3 substituents selected from a halogen atom, a cyano group, a lower alkyl group, a halo-lower alkyl group, a lower alkoxy group, and a halo-lower alkoxy group.

Further, in another aspect of the present invention, preferable examples of the compound of the formula I include a compound wherein Ring A is

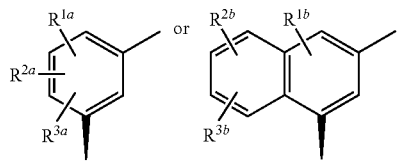

wherein $R^{1a}$, $R^{2a}$, $R^{3a}$, $R^{1b}$, $R^{2b}$, and $R^{3b}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group, or a phenylsulfonyl group, and Ring B is

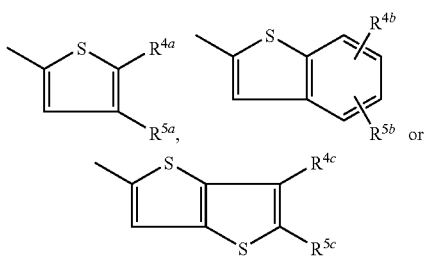

wherein $R^{4a}$ and $R^{5a}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, a mono- or di-alkylamino group, a carbamoyl group, or a mono- or di-alkylcarbamoyl group; or a heterocyclyl group optionally substituted by a halogen atom, a cyano group, an alkyl group, a haloalkyl group, an alkoxy group, a haloalkoxy group, a carbamoyl group, or a mono- or di-alkylcarbamoyl group, or $R^{4a}$ and $R^{5a}$ are bonded to each other at the terminals thereof to form an alkylene group; and $R^{4b}$, $R^{5b}$, $R^{4c}$ and $R^{5c}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, a methylenedioxy group, an ethyleneoxy group, or a mono- or di-alkylamino group; or a heterocyclyl group optionally substituted by a halogen atom, a cyano group, an alkyl group, a haloalkyl group, an alkoxy group or a haloalkoxy group.

More preferred is a compound wherein $R^{1a}$, $R^{2a}$, $R^{3a}$, $R^{1b}$, $R^{2b}$, and $R^{3b}$ are each independently a hydrogen atom, a halogen atom, a lower alkyl group, a halo-lower alkyl group, a lower alkoxy group, or a phenyl group;

$R^{4a}$ and $R^{5a}$ are each independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, or $R^{4a}$ and $R^{5a}$ are bonded to each other at the terminals thereof to form a lower alkylene group; and $R^{4b}$, $R^{5b}$, $R^{4c}$ and $R^{5c}$ are each independently a hydrogen atom, a halogen atom, a lower alkyl group, a halo-lower alkyl group, a lower alkoxy group, or a halo-lower alkoxy group.

Further preferred is a compound in which Ring B is

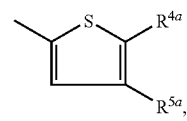

wherein $R^{4a}$ is a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, or $R^{4a}$ and $R^{5a}$ are bonded to each other at the terminals thereof to form a lower alkylene group.

Further more preferred is a compound in which Ring A is

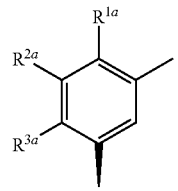

wherein $R^{1a}$ is a halogen atom, a lower alkyl group, or a lower alkoxy group, and $R^{2a}$ and $R^{3a}$ are hydrogen atoms; and Ring B is

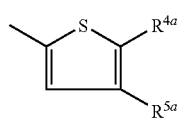

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, and Y is —$CH_2$—.

In more preferable embodiment, $R^{4a}$ is a phenyl group optionally substituted by a halogen atom, a cyano group, a lower alkyl group, a halo-lower alkyl group, a lower alkoxy group, or a halo-lower alkoxy group; or a heterocyclyl group optionally substituted by a halogen atom, a cyano group, a lower alkyl group, or a lower alkoxy group.

In another preferable embodiment of the present invention, a preferable compound can be represented by the following formula IA:

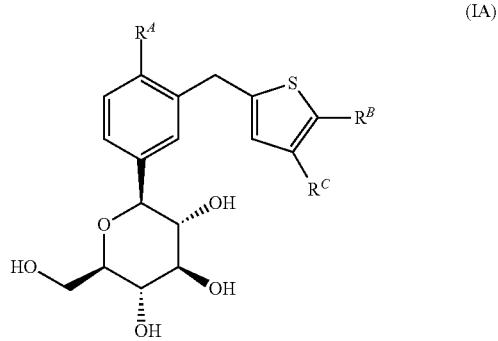

(IA)

wherein $R^A$ is a halogen atom, a lower alkyl group or a lower alkoxy group; $R^B$ is a phenyl group optionally substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group optionally substituted by 1-3 substituents selected from a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; and $R^C$ is hydrogen atom; or $R^B$ and $R^C$ taken together are a fused benzene ring which may be substituted by a halogen atom, a lower alkyl group, a halo-lower alkyl group, a lower alkoxy group or a halo-lower alkoxy group.

In a preferable embodiment, $R^A$ is a halogen atom or a lower alkyl group, $R^C$ is hydrogen atom, and $R^B$ is phenyl group substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group. The chemical structure of such compounds are represented by the following formula (IA'):

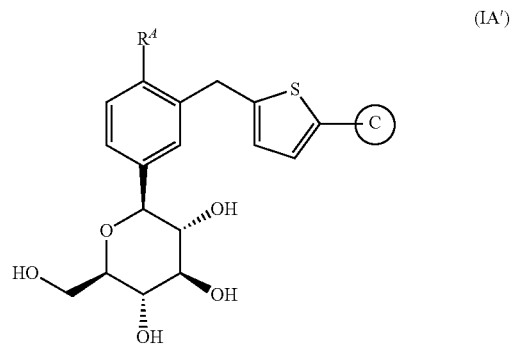

(IA')

wherein $R^A$ is a halogen atom, or a lower alkyl group, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

In a more preferable embodiment, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

Among them, a compound in which Ring C is a phenyl group substituted by a halogen atom, a cyano group, a lower alkyl group, a halo-lower alkyl group, a lower alkoxy group or a halo-lower alkoxy group; or a heterocyclyl group substituted by a halogen atom, a cyano group, a lower alkyl group, or a lower alkoxy group is preferred.

A preferred heterocyclyl group includes a 5- or 6-membered heterocyclyl group containing 1 or 2 hetero atoms independently selected from the group consisting of a nitrogen atom, an oxygen atom, and a sulfur atom, or a 9- or 10-membered heterocyclyl group containing 1 to 4 hetero atoms independently selected from the group consisting of a nitrogen atom, an oxygen atom, and a sulfur atom. Specifically, a thienyl group, a pyridyl group, a pyrimidyl group, a pyrazinyl group, pyrazolyl group, a thiazolyl group, a quinolyl group, a tetrazolyl group and an oxazolyl group are preferred.

In a further preferable embodiment, Ring C is a phenyl group substituted by a halogen atom or a cyano group, or a pyridyl group substituted by a halogen atom.

In another preferable embodiment of the present invention, preferred is a compound in which Ring A is

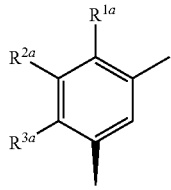

wherein $R^{1a}$ is a halogen atom, a lower alkyl group, or a lower alkoxy group, and $R^{2a}$ and $R^{3a}$ are hydrogen atoms; and Ring B is

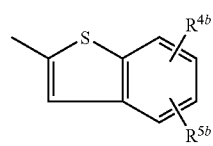

wherein $R^{4b}$ and $R^{5b}$ are each independently a hydrogen atom, a halogen atom, a lower alkyl group, a halo-lower alkyl group, a lower alkoxy group, or a halo-lower alkoxy group.

In another aspect of the present invention, preferable examples of the compound I include a compound represented by the following formula IB:

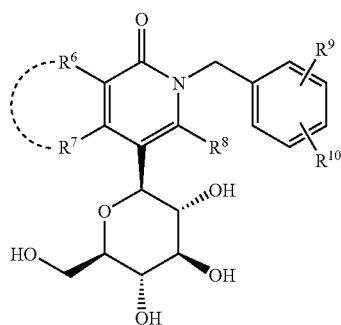

(IB)

wherein $R^8$, $R^9$ and $R^{10}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group; and a group represented by:

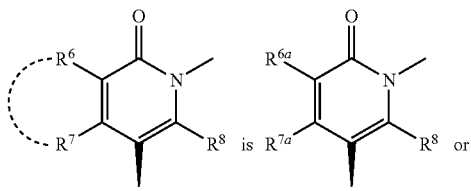

wherein $R^{6a}$ and $R^{7a}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group and $R^{6b}$ and $R^{7b}$ are each independently a hydrogen atom, a halogen atom, an alkyl group, a haloalkyl group, or an alkoxy group.

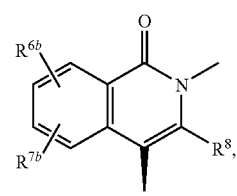

Among the compounds represented by the formula IB, more preferred is a compound in which $R^8$, $R^9$ and $R^{10}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, and a group represented by:

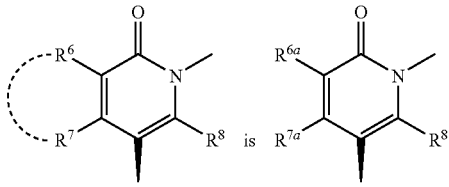

wherein $R^{6a}$, $R^{7a}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, or a group represented by:

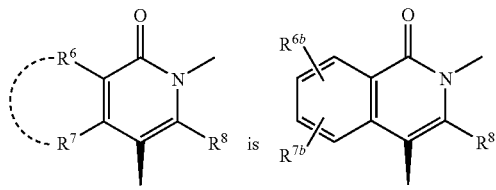

wherein $R^{6b}$ and $R^{7b}$ are each independently a hydrogen atom, a halogen atom, a lower alkyl group, a halo-lower alkyl group, or a lower alkoxy group.

In another aspect of the present invention, preferable examples of the compound I include a compound represented by the following formula IC:

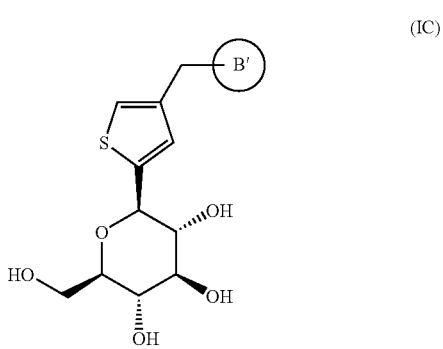

(IC)

wherein Ring B' is an optionally substituted benzene ring, an optionally substituted unsaturated monocyclic heterocyclic ring, or an optionally substituted unsaturated fused heterobicyclic ring.

Preferable examples of Ring B' include a benzene ring and a heterocyclic ring, both of which may have a substituent(s) selected from the group consisting of a halogen atom; a cyano group; a lower alkyl group optionally substituted by a halogen atom; a lower alkoxy group optionally substituted by a halogen atom; a lower alkanoyl group; a mono- or di-lower alkylamino group; a lower alkoxycarbonyl group; a carbamoyl group; a mono- or di-lower alkylcarbamoyl group; a phenyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; a heterocyclyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; an alkylene group; and an oxo group.

More preferable examples of Ring B' include a benzene ring which may be substituted by a substituent selected from the group consisting of a halogen atom; a cyano group; a lower alkyl group optionally substituted by a halogen atom; a lower alkoxy group optionally substituted by a halogen atom; a mono- or di-lower alkylamino group; a phenyl group optionally substituted by a halogen atom, a cyano group, a lower alkyl group optionally substituted by a halogen atom, a lower alkoxy group optionally substituted by a halogen atom; a heterocyclyl group optionally substituted by a halogen atom, a cyano group, a lower alkyl group optionally substituted by a halogen atom, a lower alkoxy group optionally substituted by a halogen atom.

Preferred compound of the present invention may be selected from the following group:
1-(β-D-glucopyranosyl)-4-chloro-3-(6-ethylbenzo[b]thiophen-2-ylmethyl)benzene;
1-(β-D-glucopyranosyl)-4-chloro-3-[5-(5-thiazolyl)-2-thienylmethyl]benzene;
1-(β-D-glucopyranosyl)-4-chloro-3-(5-phenyl-2-thienylmethyl)benzene;
1-(β-D-glucopyranosyl)-4-methyl-3-[5-(4-fluorophenyl)-2-thienylmethyl]benzene;
1-(β-D-glucopyranosyl)-4-chloro-3-[5-(2-pyrimidinyl)-2-thienylmethyl]benzene;
1-(β-D-glucopyranosyl)-4-methyl-3-[5-(2-pyrimidinyl)-2-thienylmethyl]benzene;
1-(β-D-glucopyranosyl)-4-chloro-3-[5-(3-cyanophenyl)-2-thienylmethyl]benzene;
1-(β-D-glucopyranosyl)-4-chloro-3-[5-(4-cyanophenyl)-2-thienylmethyl]benzene;
1-(β-D-glucopyranosyl)-4-methyl-3-[5-(6-fluoro-2-pyridyl)-2-thienylmethyl]benzene;
1-(β-D-glucopyranosyl)-4-chloro-3-[5-(6-fluoro-2-pyridyl)-2-thienylmethyl]benzene;
1-(β-D-glucopyranosyl)-4-methyl-3-[5-(3-difluoromethylphenyl)-2-thienylmethyl]benzene;
1-(β-D-glucopyranosyl)-4-methyl-3-[5-(3-cyanophenyl)-2-thienylmethyl]benzene;
1-(β-D-glucopyranosyl)-4-methyl-3-[5-(4-cyanophenyl)-2-thienylmethyl]benzene;
1-(β-D-glucopyranosyl)-4-chloro-3-[5-(6-fluoro-3-pyridyl)-2-thienylmethyl]benzene;
1-(β-D-glucopyranosyl)-4-fluoro-3-(5-(3-cyanophenyl)-2-thienylmethyl)benzene;
the pharmaceutically acceptable salt thereof; and the prodrug thereof.

Particularly preferred compounds of the present invention include:
1-(β-D-glucopyranosyl)-4-methyl-3-[5-(3-cyano-phenyl)-2-thienylmethyl]benzene, or a pharmaceutically acceptable salt thereof, or a prodrug thereof;
1-(β-D-glucopyranosyl)-4-methyl-3-[5-(4-cyano-phenyl)-2-thienylmethyl]benzene, or a pharmaceutically acceptable salt thereof, or a prodrug thereof;
1-(β-D-glucopyranosyl)-4-methyl-3-[5-(4-fluoro-phenyl)-2-thienylmethyl]benzene, or a pharmaceutically acceptable salt thereof, or a prodrug thereof;
1-(β-D-glucopyranosyl)-4-chloro-3-[5-(3-cyano-phenyl)-2-thienylmethyl]benzene, or a pharmaceutically acceptable salt thereof, or a prodrug thereof;
1-(β-D-glucopyranosyl)-4-methyl-3-[5-(6-fluoro-2-pyridyl)-2-thienylmethyl]benzene, or a pharmaceutically acceptable salt thereof, or a prodrug thereof;
1-(β-D-glucopyranosyl)-4-chloro-3-[5-(6-fluoro-2-pyridyl)-2-thienylmethyl]benzene, or a pharmaceutically acceptable salt thereof, or a prodrug thereof;
1-(β-D-glucopyranosyl)-4-chloro-3-[5-(6-fluoro-3-pyridyl)-2-thienylmethyl]benzene, or a pharmaceutically acceptable salt thereof, or a prodrug thereof; and
1-(β-D-glucopyranosyl)-4-fluoro-3-(5-(3-cyanophenyl)-2-thienylmethyl)benzene, or a pharmaceutically acceptable salt thereof, or a prodrug thereof.

Abbreviations used in the specification, particularly the Schemes and Examples, are as follows BF$_3$OEt$_2$=Boron Trifluoride Diethyl Etherate
DCE=Dichloroethane
DCM=Dichloromethane
DMAP=4-(N,N-Dimethylamino)pyridine
DMF=N,N-Dimethylformamide
Et$_3$SiH=Triethyl Silane
IPA=Isopropyl Alcohol
MeOH=Methanol
MTBE=Methyl-t-butyl Ether
NMM=N-methyl-morpholine
TEA=Triethylamine
THF=Tetrahydrofuran In general, for commercial use it is preferred that a product exhibit good handling qualities. Additionally, for commercial use, it is preferred that the product is produced in a substantially pure and crystalline form, to enable formulations to meet exacting pharmaceutical requirements and specifications. Further, for commercial scale preparation, it is preferred that the product be in a form that is readily filterable and easily dried. Finally, it is preferred that the product be stable for extended periods of time without the need for specialized storage conditions.

As used herein, unless otherwise noted, the term "isolated form" shall mean that the compound is present in a form which is separate from any solid mixture with another compound(s), solvent system or biological environment. In an embodiment, the compound of formula (I), the compound of formula (I-S), the compound of formula (I-K), the crystalline form of the compound of formula (I-S) and/or the crystalline form of the compound of formula (I-K) is present and/or prepared in an isolated form.

As used herein, unless otherwise noted, the term "substantially pure" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the compound of formula (I), the compound of formula (I-S), the compound of formula (I-K), the crystalline form of the compound of formula (I-S) and/or the crystalline form of the compound of formula (I-K) is present and/or prepared in substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the compound of formula (I), the compound of formula (I-S), the compound of formula (I-K), the crystalline form of the compound of formula (I-S) and/or the crystalline form of the compound of formula (I-K) is present and/or prepared in a form which is substantially free of corresponding salt forms.

In an embodiment, the present invention is directed to a process for the preparation of a compound of formula (I), wherein the compound of formula (I) is substantially pure. In another embodiment, the present invention is directed to a process for the preparation of a compound of formula (I-S), wherein the compound of formula (I-S) is substantially pure. In another embodiment, the present invention is directed to a process for the preparation of a compound of formula (I-K), wherein the compound of formula (I-K) is substantially pure.

In an embodiment, the present invention is directed to a process for the preparation of a compound of formula (I), wherein the compound of formula (I) is substantially free of corresponding salt forms. In another embodiment, the present invention is directed to a process for the preparation of a compound of formula (I-S), wherein the compound of formula (I-S) is substantially free of corresponding salt forms. In another embodiment, the present invention is directed to a process for the preparation of a compound of formula (I-K), wherein the compound of formula (I-K) is substantially free of corresponding salt forms.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compound of formula (I) of the present invention exhibits an excellent inhibitory activity against sodium-dependent glucose transporter, and an excellent blood glucose lowering effect. Therefore, the compound of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the compound of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

The compound of formula (I) of the present invention or a pharmaceutically acceptable salt thereof may be administered either orally or parenterally, and can be used in the form of a suitable pharmaceutical preparation. Suitable pharmaceutical preparation for oral administration includes, for example, solid preparation such as tablets, granules, capsules, powders, etc., or solution preparations, suspension preparations, or emulsion preparations, etc. Suitable pharmaceutical preparation for parenteral administration includes, for example, suppositories; injection preparations and intravenous drip preparations using distilled water for injection, physiological saline solution or aqueous glucose solution; or inhalant preparations.

The dosage of the present compound of formula (I) or a pharmaceutically acceptable salt thereof may vary according to the administration routes, ages, body weight, conditions of a patient, or kinds and severity of a disease to be treated, and it is usually in the range of about 0.01 to 300 mg/kg/day, or any range therein, preferably in the range of about 0.1 to 50 mg/kg/day, or any range therein, preferably in the range of about 0.1 to 30 mg/kg/day, or any range therein.

The compound of the formula I may be used, if necessary, in combination with one or more of other antidiabetic agents, one or more agents for treating diabetic complications, and/or one or more agents for treatment of other diseases. The present compound and these other agents may be administered in the same dosage form, or in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Concrete examples thereof are biguanide compounds, sulfonylurea compounds, α-glucosidase inhibitors, PPARγ agonists (e.g., thiazolidinedione compounds), PPARα/γ dual agonists, dipeptidyl peptidase IV (DPP4) inhibitors, mitiglinide compounds, and/or nateglinide compounds, and insulin, glucagon-like peptide-1 (GLP-1), PTP1B inhibitors, glycogen phosphorylase inhibitors, RXR modulators, and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula I may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

One skilled in the art will recognize that, where not otherwise specified, the reaction step(s) is performed under suitable conditions, according to known methods, to provide the desired product.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-,2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize that in any of the processes described herein, reactive substituents on the compounds of formula (I), such as hydroxy groups, oxo groups, carboxy groups, and the like, are preferably protected and subsequently de-protected, according to known methods, at suitable points along the synthesis route.

The present invention is directed to a process for the preparation of compounds of formula (I) as outlined in Scheme 1, below.

Scheme 1

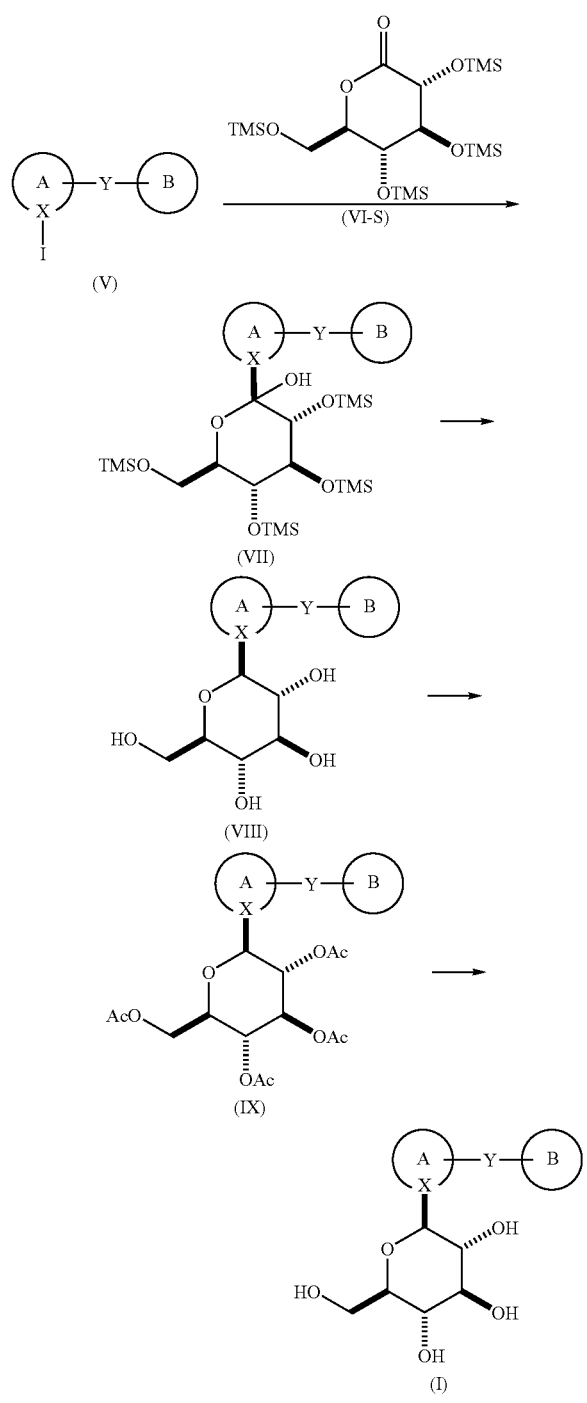

Accordingly, a suitably substituted compound of formula (V), a known compound or compound prepared by known methods, is reacted with a compound of formula (VI-S), a known compound or compound prepared by known methods; wherein the compound of formula (VI-S) is preferably present in an amount in the range of from about 1.0 to about 2.0 molar equivalents, or any range therein, more preferably in an amount in the range of from about 1.0 to about 1.25 molar equivalents, or any range therein, most preferably about 1.2 molar equivalents;

in the presence of an alkyl lithium such as trimethylsilylmethyl lithium, mesityl lithium (i.e. 2,4,6-trimethylphenyl lithium), triethylsilylmethyl lithium, preferably trimethylsilylmethyl lithium and the like, wherein the alkyl lithium is preferably present in an amount in the range of from about 2.0 to about 3.0 molar equivalents, or any range therein, more preferably in an amount in the range of from about 2.0 to about 2.5 molar equivalents, or any range therein, most preferably about 2.0 molar equivalents;

in an organic solvent such as THF, hexane, pentane, MTBE, dioxane, and the like, preferably THF; at a temperature in the range of from about 0° C. to about −78° C., or any range therein, preferably at about −40° C.; to yield the corresponding compound of formula (VII).

Preferably, the alkyl lithium is added to a mixture of the compound of formula (V) and the compound of formula (VI-S).

One skilled in the art will recognize that the compound of formula (V) may alternatively be reacted (as described above) with a compound of formula (VI-S), wherein the trimethylsilyl (TMS) substituents are substituted with one or more suitably selected alternate silyl groups such as triethylsilyl, phenyldimethylsilyl, and the like.

The compound of formula (VII) is reacted with $BF_3OEt_2$ in the presence of a suitably selected trialkylsilane such as $Et_3SiH$, and the like; wherein the $BF_3OEt_2$ is preferably present in an amount in the range of from about 2.0 to about 10.0 molar equivalents, or any range therein, more preferably, in an amount in the range of from about 2.0 to about 6.0 molar equivalents, most preferably about 3.0 molar equivalents; and wherein the trialkylsilane is preferably present in an amount in the range of from about 2.0 to about 10.0 molar equivalents, or any range therein, more preferably, in an amount in the range of from about 2.0 to about 6.0 molar equivalents, or any range therein, most preferably about 3.0 molar equivalent; preferably, wherein the ratio of the $BF_3OEt_2$ to the trialkylsilane is about 1:1;

in an organic solvent such as DCM, DCE, acetonitrile, toluene, and the like, or in a mixture of said organic solvents, preferably in DCM; preferably at a temperature in the range of from about 0° C. to about −40° C., or any range therein, more preferably at about −30° C.; to yield the corresponding compound of formula (VIII).

One skilled in the art will recognize that the compound of formula (VII) may alternatively be de-protected according to known methods (for example by reacting with a suitably selected acid such as HCl, and the like), to yield the corresponding compound of formula (X)

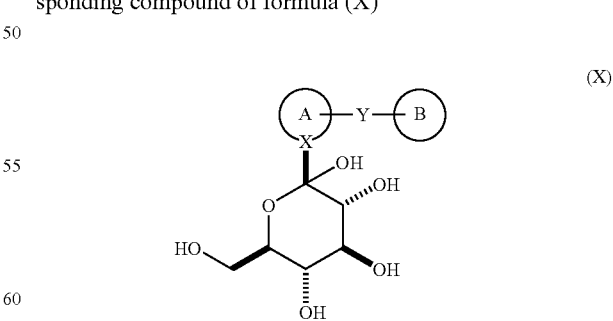

which is then reacted with $BF_3OEt_2$ in the presence of a suitably selected trialkylsilane such as $Et_3SiH$, and the like; wherein the $BF_3OEt_2$ is preferably present in an amount in the range of from about 2.0 to about 10.0 molar equivalents, or any range therein, more preferably, in an amount in the range of from about 2.0 to about 6.0 molar equivalents, most preferably about 3.0 molar equivalents; and wherein the trialkylsilane is preferably present in an amount in the range of from about 2.0 to about 10.0 molar equivalents, or any range therein, more preferably, in an amount in the range of from about 2.0 to about 6.0 molar equivalents, or any range therein, most preferably about 3.0 molar equivalent; preferably, wherein the ratio of the BF$_3$OEt$_2$ to the trialkylsilane is about 1:1;

in an organic solvent such as DCM, DCE, acetonitrile, toluene, and the like, or in a mixture of said organic solvents, preferably in DCM; preferably at a temperature in the range of from about 0° C. to about −40° C., or any range therein, more preferably at about −30° C.; to yield the corresponding compound of formula (VIII).

The compound of formula (VIII) is reacted with acetic anhydride or acetyl chloride, preferably acetic anhydride, a known compound; wherein the acetic anhydride is preferably present in an amount in the range of from about 4.0 to about 6.0 molar equivalents, or any range therein, more preferably in an amount in the range of from about 4.5 to about 5.0 molar equivalents, or any range therein, most preferably about 5.0 molar equivalents;

in the presence of an organic base such as N-methylmorpholine (NMM), TEA, pyridine, and the like, preferably NMM; wherein the organic base is preferably present in an amount in the range of from about 3.0 to about 6.0 molar equivalents, or any range therein, more preferably about 5.0 molar equivalents; optionally in the presence of a catalyst such as DMAP, and the like; preferably in the presence of a catalytic amount of DMAP;

neat or in an organic solvent such as THF, acetonitrile, and the like, preferably, THF; preferably, at a temperature in the range of from about −10° C. to about room temperature, or any range therein, preferably at a temperature in the range of from about 0° C. to about room temperature; to yield the corresponding compound of formula (IX).

The compound of formula (IX) is preferably slurried or dissolved in a solvent, more preferably slurried; and then filtered, preferably filtered at an elevated temperature, to remove impurities and/or byproducts.

The compound of formula (IX) is de-protected according to known methods. For example, the compound of formula (IX) is reacted with a suitably selected base such as LiOH, NaOH, and the like, preferably LiOH; wherein the base is preferably present in an amount in the range of from about 0.1 to about 1.0 molar equivalent, or any range therein, more preferably from about 0.25 to about 0.5 molar equivalents, or any range therein, most preferably about 0.5 molar equivalents, (for example, a catalytic amount); in a mixture of water, THF and methanol, wherein the ratio of water:THF:methanol is preferably about 1:2:3; preferably at about room temperature; to yield the corresponding compound of formula (I).

The compound of formula (I) is preferably isolated and/or recrystallized, according to known methods.

In an embodiment, the present invention is directed to a process for the preparation of a compound of formula (I-S), as outlined in Scheme 2, below.

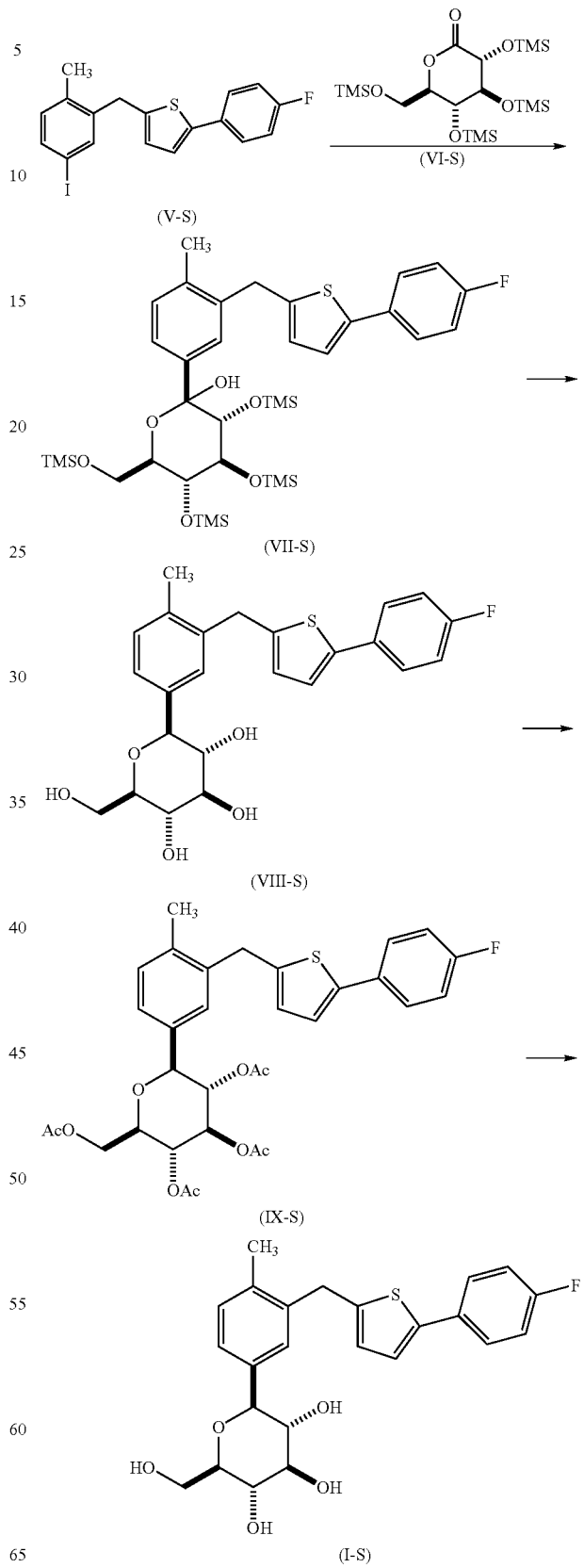

Accordingly, a suitably substituted compound of formula (V-S), a known compound or compound prepared by known methods, is reacted with a compound of formula (VI-S), a known compound or compound prepared by known methods; wherein the compound of formula (VI-S) is preferably present in an amount in the range of from about 1.0 to about 2.0 molar equivalents, or any range therein, more preferably in an amount in the range of from about 1.0 to about 1.25 molar equivalents, or any range therein, most preferably about 1.2 molar equivalents;

in the presence of an alkyl lithium such as trimethylsilylmethyl lithium, mesityl lithium (i.e. 2,4,6-trimethylphenyl lithium), triethylsilylmethyl lithium, preferably trimethylsilylmethyl lithium and the like, wherein the alkyl lithium is preferably present in an amount in the range of from about 2.0 to about 3.0 molar equivalents, or any range therein, more preferably in an amount in the range of from about 2.0 to about 2.5 molar equivalents, or any range therein, most preferably about 2.0 molar equivalents;

in an organic solvent such as THF, hexane, pentane, MTBE, dioxane, and the like, preferably THF; at a temperature in the range of from about 0° C. to about −78° C., or any range therein, preferably at about −40° C.; to yield the corresponding compound of formula (VII-S).

Preferably, the alkyl lithium is added to a mixture of the compound of formula (V-S) and the compound of formula (VI-S).

One skilled in the art will recognize that the compound of formula (V-S) may alternatively be reacted (as described above) with a compound of formula (VI-S), wherein the trimethylsilyl (TMS) substituents are substituted with one or more suitably selected alternate silyl groups such as triethylsilyl, phenyldimethylsilyl, and the like.

The compound of formula (VII-S) is reacted with $BF_3OEt_2$ in the presence of a suitably selected trialkylsilane such as $Et_3SiH$, and the like; wherein the $BF_3OEt_2$ is preferably present in an amount in the range of from about 2.0 to about 10.0 molar equivalents, or any range therein, more preferably, in an amount in the range of from about 2.0 to about 6.0 molar equivalents, most preferably about 3.0 molar equivalents; and wherein the trialkylsilane is preferably present in an amount in the range of from about 2.0 to about 10.0 molar equivalents, or any range therein, more preferably, in an amount in the range of from about 2.0 to about 6.0 molar equivalents, or any range therein, most preferably about 3.0 molar equivalent; preferably, wherein the ratio of the $BF_3OEt_2$ to the trialkylsilane is about 1:1;

in an organic solvent such as DCM, DCE, acetonitrile, toluene, and the like, or in a mixture of said organic solvents, preferably in DCM; preferably at a temperature in the range of from about 0° C. to about −40° C., or any range therein, more preferably at about −30° C.; to yield the corresponding compound of formula (VIII-S).

The compound of formula (VIII-S) is reacted with acetic anhydride or acetyl chloride, preferably acetic anhydride, a known compound; wherein the acetic anhydride is preferably present in an amount in the range of from about 4.0 to about 6.0 molar equivalents, or any range therein, more preferably in an amount in the range of from about 4.5 to about 5.0 molar equivalents, or any range therein, most preferably about 5.0 molar equivalents;

in the presence of an organic base such as N-methylmorpholine (NMM), TEA, pyridine, and the like, preferably NMM; wherein the organic base is preferably present in an amount in the range of from about 3.0 to about 6.0 molar equivalents, or any range therein, more preferably about 5.0 molar equivalents; optionally in the presence of a catalyst such as DMAP, and the like; preferably in the presence of a catalytic amount of DMAP;

neat or in an organic solvent such as THF, acetonitrile, and the like, preferably, THF; preferably, at a temperature in the range of from about −10° C. to about room temperature, or any range therein, preferably at a temperature in the range of from about 0° C. to about room temperature; to yield the corresponding compound of formula (IX-S).

The compound of formula (IX-S) is preferably slurried or dissolved in a solvent, more preferably slurried; and then filtered, preferably at an elevated temperature, to remove impurities and/or byproducts. Preferably, the mixture of the compound of formula (IX-S) in an organic solvent such as methanol, ethanol and the like, preferably methanol, is slurried or dissolved, preferably slurried, and then filtered, preferably at an elevated temperature, to remove impurities and/or byproducts.

The compound of formula (IX-S) is de-protected according to known methods. For example, the compound of formula (IX-S) is reacted with a suitably selected base such as LiOH, NaOH, and the like, preferably LiOH; wherein the base is preferably present in an amount in the range of from about 0.1 to about 1.0 molar equivalent, or any range therein, more preferably from about 0.25 to about 0.5 molar equivalents, or any range therein, most preferably about 0.5 molar equivalents, (for example, a catalytic amount); in a mixture of water, THF and methanol, wherein the ratio of water:THF: methanol is preferably about 1:2:3; preferably at about room temperature; to yield the corresponding compound of formula (I-S).

The compound of formula (I-S) is preferably recrystallized. In an embodiment, the compound of formula (I-S) is recrystallized according to the following process:

STEP A: the compound of formula (I-S) is dissolved in an organic solvent such as ethyl acetate, methanol, ethanol and the like, preferably ethyl acetate; then optionally filtered;

STEP B: the mixture of STEP A is heated to a temperature in the range of from about 25° C. to about 45° C., preferably to a temperature in the range of from about 30 to about 35° C.; then optionally filtered;

STEP C: to the mixture prepared in STEP B is added water, preferably about 1.0 to about 2.0 molar equivalents, more preferably about 1.5 molar equivalents;

STEP D: to the mixture prepared in STEP C is slowly added heptane (to initiate precipitation—i.e. the heptane acts as an anti-solvent), preferably an amount such that the final volume:volume ratio of ethyl acetate:heptane was in the range of from about 1:1 to about 1.5:1, more preferably about 1.2:1;

to yield a precipitate of the compound of formula (I-S); which precipitate is preferably isolated by filtration and then dried according to known methods.

Preferably, in the recrystallization of the compound of formula (I-S), after addition of the heptane, the resulting mixture is seeded with the desired polymorph of the compound of formula (I-S).

The present invention is further directed to a novel crystalline form of the compound of formula (I-S). The present invention is further directed to a novel crystalline form of the compound of formula (I-K).

One skilled in the art will recognize that several methods for characterizing crystalline forms exist, and the present invention is not intended to be limited by the methods chosen or the instrumentation used in characterizing the compounds of the present invention. For example, with regard to powder x-ray diffraction patterns, the diffraction peak intensities in the experimental patterns can vary, as is known in the art, primarily due to preferred orientation (non-random orientation of the crystals) in the prepared sample. As such, the scope of the present invention must be considered in light of the variability of characterization that is appreciated by those skilled in the art.

The present invention is further directed to a crystalline form of the compound of formula (I-S)

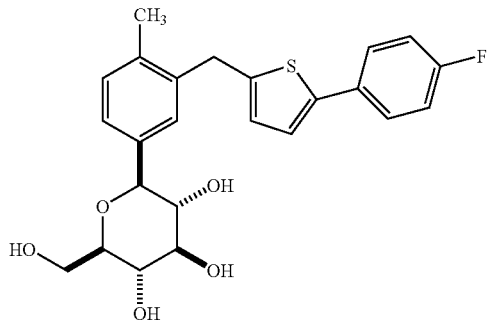

(I-S)

In an embodiment, the present invention is directed to a crystalline form of the compound of formula (I-S) prepared according to the recrystallization process as herein described. In another embodiment, the present invention is directed to a crystalline form of the compound of formula (I-S), prepared according to the following recrystallization process:

STEP A: dissolving a compound of formula (I-S) in ethyl acetate to yield mixture A; then optionally filtering mixture A;

STEP B: heating mixture A to a temperature in the range of from about 30° C. to about 35° C. to yield mixture B; then optionally filtering mixture B;

STEP C: adding about 1.5 molar equivalents of water to mixture B, to yield mixture C;

STEP D: slowly adding heptane to mixture C to yield a crystalline form of the compound of formula (I-S);

STEP E: isolating the crystalline form of the compound of formula (I-S) by filtration and drying.

The present invention is further directed to a novel crystalline form of a compound of formula (I-K)

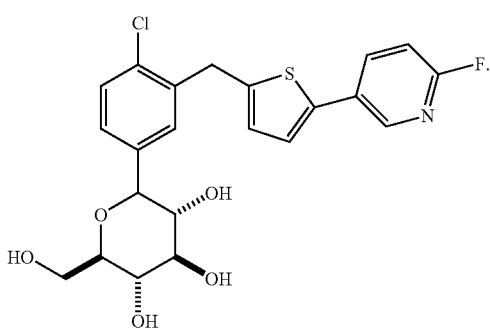

(I-K)

Figure 2:
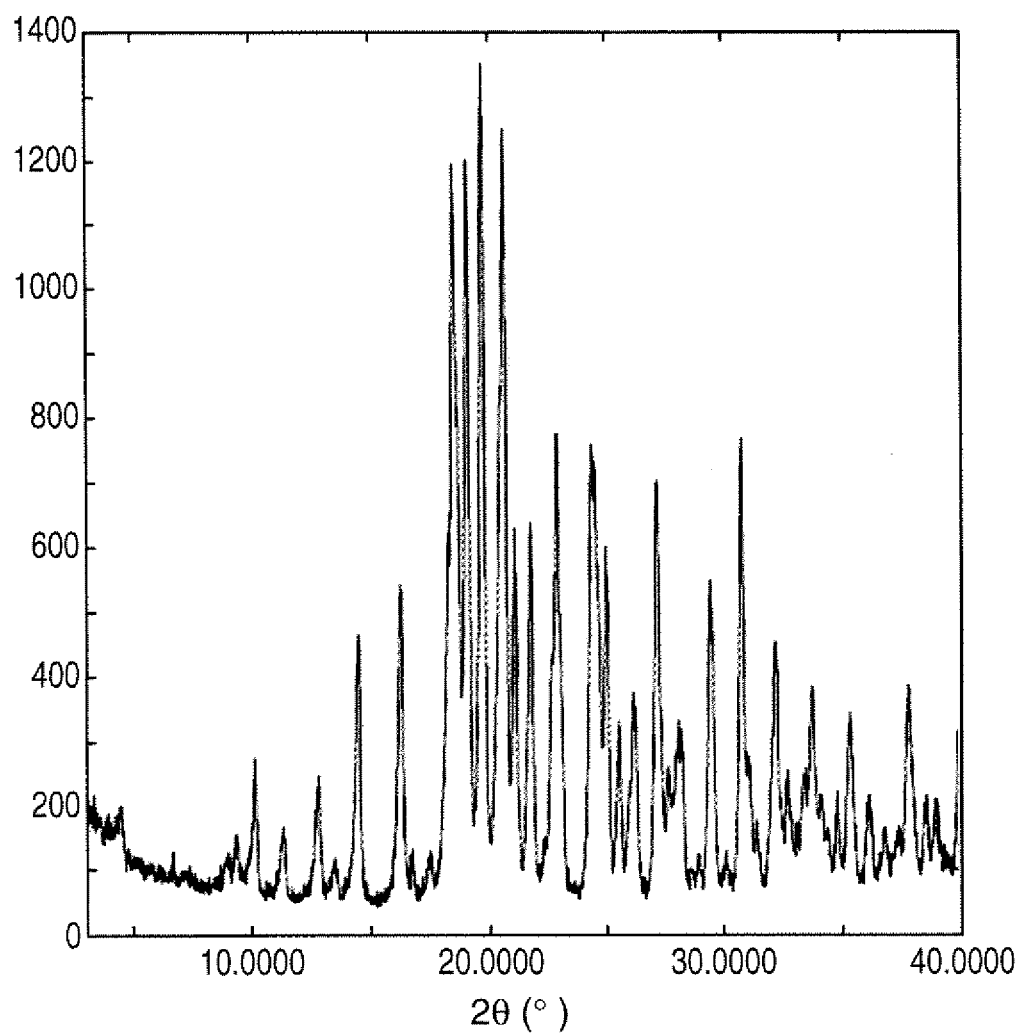
FIG. 2 illustrates a representative X-ray powder diffraction pattern of the crystalline form of the compound of formula (I-K), as measured on an RINT-ULTIMA3, Rigaku, Tokyo, Japan X-ray diffractometer.

An X-ray powder diffraction spectra was measured for a representative sample of the crystalline form of the compound of formula (I-K) using a RINT-ULTIMA3, Rigaku, Tokyo, Japan powder x-ray diffractometer, using CuK$_\alpha$ radiation and the following settings: (a) Scanning rate: 1.00 degree/minute; (b) Target: CuK$_\alpha$; (c) Voltage: 40 kV; (d) Current: 40 mA; (e) Scan range: from 3 to 40.0 degree; and (f) Sampling width: 0.0200 degree; as shown in FIG. 2.

Figure 3:
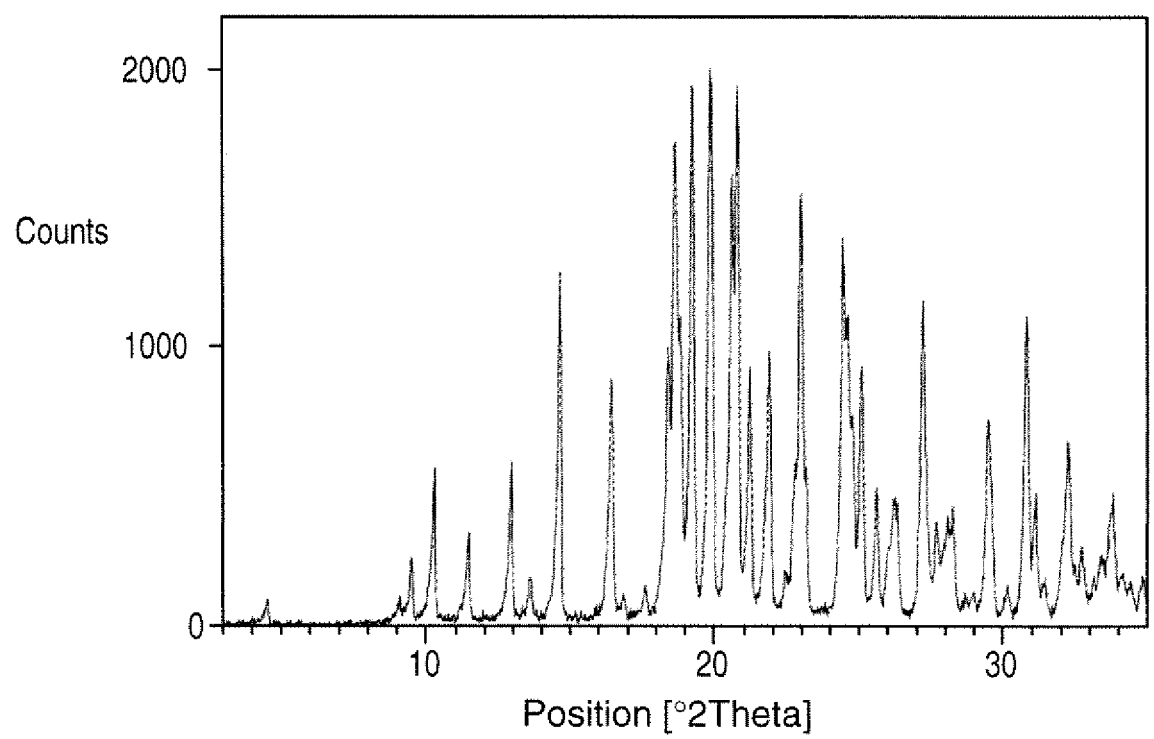
FIG. 3 illustrates a representative X-ray powder diffraction pattern of the crystalline form of the compound of formula (I-K), as measured on an X-ray diffractometer X'Pert Pro MPD, Philips X-ray diffractometer.

An X-ray powder diffraction pattern was further measured for a representative sample of the crystalline form of the compound of formula (I-K) using a Philips X'Pert Pro MPD powder X-ray diffractometer, using CuK$_\alpha$ radiation and the following settings: (a) Scanning rate: 0.207 degree/minute; (b) Target: CuK$_\alpha$; (c) Voltage: 45 kV; (d) Current: 40 mA; (e) Detector: X'celerator; (f) Scan range: from 3 to 35 degree; (g) Step size: 0.0165 degree; and (h) Time per step: 10.16 sec; as shown in FIG. 3.

Figure 4:
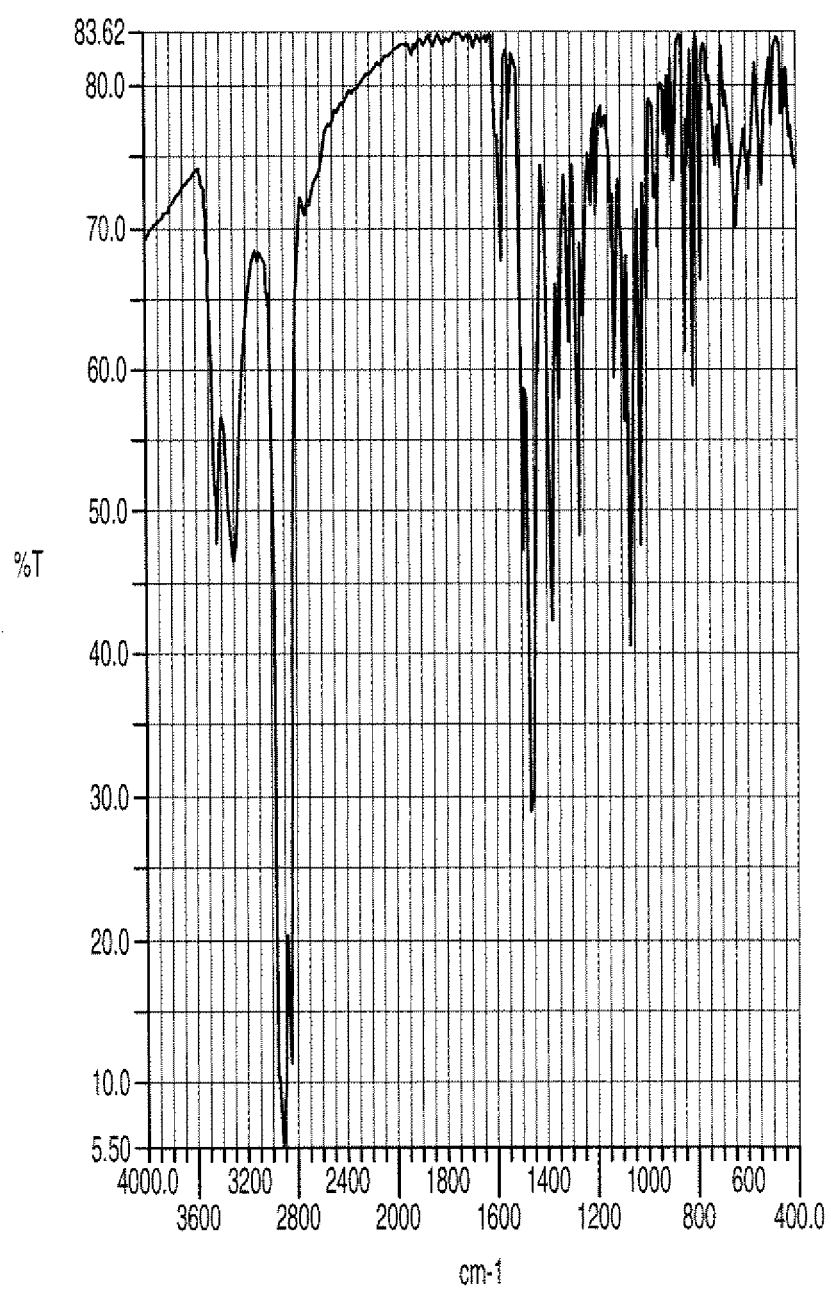
FIG. 4 illustrates a representative infra-red spectrum of the crystalline of the compound of formula (I-K) in mineral oil.

An Infra-red spectrum was measured for a representative samples of the crystalline form of the compound of formula (I-K) in mineral oil, as shown in FIG. 4, and also in a K—Br pellet, as shown in FIG. 5. In the infra-red spectra of the crystalline form of the compound (I-K) as shown in FIG. 4 and FIG. 5 which follow herein, the ordinate is the transmittance in % and the abscissa is the wavenumber in cm$^{-1}$.

The Fourier Transform Infra-red (FT-IR) spectrum of the crystalline form of the compound of formula (I-K) in mineral oil was recorded at a resolution of 4 cm$^{-1}$. The IR spectrum as shown in FIG. 4 represents the sum of 4 scans.

The IR spectrum shows the major characteristic absorption bands at 1492, 1463, 1377, 1268, 1065 and 1023 cm$^{-1}$, consistent with the functional groups present in the compound (I-K).

The Fourier Transform IR spectrum of the crystalline form of the compound (I-K) in a KBr pellet was recorded at a resolution of 4 cm$^{-1}$. The IR spectrum, as shown in FIG. 5, represents the sum of 64 scans. The IR spectrum shows the major characteristic absorption bands at 3431, 3321, 1493, 1269, 1065 and 1024 cm$^{-1}$.

Thermogravimetric analysis was completed on a representative sample of the crystalline form of the compound of formula (I-K). The methodology of the thermogravimetric analysis performed was as follows: 7.35 mg of the crystalline form of the compound (I-K) was weighed and transferred in an aluminum cell holder for TG-8120 (RIGAKU, Japan). The thermogravimetric (TG) thermal curve of the crystalline form of the compound of formula (I-K) was then determined at a heat rate of 5° C./minute, with a typical measuring range from ambient temperature to 200° C. The crystalline form of the compound of formula (I-K) was not been observed in the thermogravimetric analysis to exist in a hydrate or solvate form.

The present invention is further directed to a process for the preparation of the crystalline form of the compound (I-K) which process comprises forming a solution of the compound of formula (I-K) and precipitating the crystalline form from the solution. The crystalline form of the compound of formula (I-K) may be obtained from a solution of the compound of formula (I-K) in an appropriate solvent. Sometimes some impurities may act as crystallization inhibitors, and such impurities need to be removed using a conventional manner, such as silica gel column chromatography, as would be readily recognized by one skilled in the art. However, the crystalline of the compound of formula (I-K) may be obtained from compound of formula (I-K) containing some impurities.

The crystalline form of the compound of formula (I-K) may be prepared from a solution of the compound of formula (I-K) in a suitably selected solvent. Examples of suitable solvents include, but are not limited to, ketones (e.g., acetone, 2-butanone), esters (e.g., ethyl acetate, methyl acetate), alcohols (e.g., methanol, ethanol, i-propanol), and a mixture of these solvents. Particularly preferred solvents include, esters such as ethyl acetate. In some cases, an anti-solvent can be added to the solution of the compound of formula (I-K).

Examples of anti-solvents include alkanes (e.g., hexane, heptane), aromatic hydrocarbons (e.g., benzene, toluene), ethers (e.g., diethyl ether, dimethyl ether, diisopropyl ether) and a mixture of these solvents.

A preferred process for the preparation of the crystalline form of the compound of formula (I-K), comprises dissolving in a warmed appropriate solvent (e.g., esters) crude or amorphous compound of formula (I-K) (prepared for example in accordance with the procedures described in PCT Publication WO 2005/012326), and then adding an anti-solvent, as necessary, to the resulting solution, followed by cooling the resulting solution and filtration. The precise conditions under which the crystalline of the compound (I-K) is formed may be empirically determined.

One skilled in the art will recognize that the crystalline form of the compound of formula (I-K) is easier to isolate than the corresponding amorphous form of the compound of formula (I-K) and further, can be filtered from the crystallization medium after cooling, and washed and dried.

The present invention is further directed to pharmaceutical compositions comprising the crystalline form of the compound of formula (I-S) or the crystalline form of the compound of formula (I-K) and a pharmaceutically acceptable carrier.

The crystalline form of the compound of formula (I-S) and the crystalline form of the compound of formula (I-K) of the present invention are further useful as inhibitors of sodium-dependent glucose transporters ($SGLT_2$), and show excellent blood glucose lowering effect. In an embodiment, the crystalline form of the compound of formula (I-S) and the crystalline form of the compound of formula (I-K) of the present invention are useful in the treatment, prevention or in delaying the progression or onset of diabetes mellitus (type 1 and type 2 diabetes mellitus, etc.), diabetic complications (such as diabetic retinopathy, diabetic neuropathy, diabetic nephropathy), postprandial hyperglycemia, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, atherosclerosis, or hypertension.

The present invention further comprises pharmaceutical compositions containing a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like.

Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein may contain, per unit dosage unit, e.g., tablet, capsule, powder, injection, suppository, teaspoonful and the like, of from about 0.01-1000 mg or any range therein, and may be given at a dosage of from about 0.01-300 mg/kg/day, or any range therein, preferably from about 0.1-50 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

The daily dosage may be varied over a wide range from 0.01 to 1,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 30.0, 50.0, 75.0, 100.0, 150.0, 200.0, 250.0, 300.0 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any range therein, preferably at a dosage level of from about 0.01 mg/kg to about 100 mg/kg, or any range therein. More preferably, the range is from about 0.01 to about 50.0 mg/kg of body weight per day, or any range therein, more preferably still, from about 0.01 to about 30.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

(5-Bromo-2-methyl-phenyl)-[5-(4-fluoro-phenyl)-thiophen-2-yl]-methanone

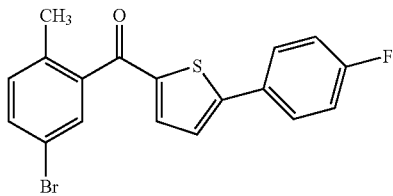 [SMILES: Cc1ccc(Br)cc1C(=O)c1ccc(-c2ccc(F)cc2)s1]

Step A:

A 250 mL three-necked round bottom flask was charged with 5-bromo-2-methylbenzoic acid (22.5 g, 0.10 mol), CH$_2$Cl$_2$ (100 mL) and DMF (0.25 mL) at ambient temperature (20° C.). Oxalyl chloride (12 mL, 0.13 mol) was added such that the internal temperature was maintained below 25° C. Vigorous gas evolution was observed. The reaction mixture was stirred overnight at ambient temperature, under argon, then the volatiles were removed under reduced pressure. The resulting residue (an acid chloride compound) was dissolved in DCM (50 mL) and set aside under a nitrogen atmosphere.

Step B:

In a separate 500 mL 3-necked round bottom flask was added AlCl$_3$ (15.0 g, 0.11 mol) and 100 mL of CH$_2$Cl$_2$. The suspension was cooled to −10° C. in an ice bath then 2-(4-fluorophenyl)thiophene (18.2 g, 0.10 mol) was added followed by addition of the mixture prepared as in STEP A above. After 30 minutes the ice bath was removed and the resulting mixture stirred at ambient temperature for 2-3 h. The resulting mixture was cooled to −12° C. and quenched by the slow addition of water (20 mL), followed by 2N HCl (20 mL) and heptane (100 mL). A precipitate formed. The resulting mixture was stirred for 1-2 h then filtered to give the title compound as a yellow solid.

EXAMPLE 2

2-(5-Bromo-2-methyl-benzyl)-5-(4-fluoro-phenyl)-thiophene

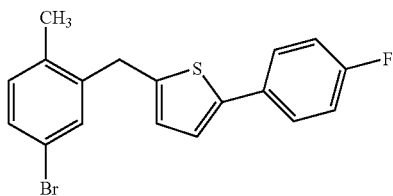 [SMILES: Cc1ccc(Br)cc1Cc1ccc(-c2ccc(F)cc2)s1]

A 3.0 L four-necked round bottom flask was charged with the compound prepared as in Example 1 above (119 g, 0.317 mol), triethylsilane (148 mL, 0.926 mol), dichloromethane (700 mL) and acetonitrile (700 mL). The resulting mixture was cooled to −8° C. in an ice bath, with stirring, then boron trifluoride diethyl etherate (115 mL, 0.915 mol) was added dropwise, such that the temperature did not exceed 0° C. The resulting mixture was warmed to room temperature and stirred overnight. The resulting mixture was concentrated under reduced pressure, diluted with IPA (1.0 L), filtered and washed with water to yield a solid. Recrystallization of the solid from IPA yielded the title compound as a yellow solid.

EXAMPLE 3

2-(4-Fluoro-phenyl)-5-(5-iodo-2-methyl-benzyl)-thiophene

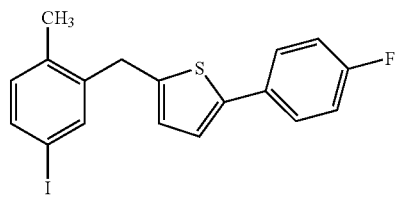

A 1.0 L four-necked reaction flask was charged with the compound prepared as in Example 2 above (100 g, 276.80 mmoles), sodium Iodide (82 g, 553.59 mmoles) and Copper (I) Iodide (2.6 g, 13.84 mmoles). The resulting mixture was evacuated and purged with argon, then treated with toluene (261 mL), diglyme (56 mL) and N,N'-dimethyl-ethane-1,2-diamine (2.7 mL, 27.68 mmoles) and the resulting mixture warmed to 110° C. overnight. Upon consumption of starting material, the resulting mixture was cooled to room temperature, then filtered through Celite®, washed with EtOAc, and extracted with NH$_4$OH. The organic phase was dried (Na$_2$SO$_4$), filtered and concentrated to yield a solid. The solids were filtered and recrystallized from heptane to yield the title compound as an off white solid (m.p. 107° C.).

(See also, Klaper, A., Buchwald, S. L., "Copper-Catalyzed Halogen Exchange in Aryl Halides: An Aromatic Finkelstein Reaction", *J. Am. Chem. Soc.*, 2002, 124, 14844-14814)

EXAMPLE 4

2,3,4,6-tetra-O-Trimethylsilyl-β-D-glucolactone

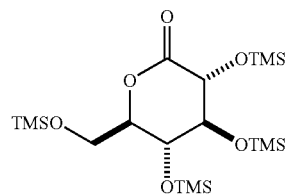

A 5.0 L three-necked round bottom flask was charged with gluconolactone (155.2 g, 0.871 mol) and 4-methylmorpholine (766 mL, 6.96 mol) in THF (1.55 L). To the cooled (−10° C.) mixture was added chlorotrimethylsilane (660 mL, 5.21 mol) at a rate such that the temperature did not exceed 5° C. After 1 hr the reaction mixture was heated to about 35-40° C. for 5 hr, then stirred at ambient temperature overnight, under argon. The resulting mixture was cooled to −10° C. and water (500-600 mL) was slowly added until no severe exotherm was observed. The resulting mixture was diluted with 4.0 L of water and 2.5 L of heptane. The layers were separated and the organic phase washed with aqueous sodium phosphate monobasic (1.5 L), water (1.0 L) and brine (1.0 L). The organic layer was dried over magnesium sulfate then concentrated under vacuum to yield the title compound as a light yellow liquid.

EXAMPLE 5

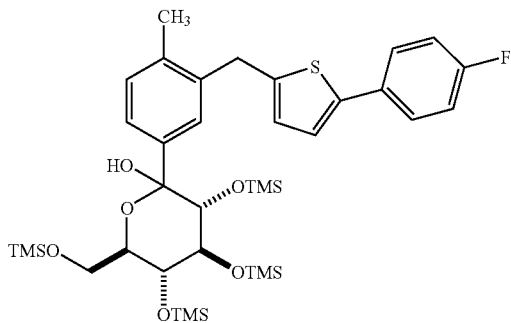

A 2.0 L three-necked round bottom flask was charged with the compound prepared as in Example 3 above, (100 g, 232.68 mmoles), the compound prepared as in Example 4 above (141 g, 302.49 mmoles) and tetrahydrofuran (750 mL). Upon cooling the resulting mixture to about −40° C., 1.0 M (trimethylsilyl)methyllithium in hexane (489 mL, 489 mmoles) was charged to the mixture using an addition funnel, with the internal temperature maintained at less than or equal to about −40° C. After addition was complete, the reaction was quenched with std. NaHCO$_3$ (200 mL) and allowed to warm to room temperature. The phases were separated, dried (Na$_2$SO$_4$), filtered and concentrated to yield the title compound as a thick oil.

EXAMPLE 6

1-(β-D-Glucopyranosyl)-4-methyl-3-(5-(4-fluorophenyl)-2-thienylmethyl)benzene

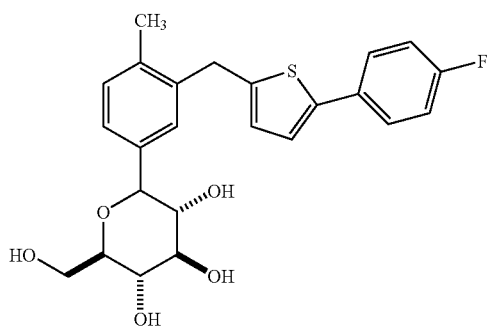

A 2.0 L three-necked round bottom flask was charged with the compound prepared as in Example 5 above (232 g, 310 mmol) and dichloroethane (700 mL). The resulting yellow solution was cooled to −30° C. in an ice bath, with stirring. Triethylsilane (132 mL, 826 mmol) was added followed by a slow addition (1.75 h) of boron trifluoride diethyl etherate (95.0 mL, 756 mmol) such that the temperature did not exceed −20° C. Approximately 30 minutes after the addition was complete the ice bath was removed and the resulting yellow mixture was stirred at ambient temperature, under argon, for 1.0-1.5 hour. Upon complete reaction the resulting mixture was poured into cold water (800 mL). Ethyl acetate (300 mL) was added and the layers were separated. The organic layer was washed with a saturated bicarbonate solution, dried over sodium sulfate and concentrated to yield the title compound as a green foam.

EXAMPLE 7

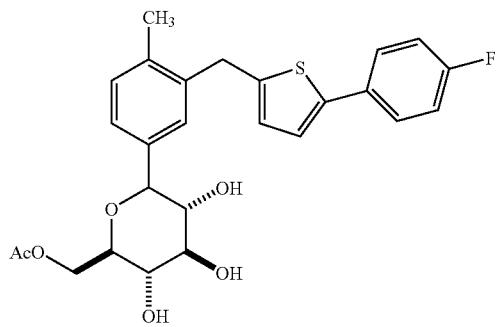

A 2.0 L three-necked round bottom flask was charged with the compound prepared as in Example 6 above, (119 g, 0.25 mol), 4-methylmorpholine (145 mL, 1.30 mol), DMAP (3.25 g, 0.026 mol) and 1.0 L of THF. The resulting light green mixture was cooled to −10° C. in an ice bath, with stirring, then acetic anhydride (125 mL, 1.30 mol) was added dropwise, such that the temperature did not exceed 0° C. The ice bath was removed 15 minutes after the addition was complete. The resulting mixture was stirred at ambient temperature for 1.0 h, then concentrated under reduced pressure at 30-35° C. to remove most of the solvent. The resulting mixture was diluted with 10% phosphoric acid (~300 mL), which resulted in the formation of a cream colored precipitate. The resulting mixture was dissolved in a mix of ethyl acetate (600-800 mL), THF (200-300 mL) and toluene (200-300 mL). Once complete solution was obtained, the layers were separated and the organic layer washed with saturated bicarbonate solution and brine, then dried and concentrated to yield a thick residue. Methanol was added to the residue causing an off-white solid to precipitate out of solution. The slurry was stirred for 30 minutes, then filtered to yield the title compound as an off-white solid.

EXAMPLE 8

1-(β-D-Glucopyranosyl)-4-methyl-3-(5-(4-fluorophenyl)-2-thienylmethyl)benzene

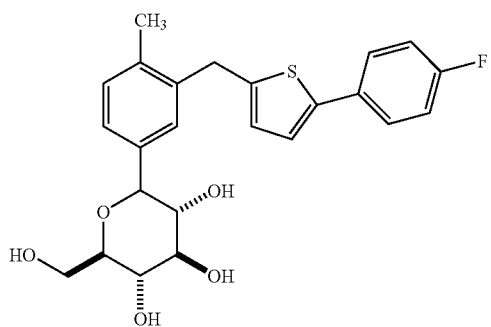

A flask was charged with the compound prepared as in Example 7 above, (185 g, 302 mmol) in THF (820 mL) and MeOH (1.23 L). To the stirred suspension was added a solution of lithium hydroxide monohydrate (6.33 g, 147 mmol) in water (410 mL). After stirring overnight at ambient temperature the volatiles were removed and the resulting residue diluted with ethyl acetate (500-600 mL). The layers were separated and the aqueous layer extracted with ethyl acetate (3×100 mL). The combined organic layer was washed with brine (250 mL), dried over sodium sulfate and concentrated under reduced pressure to yield the title compound as a brittle foam.

EXAMPLE 9

Crystallization of 1-(β-D-Glucopyranosyl)-4-methyl-3-(5-(4-fluorophenyl)-2-thienylmethyl)benzene

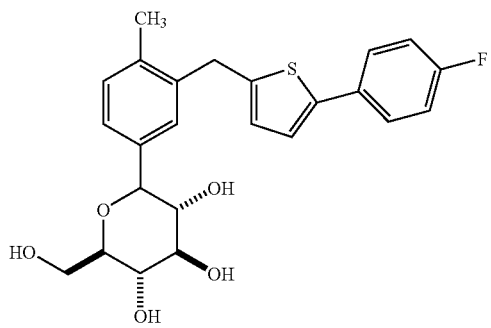

A 1.0 L three-necked round bottom flask was charged with the compound prepared as in Example 8 above (96.9 g, 217 mmol), water (6.0 mL, 333 mmol) and ethyl acetate (275 mL). The resulting solution was heated to 35° C., with stirring, under argon. Heptane was added dropwise until the solution became hazy (155 mL heptane), followed by the addition of 14.2 g of seed crystals. After stirring for 1.5-2.0 hrs at 35° C. additional heptane (30 mL, for a total of 185 mL) was added. The resulting mixture was stirred for 30 minutes more then filtered. The filter cake was washed with about 56% ethyl acetate/heptane (50 mL) and dried to yield the title compound as a fluffy, off-white crystalline solid.

The procedures as described in Examples 1 through 9 above were run multiple times to yield multiple batches of 1-(β-D-glucopyranosyl)-4-methyl-3-(5-(4-fluorophenyl)-2-thienylmethyl)benzene, the compound of formula (I-S).

The melting point, mass spec and $^1$HNMR spectra, as measured for a representative sample of the compound of formula (I-S) (prepared according to the procedures in Example 1 through 9) are as follows:

Melting Point: 106-107° C.;
Mass Spec: m/z (LCMS API-ES) 467 (M$^+$Na);
$^1$H NMR (CD$_3$OD): δ=2.32 (s, 3H), 3.35-3.53 (m, 4H), 3.71 (d, 1H, J=11.9 Hz), 3.90 (d, 1H, J=11.9 Hz), 4.13 (d, 1H, J=9.3 Hz), 4.17 (s, 2H), 4.9 (s, 4H), 6.70 (d, 1H, J=3.7 Hz), 7.04-7.14 (m, 3H), 7.18 (d, 1H, J=7.8 Hz), 7.26 (d, 1H, J=7.8 Hz), 7.33 (s, 1H), 7.52-7.60 (m, 2H).

A representative sample of the crystalline form of the compound of formula (I-S), isolated as described in Example 9 above, was characterized as to its x-ray powder diffraction, (a representative example of which is shown in FIG. 1) utilizing a diffractometer using CuK$_\alpha$ radiation 30 mA, 40 KV; 1/12° divergence slit, 0.2 receiving slit; scanning from 4 to 35° 2θ at a scan rate of 0.016° 2θ/second; and using an aluminum sample holder.

The crystalline form of the compound of formula (I-S) may be characterized by its powder XRD peaks, (preferably, by its powder XRD peaks with a relative intensity of greater than about 10%, more preferably, by its powder XRD peaks with a relative intensity of greater than about 25%, more preferably still, by its powder XRD peaks with a relative intensity of greater than about 35%, more preferably still, by its powder XRD peaks with a relative intensity of greater than about 50%), as listed in Table 1 below.

TABLE 1

Crystalline Form of Compound of Formula (I-S) Powder XRD Peaks

| Position (2° theta) | d-spacing (Å) | Relative Intensity (%) |
|---|---|---|
| 3.9 | 22.8 | 86.7 |
| 8.0 | 11.1 | 22.1 |
| 9.7 | 9.2 | 10.5 |
| 10.9 | 8.1 | 33.3 |
| 13.0 | 6.8 | 16.2 |
| 13.9 | 6.4 | 18.4 |
| 15.5 | 5.7 | 100 |
| 15.6 | 5.7 | 64.5 |
| 15.9 | 5.6 | 16.8 |
| 16.2 | 5.5 | 14.2 |
| 17.3 | 5.1 | 44.0 |
| 18.3 | 4.9 | 18.6 |
| 18.7 | 4.7 | 38.5 |
| 18.8 | 4.7 | 56.6 |
| 19.1 | 4.6 | 21.1 |
| 19.4 | 4.6 | 21.3 |
| 20.3 | 4.4 | 44.2 |
| 20.9 | 4.3 | 19.4 |
| 21.1 | 4.2 | 12.3 |
| 21.8 | 4.1 | 10.2 |
| 22.5 | 3.9 | 13.4 |
| 22.7 | 3.9 | 32.3 |
| 23.2 | 3.8 | 11.4 |
| 23.4 | 3.8 | 27.0 |
| 25.1 | 3.6 | 19.8 |
| 25.7 | 3.5 | 12.2 |
| 26.3 | 3.4 | 11.3 |
| 26.8 | 3.3 | 25.6 |
| 27.3 | 3.3 | 13.6 |

EXAMPLE 10

(2-Chloro-5-iodo-phenyl)-[5-(6-fluoro-pyridin-3-yl)-thiophen-2-yl]-methanone

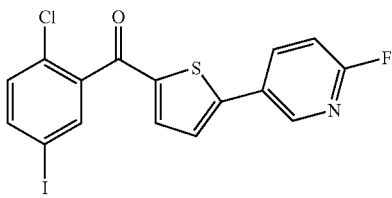 [SMILES: O=C(c1ccc(-c2ccc(F)nc2)s1)c1cc(I)ccc1Cl]

Step A:
A 5.0 L four-necked round bottom flask was charged with 2-chloro-5-iodobenzoic acid (470.8 g, 1.66 mol), $CH_2Cl_2$ (1.6 L) and DMF (5.0 mL, 0.03 mol) at ambient temperature (20° C.). Oxalyl chloride (170 mL, 1.94 mol) was added such that the internal temperature was maintained below 25° C. The addition was slightly exothermic; vigorous gas evolution occurred. The resulting mixture was stirred overnight at ambient temperature, under argon, then the volatiles were removed under reduced pressure. The resulting residue (an acid chloride compound) was diluted with dichloromethane (500 mL) and set aside under a nitrogen atmosphere.

Step B:
In a separate 5.0 L 3-necked round bottom flask was added $AlCl_3$ (487.0 g, 3.65 mol) and 1.5 L of $CH_2Cl_2$. To the cooled (−12° C.) mixture was added 2-fluoro-5-(2-thienyl)pyridine (299.0 g, 1.66 mol) followed by addition of the mixture prepared as in STEP A above. After 20 minutes the ice bath was removed and the reaction mixture stirred at ambient temperature for 2-3 h. Upon completion of the reaction the resulting mixture was cooled to −12° C. and quenched by the slow addition of water (400-500 mL) followed by 2N HCl (100 mL) and heptane (100 mL). The reaction temperature was not allowed to exceed 32° C. during the water quench. The resulting mixture was stirred at ambient temperature overnight, resulting in the formation of a precipitate. The resulting mixture was filtered, washed with water and dried to yield a solid. The solid was recrystallized from ethyl acetate to yield the title compound as a gold colored solid.

EXAMPLE 11

5-[5-(2-Chloro-5-iodo-benzyl)-thiophen-2-yl]-2-fluoro-pyridine

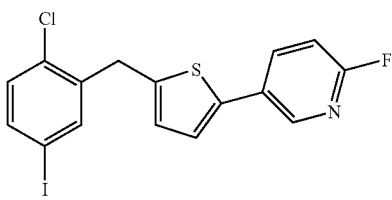 [SMILES: Fc1ccc(-c2ccc(Cc3cc(I)ccc3Cl)s2)cn1]

A 5.0 L four-necked round bottom flask was charged with the compound prepared as in Example 10 above, (350 g, 0.787 mol), triethylsilane (650 mL, 4.07 mol) and acetonitrile (1.75 L). The resulting mixture was heated to 30° C. then boron trifluoride diethyl etherate (500 mL, 3.98 mol) was added, dropwise, such that the temperature did not exceed 58° C. Stirring was continued at ambient temperature. Upon completion, the resulting mixture was added to a cooled (5° C.) aqueous sodium bicarbonate solution (400 g in 2.0 L of water). The aqueous mixture was stirred at ambient temperature for an hour then diluted with ethyl acetate (500 mL). The layers were separated and the aqueous layer extracted with ethyl acetate (2×400 mL). The combined organic was washed with brine, dried and concentrated to yield a light brown solid. The solid was dissolved in hot toluene (about 1.5-1.75 L), treated with silica gel (250 g), diluted with heptane (1.0 L), stirred for 30-40 minutes then filtered hot. The volume was reduced and additional heptane added. A solid precipitated out of solution on cooling to room temperature. The resulting mixture was filtered to yield the title compound as a yellow solid.

EXAMPLE 12

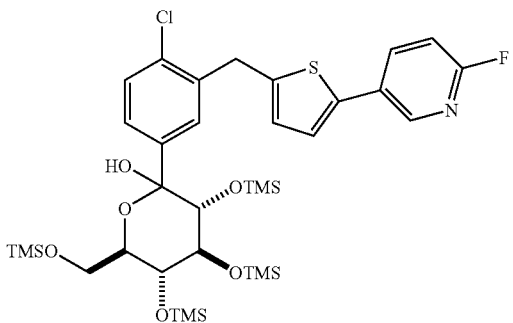

A 1 L Erlenmeyer flask was charged with the compound prepared as in Example 11 above (94.4 g, 219.70 mmoles), the compound prepared as in Example 4 above (102 g, 219.70 mmoles) and tetrahydrofuran (585 mL). The resulting mixture was filtered through a sintered glass funnel packed with Celite® and molecular sieves, 4AE (10 g) into a 2.0 L three-necked round bottom flask equipped with and overhead stirrer, nitrogen outlet, thermocouple and addition funnel with a vacuum adapter. The resulting mixture was then cooled to −70° C. via dry ice/acetone bath. The addition funnel was charged with 1.0 M (trimethylsilyl)methyllithium in hexanes (450 mL; 450 mmoles), with the internal temperature maintained at less than about −60° C. After addition was complete, the resulting mixture was allowed to warm to −30° C., then quenched into a stirred mixture of $NaHCO_3$ (400 mL, 50% saturated) in a 2 L separatory funnel, diluted with heptane (200 mL) and the phases separated. The organic phase was washed with water (20 mL), brine (50 mL) then phase separated and dried ($Na_2SO_4$), filtered and concentrated to yield the title compound as a thick oil.

EXAMPLE 13

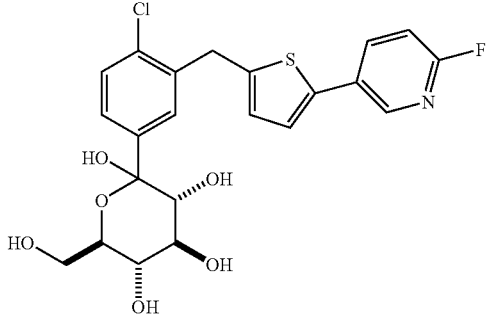

A 2 L three-neck round bottom flask equipped with a cold bath, addition funnel, temperature sensor, nitrogen outlet and overhead stirrer was charged with the product prepared as in Example 11 above (100 g, 232.73 mmoles) and the compound prepared as in Example 4 above (130.4 g, 325.8 mmoles), followed by addition of THF (660 mL). The resulting mixture was then cooled to −70° C. via dry ice bath in acetone. The addition funnel was charged with trimethylsilylmethyl lithium (210 mL; 413.70 mmoles), which was added to the reaction mixture slowly, as to maintain an internal temperature of less than about −70° C. After addition, the resulting mixture was allowed to stir for another 20 min. The resulting mixture was worked up by addition via addition funnel of 2M HCl (250 mL; 500.00 mmoles). The resulting mixture was then allowed to warm to room temperature, then transferred to a separatory funnel and extracted with ethyl acetate (2×200 mL). The organic phase was separated and dried (MgSO$_4$), and the resulting mixture filtrated and concentrated to yield the title compound as a thick oil.

EXAMPLE 14

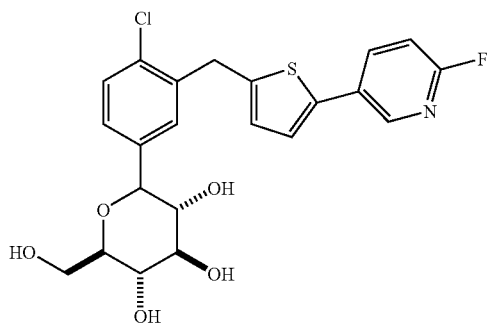

A 3.0 L four-necked round bottom flask was charged with the compound prepared as in Example 13 above, (112 g, 0.23 mol) and acetonitrile (1.0 L). The resulting mixture was cooled to −20° C. in an ice bath, with stirring. Triethylsilane (185 mL, 1.16 mol) was added, followed by a slow addition of boron trifluoride diethyl etherate (150 mL, 1.20 mol) such that the temperature was maintained at −20° C. After the addition was complete the resulting dark orange mixture was allowed to slowly warm to 0° C. Upon completion an aqueous solution of sodium bicarbonate (200 g in 500 mL of distilled water) was added to the resulting mixture and the layers separated. The organic layer was concentrated to remove most of the acetonitrile then diluted with ethyl acetate (350 mL). The aqueous layer was saturated with sodium chloride then extracted with ethyl acetate (350 mL). The combined organic layer was washed with a saturated sodium chloride solution (100 mL), dried over sodium sulfate (135 g) and concentrated to yield the title compound as a yellow colored foam.

EXAMPLE 15

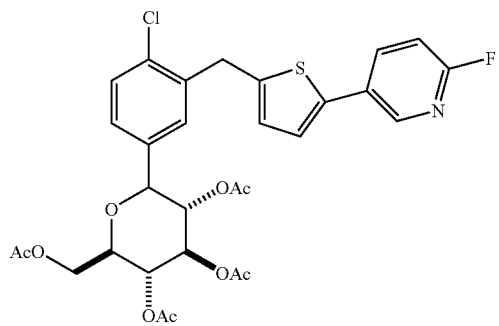

A 500 mL three-necked round bottom flask was charged with the compound prepared as in Example 14 above (23.56 g, 50.0 mmol), 4-methylmorpholine (27.5 mL, 250 mmol) and DMAP (0.60 g, 4.86 mmol) in THF (160 mL). The resulting yellow mixture was cooled to −10° C. in an ice bath, with stirring, then acetic anhydride (23.6 mL, 250 mmol) was added dropwise, such that the temperature did not exceed 0° C. The ice bath was removed 15 minutes after the addition was complete. The resulting mixture was stirred at ambient temperature for 1.5 h, then concentrated under reduced pressure at about 30-35° C. to remove most of the solvent. The resulting residue was dissolved in ethyl acetate (100-150 mL) and diluted with 1 N HCl (100-150 mL). The layers were separated and the aqueous layer extracted with ethyl acetate (2×30 mL). The combined organic layer was washed with 100 mL each of water, a saturated bicarbonate solution and brine, then dried and concentrated to yield a damp solid. The solid was recrystallized from hot methanol (300-425 mL) to yield the title compound as a light yellow solid.

EXAMPLE 16

1-(β-D-glucopyranosyl)-4-methyl-3-(5-(6-fluoro-pyrid-3-yl)-2-thienylmethyl)benzene

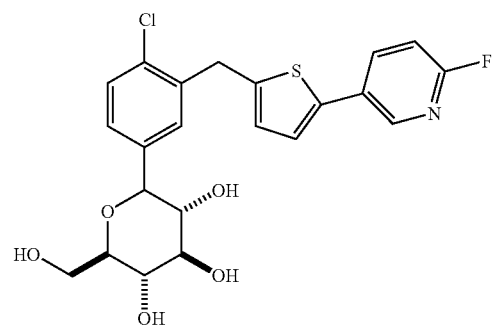

A 250 mL one-necked round bottom flask was charged with the compound prepared as in Example 15 above (8.52 g, 13.4 mmol) in THF (50 mL) and methanol (50 mL). To the stirred suspension was added 3N sodium hydroxide (1.2 mL, 3.60 mmol). The resulting mixture was stirred for 1 hr at ambient temperature. The volatiles were removed and the resulting residue diluted with ethyl acetate (50 mL). The layers were separated and the aqueous layer extracted with ethyl acetate (3×10 mL). The combined organic layer was washed with brine, dried over sodium sulfate, filtered and concentrated to half the volume, yielding a solid precipitate. The title compound was isolated by filtration, as a cream colored solid.

The melting point, mass spec and $^1$HNMR spectra, as measured for a representative sample of the compound of formula (I-K) (prepared according to the procedures as described in the Examples above) are as follows:

Melting Point: 130-132° C.;

Mass Spec: m/z (LCMS API-ES) 466 (M$^+$H);

$^1$H NMR (DMSO-d6): δ=3.05-3.31 (m, 4H), 3.45 (dt, 1H, J=5.3 Hz, J=12.2 Hz), 3.70 (dd, 1H, J=5.3 Hz, J=11.4 Hz), 4.02 (d, 1H, J=9.7 Hz), 4.28 (d, 2H, J=3.5 Hz), 4.46 (t, 1H, J=6.2 Hz), 4.89 (d, 1H, J=6.2 Hz), 4.99 (d, 2H, J=5.3 Hz), 6.93 (d, 1H, J=3.5 Hz), 7.21 (dd, 1H, J=3.5 Hz, J=8.3 Hz), 7.28 (dd, 1H, J=2.0 Hz, J=8.3 Hz), 7.39-7.48 (m, 3H), 8.17 (ddd, 1H, J=16.2 Hz, J=8.3 Hz, J=2.6 Hz), 8.46 (s, 1H)

The compound of formula (I-K), prepared as for example, described in Example 16 above, may be characterized by its powder XRD peaks, (preferably, by its powder XRD peaks with a relative intensity of greater than about 10%, more preferably, by its powder XRD peaks with a relative intensity of greater than about 25%, more preferably still, by its powder XRD peaks with a relative intensity of greater than about 35%, more preferably still, by its powder XRD peaks with a relative intensity of greater than about 50%), as listed in Table 2 below.

TABLE 2

Crystalline Form of Compound of Formula (I-K) Powder XRD Peaks

| Position (2° theta) | d-spacing (Å) | Relative Intensity (%) |
|---|---|---|
| 10.22 | 8.65 | 19 |
| 12.88 | 6.87 | 18 |
| 14.58 | 6.07 | 35 |
| 16.36 | 5.41 | 41 |
| 18.36 | 4.83 | 43 |
| 18.62 | 4.76 | 85 |
| 18.76 | 4.73 | 64 |
| 19.20 | 4.62 | 88 |
| 19.84 | 4.47 | 100 |
| 20.58 | 4.31 | 61 |
| 20.76 | 4.28 | 92 |
| 21.20 | 4.19 | 45 |
| 21.88 | 4.06 | 46 |
| 22.74 | 3.91 | 31 |
| 22.96 | 3.87 | 55 |
| 23.14 | 3.84 | 31 |
| 24.44 | 3.64 | 56 |
| 24.68 | 3.60 | 45 |
| 25.06 | 3.55 | 44 |
| 25.58 | 3.48 | 23 |
| 26.24 | 3.39 | 28 |
| 27.20 | 3.28 | 53 |
| 27.66 | 3.22 | 19 |
| 28.04 | 3.18 | 23 |
| 28.24 | 3.16 | 23 |
| 29.48 | 3.03 | 40 |
| 30.78 | 2.90 | 56 |
| 31.08 | 2.88 | 20 |
| 32.22 | 2.78 | 34 |
| 33.40 | 2.68 | 19 |
| 33.76 | 2.65 | 29 |
| 35.36 | 2.54 | 25 |
| 37.82 | 2.38 | 29 |

EXAMPLE 17

Crystallization of 1-(β-D-glucopyranosyl)-4-chloro-3-[5-(6-fluoro-3-pyridyl)-2-thienylmethyl]benzene 1-(β-D-Glucopyranosyl)-4-chloro-3-[5-(6-fluoro-3-pyridyl)-2-thienylmethyl]benzene (foam, 23.1 g; prepared as described in PCT Publication WO 2005/012326) was dissolved in ethyl acetate (345 ml), and thereto was added a seed of the crystalline form of 1-(β-D-glucopyranosyl)-4-chloro-3-[5-(6-fluoro-3-pyridyl)-2-thienylmethyl]benzene. The mixture was refluxed for 30 minute and then stirred at 50° C. for 14 hours. After being cooled to room temperature, the precipitate was collected by filtration, washed with ethyl acetate (100 ml) and dried to yield crystalline 1-(β-D-glucopyranosyl)-4-chloro-3-[5-(6-fluoro-3-pyridyl)-2-thienylmethyl]benzene (20.34 g) as colorless crystals.

mp 131-134° C.

Elemental Analysis Calculated for $C_{22}H_{21}ClFNO_5S$: C, 56.71; H, 4.54; N, 3.01; F, 4.08; Cl, 7.61; S, 6.88; Measured As: C, 56.59; H, 4.55; N, 3.01; F, 4.00; Cl, 7.60; S, 6.94.

EXAMPLE 18

1-(β-D-Glucopyranosyl)-4-chloro-3-[5-(6-fluoro-3-pyridyl)-2-thienylmethyl]benzene To a solution of 1-(2,3,4,6-tetra-O-acetyl-1-β-D-glucopyranosyl)-4-chloro-3-(5-(6-fluoro-3-pyridyl)-2-thienylmethyl)benzene (9.64 g; prepared as described in PCT Publication WO 2005/012326) in a mixture of methanol-tetrahydrofuran (75 ml-75 ml) was added a solution of sodium methoxide in methanol (28%, 0.09 ml), and the resulting mixture was stirred at room temperature under argon atmosphere for 1.5 hours. The organic solvent was evaporated under reduced pressure, and thereto was added brine (200 ml). The mixture was extracted with ethyl acetate (500 ml), and the organic layer was dried over magnesium sulfate. After being treated with activated carbon, the insoluble materials were filtered off, and the filtrate was evaporated under reduced pressure. The residue was dissolved in ethyl acetate (60 ml), and thereto was added a seed of the crystalline of 1-(β-D-glucopyranosyl)-4-chloro-3-[5-(6-fluoro-3-pyridyl)-2-thienylmethyl]benzene. The mixture was stirred at 50° C. for 2.5 hours, refluxed for 45 minutes and stirred at room temperature overnight. The precipitated crystals were triturated, and the mixture was again stirred at 50° C. for 30 minutes, refluxed for 45 minutes and stirred at room temperature overnight. The precipitated crystals were collected, washed with ethyl acetate (40 ml) twice and dried to yield colorless crystalline of 1-(β-D-glucopyranosyl)-4-chloro-3-[5-(6-fluoro-3-pyridyl)-2-thienylmethyl]benzene (5.59 g).

mp 131-133° C.

EXAMPLE 19

Reference Example A

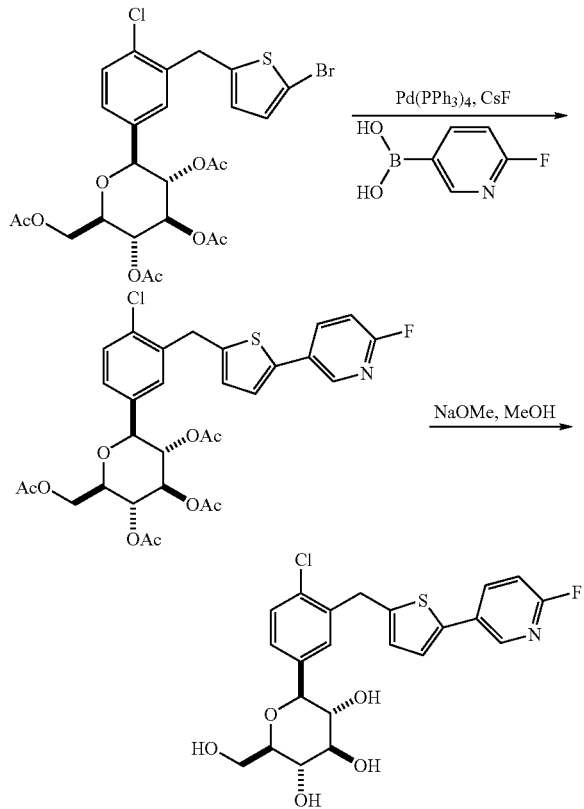

STEP (1): Preparation of 1-(2,3,4,6-Tetra-O-acetyl-β-D-glucopyranosyl)-4-chloro-3-(5-(6-fluoro-3-pyridyl)-2-thienylmethyl)benzene A suspension of 1-(2,3,4,6-tetra-O-acetyl-β-D-glucopyranosyl)-4-chloro-3-(5-bromo-2-thienylmethyl)benzene (13.5 g; prepared as described in PCT Publication WO 2005/012326), 2-fluoropyridine-5-boronic acid (Frontier Scientific, 4.63 g), cesium fluoride (19.96 g) and tetrakis(triphenylphosphin)palladium(0) (2.53 g) in 1,2-dimethoxyethane (200 ml) was refluxed for 1.5 hours. The reaction mixture was poured into a saturated aqueous sodium hydrogen carbonate solution, and extracted with ethyl acetate. The organic layer was washed with brine, dried over sodium sulfate, and the solvent was evaporated under reduced pressure. The residue was dissolved in ethyl acetate, and the mixture was treated with activated carbon and filtered through aminosilane-treated silica gel (27 ml) pad. The filtrate was evaporated under reduced pressure, and the residue was purified by silica gel flash column chromatography (hexane:ethyl acetate:dichloromethane 2:1:1) and recrystallized from methanol to yield 1-(2,3,4,6-tetra-O-acetyl-β-D-glucopyranosyl)-4-chloro-3-(5-(6-fluoro-3-pyridyl)-2-thienylmethyl)benzene (8.33 g) as a colorless crystal.

mp 161-162° C.

IR (Nujol) 1736, 1493, 1463, 1379, 1229, 1215 cm$^{-1}$

APCI-Mass m/Z 634/636 (M+H), 651/653 (M+NH$_4$)

$^1$H-NMR (DMSO-d$_6$) δ 1.72 (s, 3H), 1.93 (s, 3H), 1.99 (s, 3H), 2.01 (s, 3H), 4.07-4.14 (m, 3H), 4.28 (s, 1H), 4.71 (d, J=9.8 Hz, 1H), 4.96 (t, J=9.5 Hz, 1H), 5.08 (t, J=9.5 Hz, 1H), 5.36 (t, J=9.5 Hz, 1H), 6.90 (d, J=3.7 Hz, 1H), 7.22 (dd, J=8.7, 2.5 Hz, 1H), 7.31-7.32 (m, 1H), 7.39 (d, J=2 Hz, 1H), 7.44-7.48 (m, 2H), 8.14-8.18 (m, 1H), 8.45 (d, J=2.0 Hz, 1H). Anal. Calcd for C$_{30}$H$_{29}$ClFNO$_9$S: C, 56.83; H, 4.61; Cl, 5.59; F, 3.0; N, 2.21; S, 5.06. Found: C, 56.8; H, 4.47; Cl, 5.6; F, 2.91; N, 2.29; S, 4.93.

STEP (2): Preparation of 1-(β-Glucopyranosyl)-4-chloro-3-[5-(6-fluoro-3-pyridyl)-2-thienylmethyl]benzene The compound prepared as in STEP (1) above (8.33 g) was dissolved in methanol (200 ml)-tetrahydrofuran (100 ml), thereto was added sodium methoxide (28% methanol solution, 5 drops), and the mixture was stirred at room temperature for 4 hours. The solvent was evaporated under reduced pressure, and the residue was purified by silica gel column chromatography (chloroform:methanol 100:0-88:12) and triturated with isopropyl ether-2-propanol to yield 1-(β-D-glucopyranosyl)-4-chloro-3-[5-(6-fluoro-3-pyridyl)-2-thienylmethyl]benzene (4.61 g) as a colorless powder.

APCI-Mass m/Z 466/468 (M+H), 483/485 (M+NH$_4$)

$^1$H-NMR (DMSO-d$_6$) δ 3.07-3.27 (m, 4H), 3.38-3.49 (m, 1H), 3.67-3.80 (m, 1H), 4.02 (d, J=9.4 Hz, 1H), 4.27 (app d, J=3.1 Hz, 2H), 4.33 (d, J=4.2 Hz, 1H), 4.85 (d, J=5.7 Hz, 1H), 4.95 (dd, J=5.0, 3.8 Hz, 2H), 6.92 (d, J=3.7 Hz, 1H), 7.18-7.22 (m, 1H), 7.26-7.29 (m, 1H), 7.40-7.44 (m, 3H), 8.13-8.19 (m, 1H), 8.44-8.45 (m, 1H).

EXAMPLE 20

As a specific embodiment of an oral composition, 100 mg of the compound prepared as in Example 9 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

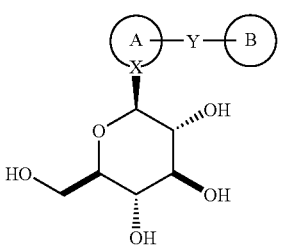

wherein Ring A and Ring B are one of the followings:
(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or
(3) Ring A is an optionally substituted unsaturated fused heterobicyclic ring, wherein the sugar moiety X-(sugar) and the moiety -Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;
Y is —(CH$_2$)$_n$—; wherein n is 1 or 2;
provided that in Ring A, X is part of an unsaturated bond;
or a pharmaceutically acceptable salt thereof, or a prodrug thereof;
comprising

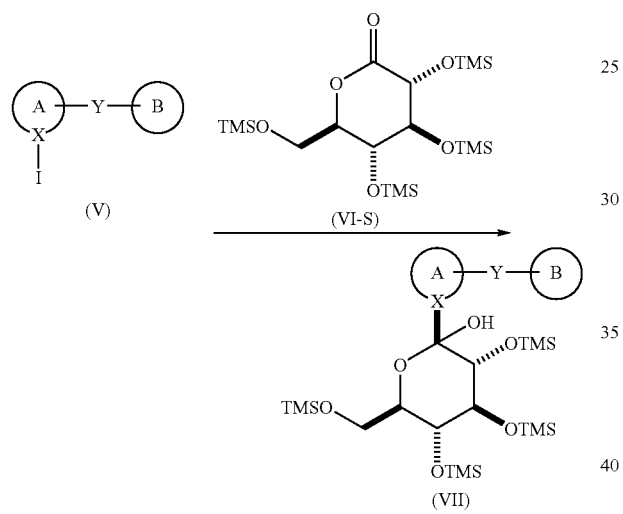

reacting a compound of formula (V) with a compound of formula (VI-S), in the presence of an alkyl lithium, wherein the alkyl lithium is selected from the group consisting of trimethylsilylmethyl lithium, 2,4,6-trimethylphenyl lithium and triethylsilylmethyl lithium; in an organic solvent, at a temperature in the range of from about 0° C. to about –78° C.; to yield the corresponding compound of formula (VII);
and wherein the alkyl lithium is added to a mixture of the compound of formula (V) and the compound of formula (VI-S);

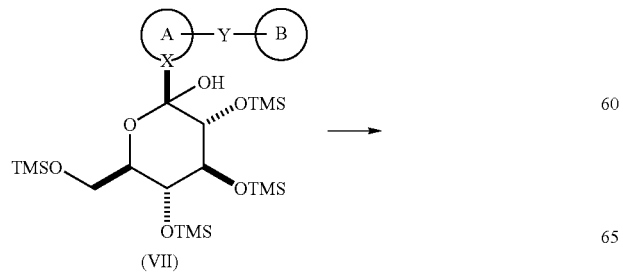

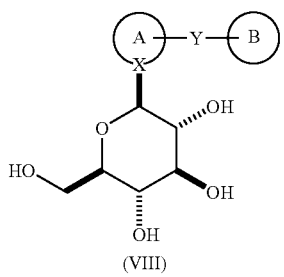

reacting the compound of formula (VII) with BF$_3$OEt$_2$, in the presence of a trialkylsilane, in an organic solvent, to yield the corresponding compound of formula (VIII);

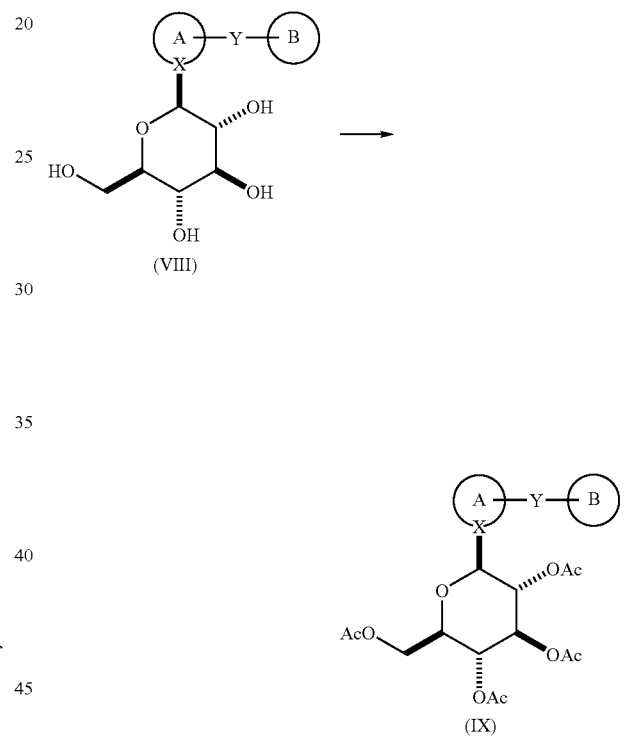

reacting the compound of formula (VIII) with acetic anhydride or acetyl chloride, in the presence of an organic base, neat or in an organic solvent, to yield the corresponding compound of formula (IX); and

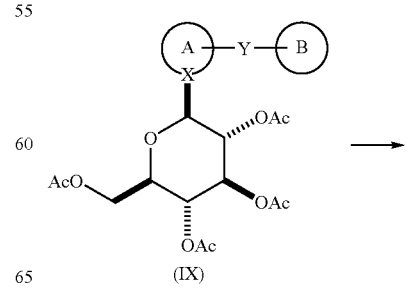

-continued

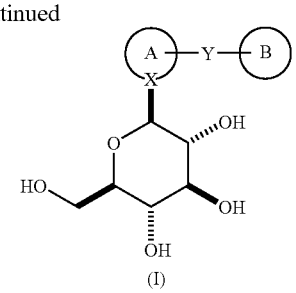

(I)

or a pharmaceutically acceptable salt or a prodrug thereof; comprising

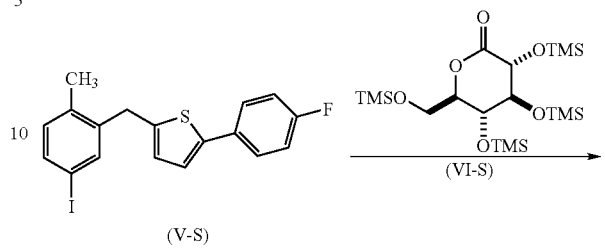

de-protecting the compound of formula (IX), to yield the corresponding compound of formula (I).

2. A process as in claim 1, wherein the compound of formula (VI-S) is present in an amount in the range of from about 1.0 to about 1.25 molar equivalents relative to the moles of the compound of formula (V).

3. A process as in claim 1, wherein the alkyl lithium is (trimethylsilyl)methyl lithium and wherein the alkyl lithium is present in an amount in the range of from about 2.0 to about 2.5 molar equivalents relative to the moles of the compound of formula (V).

4. A process as in claim 1, wherein the alkyl lithium is added to a mixture of the compound of formula (V) and the compound of formula (VI-S) in the organic solvent.

5. A process as in claim 1, wherein the $BF_3OEt_2$ is present in an amount in the range of from about 2.0 to about 6.0 molar equivalents relative to the moles of the compound of formula (VII) and wherein the trialkylsilane is $Et_3SiH$ and is present in an amount in the range of from about 2.0 to about 6.0 molar equivalents relative to the moles of the compound of formula (VII).

6. A process as in claim 5, wherein the molar ratio of $BF_3OEt_2$: $Et_3SiH$ is about 1:1.

7. A process as in claim 1, wherein the compound of formula (VIII) is reacted with acetic anhydride and wherein the acetic anhydride is present in an amount in the range of from about 4.5 to about 5.0 molar equivalents relative to the moles of the compound of formula (VII).

8. A process as in claim 1, wherein the organic base is NMM.

9. A process as in claim 1, wherein the compound of formula (VIII) is reacted with acetic anhydride in the presence of a catalytic amount of DMAP.

10. A process as in claim 1, wherein the compound of formula (IX) is de-protected by reacting with a base.

11. A process for the preparation of a compound of formula (I-S)

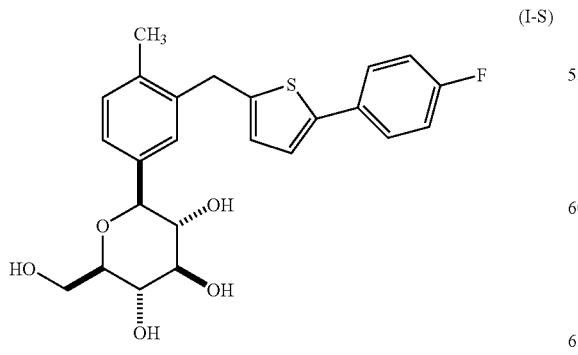

(I-S)

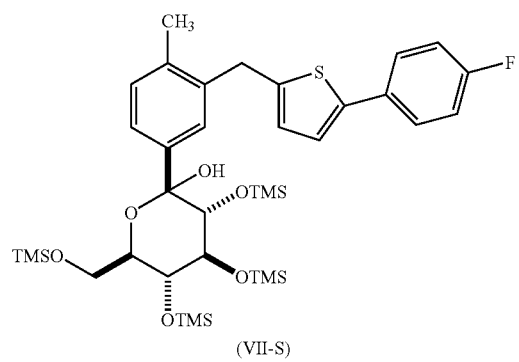

(VII-S)

reacting a compound of formula (V-S), with a compound of formula (VI-S), in the presence of an alkyl lithium, wherein the alkyl lithium is selected from the group consisting of trimethylsilylmethyl lithium, 2,4,6-trimethylphenyl lithium and triethylsilylmethyl lithium; in an organic solvent, at a temperature in the range of from about 0° C. to about −78° C., to yield the corresponding compound of formula (VII-S);

and wherein the alkyl lithium is added to a mixture of the compound of formula (V-S) and the compound of formula (VI-S);

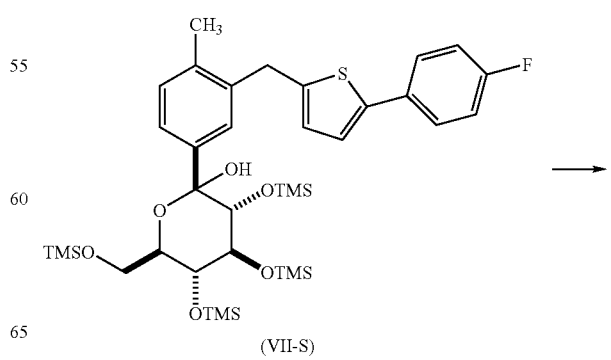

(VII-S)

-continued

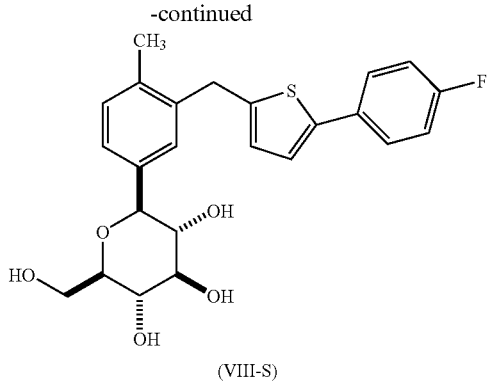
(VIII-S)

reacting the compound of formula (VII-S) with BF$_3$OEt$_2$, in the presence of a trialkylsilane, in an organic solvent, to yield the corresponding compound of formula (VIII-S);

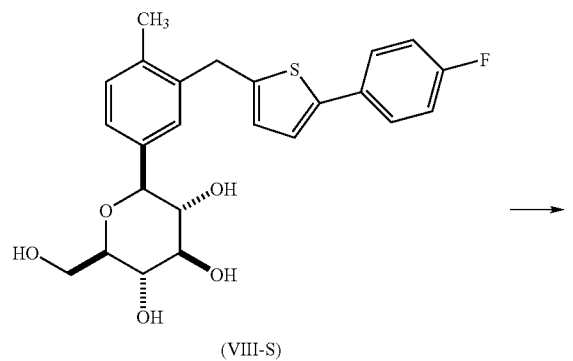
(VIII-S)

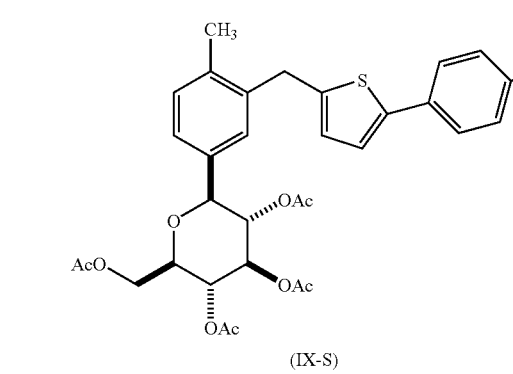
(IX-S)

reacting the compound of formula (VIII-S) with acetic anhydride or acetyl chloride, in the presence of an organic base, neat or in an organic solvent, to yield the corresponding compound of formula (IX-S); and

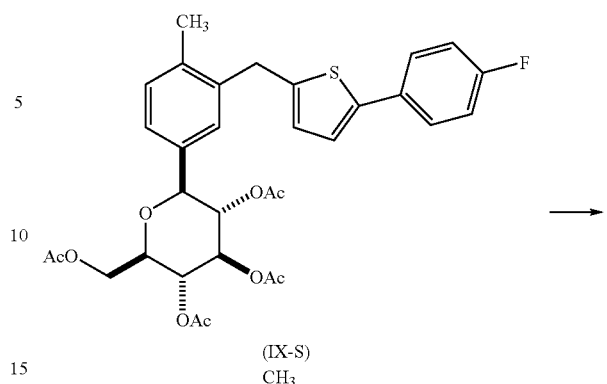
(IX-S)

(I-S)

de-protecting the compound of formula (IX-S) to yield the corresponding compound of formula (I-S).

12. A process as in claim 11, wherein the compound of formula (VI-S) is present in an amount in the range of from about 1.0 to about 1.25 molar equivalents relative to the moles of the compound of formula (V-S).

13. A process as in claim 11, wherein the alkyl lithium is (trimethylsilyl)methyl lithium and wherein the alkyl lithium is present in an amount in the range of form about 2.0 to about 2.5 molar equivalents relative to the moles of the compound of formula (V-S).

14. A process as in claim 11, wherein the alkyl lithium is added to a mixture of the compound of formula (V-S) and the compound of formula (VI-S) in the organic solvent.

15. A process as in claim 11, wherein the BF$_3$OEt$_2$ is present in an amount in the range of from about 2.0 to about 6.0 molar equivalents relative to the moles of the compound of formula (VII-S) and wherein the trialkylsilane is Et$_3$SiH and is present in an amount in the range of from about 2.0 to about 6.0 molar equivalents relative to the moles of the compound of formula (VII-S).

16. A process as in claim 15, wherein the molar ratio of BF$_3$OEt$_2$: Et$_3$SiH is about 1:1.

17. A process as in claim 11, wherein the compound of formula (VIII-S) is reacted with acetic anhydride and wherein the acetic anhydride is present in an amount in the range of from about 4.5 to about 5.0 molar equivalents relative to the moles of the compound of formula (VIII-S).

18. A process as in claim 11, wherein the organic base is NMM.

19. A process as in claim 11, wherein the compound of formula (VIII-S) is reacted with acetic anhydride in the presence of a catalytic amount of DMAP.

20. A process as in claim 11, wherein the compound of formula (IX-S) is further slurried in methanol and filtered.

21. A process as in claim 11, wherein the compound of formula (IX-S) is de-protected by reacting with a base.

22. A process for the preparation of a compound of formula (I-K)

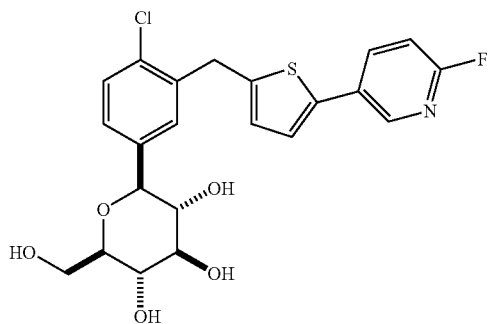
(I-K)

or a pharmaceutically acceptable salt thereof; comprising

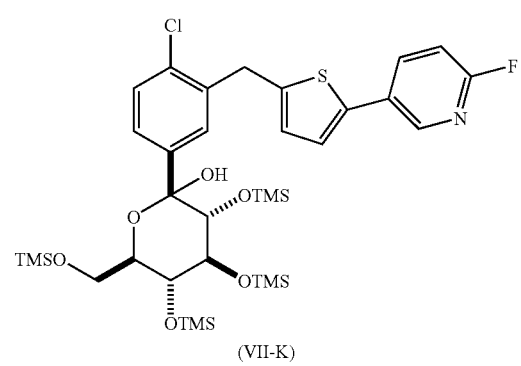

reacting a compound of formula (V-K), with a compound of formula (VI-S), in the presence of an alkyl lithium, wherein the alkyl lithium is selected from the group consisting of trimethylsilylmethyl lithium, 2,4,6-trimethylphenyl lithium and triethylsilylmethyl lithium; in an organic solvent, at a temperature in the range of from about 0° C. to about −78° C., to yield the corresponding compound of formula (VII-K);

and wherein the alkyl lithium is added to a mixture of the compound of formula (V-K) and the compound of formula (VI-S);

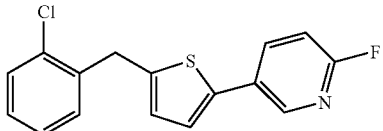
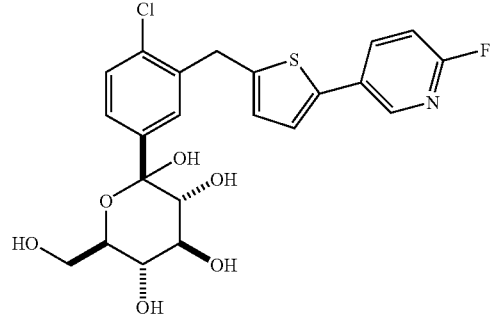
(X-K)

de-protecting the compound of formula (VII-K) to yield the corresponding compound of formula (X-K);

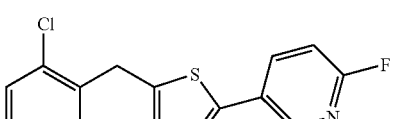
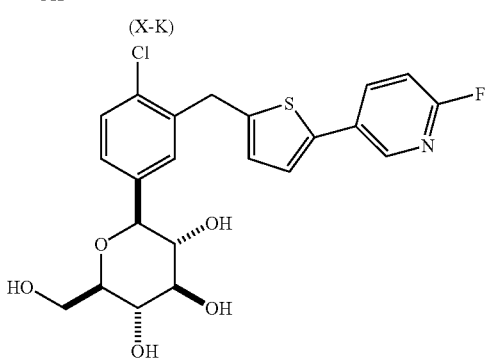
(VIII-K)

reacting the compound of formula (X-K) with $BF_3OEt_2$, in the presence of a trialkylsilane, in an organic solvent, to yield the corresponding compound of formula (VIII-K);

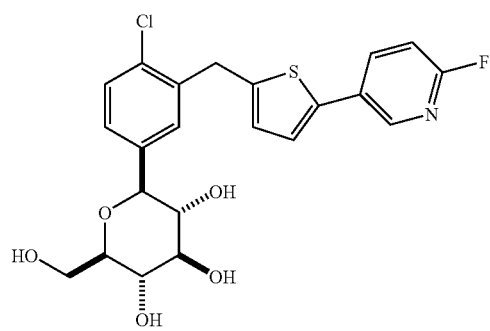

(VIII-K)

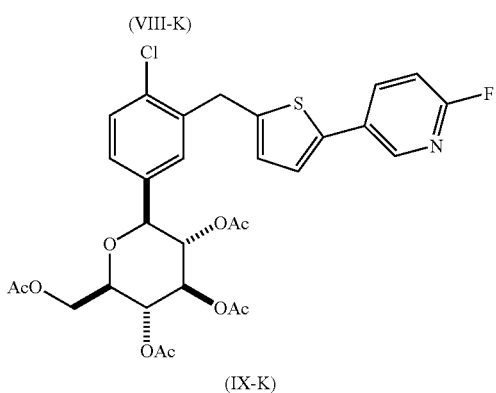

(IX-K)

reacting the compound of formula (VIII-K) with acetic anhydride or acetyl chloride, in the presence of an organic base, neat or in an organic solvent, to yield the corresponding compound of formula (IX-K); and

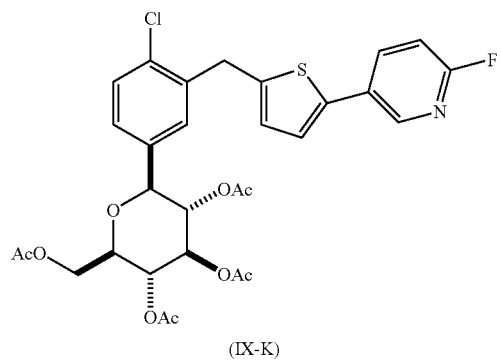

(IX-K)

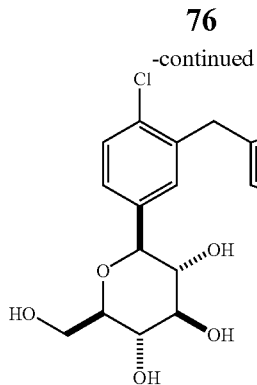

(I-K)

de-protecting the compound of formula (IX-K) to yield the corresponding compound of formula (I-K).

23. A process as in claim 22, wherein the compound of formula (VI-S) is present in an amount in the range of from about 1.0 to about 1.25 molar equivalents relative to the moles of the compound of formula (V-K).

24. A process as in claim 22, wherein the alkyl lithium is (trimethylsilyl)methyl lithium and wherein the alkyl lithium is present in an amount in the range of form about 2.0 to about 2.5 molar equivalents relative to the moles of the compound of formula (V-K).

25. A process as in claim 22, wherein the alkyl lithium is added to a mixture of the compound of formula (V-K) and the compound of formula (VI-S) in the organic solvent.

26. A process as in claim 22, wherein the BF$_3$OEt$_2$ is present in an amount in the range of from about 2.0 to about 6.0 molar equivalents relative to the moles of the compound of formula (VII-K) and wherein the trialkylsilane is Et$_3$SiH and is present in an amount in the range of from about 2.0 to about 6.0 molar equivalents relative to the moles of the compound of formula (VII-K).

27. A process as in claim 26, wherein the molar ratio of BF$_3$OEt$_2$: Et$_3$SiH is about 1:1.

28. A process as in claim 22, wherein the compound of formula (VIII-K) is reacted with acetic anhydride and wherein the acetic anhydride is present in an amount in the range of from about 4.5 to about 5.0 molar equivalents relative to the moles of the compound of formula (VIII-K).

29. A process as in claim 22, wherein the organic base is NMM.

30. A process as in claim 22, wherein the compound of formula (VIII-K) is reacted with acetic anhydride in the presence of a catalytic amount of DMAP.

31. A process as in claim 22, wherein the compound of formula (IX-K) is de-protected by reacting with a base.

* * * * *

UNITED STATES PATENT AND TRADEMARK OFFICE
CERTIFICATE OF CORRECTION

| | | |
|---|---|---|
| PATENT NO. | : 9,024,009 B2 | Page 1 of 1 |
| APPLICATION NO. | : 12/207252 | |
| DATED | : May 5, 2015 | |
| INVENTOR(S) | : Abdel-Magid et al. | |

It is certified that error appears in the above-identified patent and that said Letters Patent is hereby corrected as shown below:

Claims

Column 72
　　　Line 39, Claim 13, delete "form" and insert --from--.

Column 76
　　　Line 24, Claim 24, delete "form" and insert --from--.

Signed and Sealed this
Seventeenth Day of November, 2015

Michelle K. Lee
*Director of the United States Patent and Trademark Office*